United States Patent
Strano et al.

(10) Patent No.: US 10,012,657 B2
(45) Date of Patent: Jul. 3, 2018

(54) OPTICAL NANOSENSORS COMPRISING PHOTOLUMINESCENT NANOSTRUCTURES

(71) Applicant: Massachusetts Institute of Technology, Cambridge, MA (US)

(72) Inventors: Michael S. Strano, Lexington, MA (US); Jong-Ho Kim, Cambridge, MA (US); Jinqing Zhang, Hangzhou (CN); Daniel A. Heller, Rye Brook, NY (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 473 days.

(21) Appl. No.: 13/942,241

(22) Filed: Jul. 15, 2013

(65) Prior Publication Data

US 2014/0080122 A1    Mar. 20, 2014

Related U.S. Application Data

(63) Continuation of application No. 12/860,752, filed on Aug. 20, 2010, now Pat. No. 8,486,709.

(60) Provisional application No. 61/235,921, filed on Aug. 21, 2009.

(51) Int. Cl.

| | |
|---|---|
| *G01N 33/84* | (2006.01) |
| *G01N 21/64* | (2006.01) |
| *G01N 33/543* | (2006.01) |
| *B82Y 15/00* | (2011.01) |
| *B82Y 30/00* | (2011.01) |
| *G01N 21/77* | (2006.01) |

(52) U.S. Cl.
CPC ......... *G01N 33/84* (2013.01); *G01N 21/6428* (2013.01); *G01N 33/54346* (2013.01); *G01N 33/54373* (2013.01); *B82Y 15/00* (2013.01); *B82Y 30/00* (2013.01); *G01N 21/6489* (2013.01); *G01N 2021/6432* (2013.01); *G01N 2021/7786* (2013.01); *Y10T 436/177692* (2015.01)

(58) Field of Classification Search
CPC ...... Y10T 436/177692; G01N 21/6428; G01N 33/54373; G01N 33/54346; G01N 33/84; G01N 21/6489; G01N 2021/7786; G01N 2021/6432; B82Y 15/00; B82Y 30/00
See application file for complete search history.

(56) References Cited

U.S. PATENT DOCUMENTS

| | | | |
|---|---|---|---|
| 8,765,488 B2 * | 7/2014 | Strano | B82Y 15/00 435/14 |
| 2007/0292896 A1 | 12/2007 | Strano et al. | |

OTHER PUBLICATIONS

Rether et al. "Isolation of polysaccharide-free DNA from plants." Plant Molecular Biology Reporter (1993) 11 333-337.*

(Continued)

*Primary Examiner* — Christopher Adam Hixson
(74) *Attorney, Agent, or Firm* — Steptoe & Johnson LLP

(57) ABSTRACT

Systems and methods related to optical nanosensors comprising photoluminescent nanostructures are generally described. Generally, the nanosensors comprise a photoluminescent nanostructure and a polymer that interacts with the photoluminescent nanostructure. In some cases, the interaction between the polymer and the nanostructure can be non-covalent (e.g., via van der Waals interactions). The nanosensors comprising a polymer and a photoluminescent nanostructure may be particularly useful in determining the presence and/or concentration of relatively small molecules, in some embodiments. In addition, in some instances the nanosensors may be capable of determining relatively low concentrations of analytes, in some cases determining as little as a single molecule. In some embodiments, the interaction between the analyte and the nanosensor (e.g., between the analyte and the photoluminescent nanostructure) can be reversible, which may allow, for example, for the reuse of a nanosensor after it has been exposed to an analyte.

15 Claims, 41 Drawing Sheets

(56) References Cited

OTHER PUBLICATIONS

Gigliotti, Brittany et al. "Sequence-independent helical wrapping of single-walled carbon nanotubes by long genomic DNA." Nano Letters (2006) 6 159-164.*

Kim, Jong-Ho et al, "The rational design of nitric oxide selectivity in single-walled carbon nanotube near-infrared fluorescence sensors for biological detection," Nature Chemistry, vol. 1, No. 6, Sep. 2009, pp. 473-481.

Barone, Paul W. et al., "In vivo fluorescence detection of glucose using a single-walled carbon nanotube optical sensor: design, fluorophore properties, advantages, and disadvantages," Analytical Chemistry, American Chemical Society, US, vol. 77, No. 23, Dec. 2005, pp. 7556-7562.

Heller, D A et al., "Multimodal optical sensing and analyte specificity using single-walled carbon nanotubes," Nature Nanotechnology Feb. 2009 GB, vol. 4, No. 2, Feb. 2009, pp. 114-120.

Barone, Paul W. et al., "Single walled carbon nanotubes as reporters for the optical detection of glucose" Journal of Diabetes Science and Technology, Diabetes Technology Society, US, vol. 3, No. 2 Jan. 1, 2009, pp. 242-252.

Heller D A et al., "Single-walled carbon nanotube spectroscopy in live cells: Toward long-term labels and optical sensors" Advanced Materials Dec. 5, 2005 Wiley-VCH Verlag DE, vol. 17, No. 23, Dec. 5, 2005, pp. 2793-2799.

International Search Report and Written Opinion of the International Searching Authority dated Nov. 8, 2010 for PCT/US2010/046206.

International Preliminary Report on Patentability dated Mar. 1, 2012 for PCT/US2010/046206.

Zheng, Ming et al. "DNA-assisted dispersion and separation of carbon nanotubes." Nature Materials (2003) 338-342.

Zheng, Ming et al. "Structure-Based Carbon Nanotube Sorting by Sequence-Dependent DNA Assembly." Science (2003) 1545-1548.

* cited by examiner

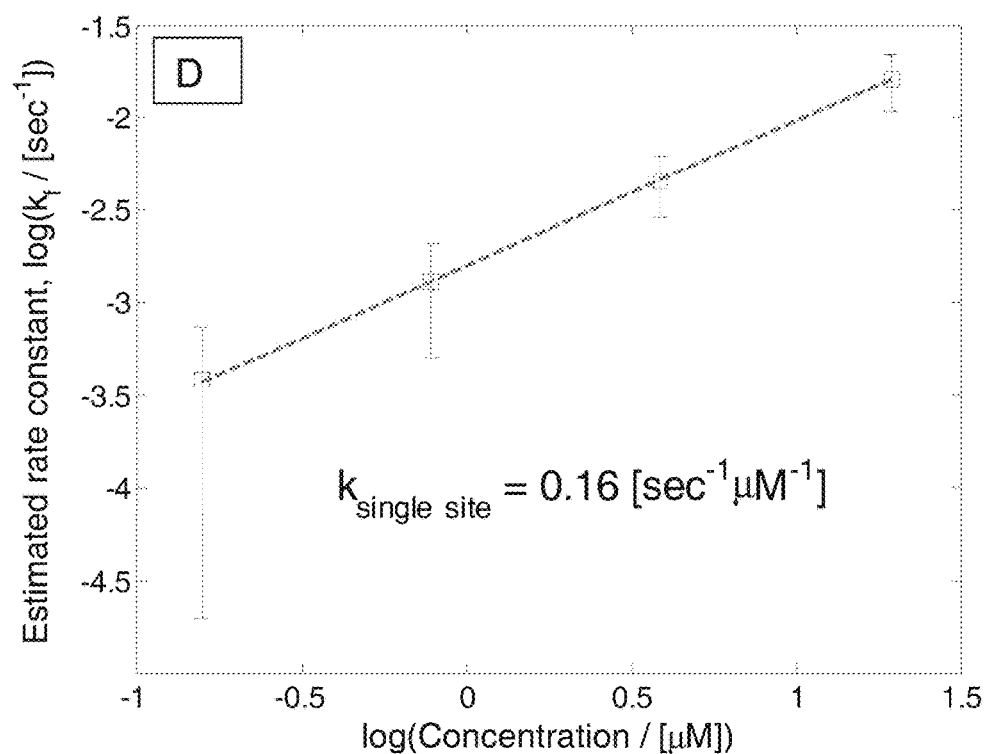
FIG. 14 C and D

OPTICAL NANOSENSORS COMPRISING PHOTOLUMINESCENT NANOSTRUCTURES

CLAIM OF PRIORITY

This application claims priority to U.S. application Ser. No. 12/860,752, filed on Aug. 20, 2010, which claims priority to U.S. Provisional Application No. 61/235,921, filed Aug. 21, 2009, each of which is incorporated by reference in its entirety.

FEDERALLY SPONSORED RESEARCH OR DEVELOPMENT

This invention was made with government support under Grant No. NSF0753036 awarded by the National Science Foundation. The government has certain rights in this invention.

TECHNICAL FIELD

Systems and methods related to optical nanosensors comprising photoluminescent nanostructures, which can be used, for example, to determine nitric oxide are generally described.

BACKGROUND

Small molecules can play roles as intracellular messengers for signaling pathways within the human body. For example, nitric oxide (NO) can participate in signaling in the cardiovascular and nervous systems, and can be employed in the human immune response system. Detection of small molecules has traditionally been relatively difficult, and becomes even more difficult at low concentrations. Examples of tools that may be used to detect such species include, for example, visible-fluorescence probes, chemiluminescence-based devices, and X-ray photoelectron and electron paramagnetic resonance (EPR) spectroscopy. For example, in the case of NO, a series of diaminofluoresceins and metal-fluorophore complexes have been widely applied to detect cellular NO. However, such methods may include significant limitations. For example, diaminofluoresceins generally detect molecules indirectly (e.g., via oxidation products). Other limitations include photobleaching and lack of optical penetration through biological tissues for metal-fluorophore complexes. Therefore, the design of more robust schemes for the biological detection of relatively small molecules is still an active area of research.

SUMMARY

Systems and methods related to optical nanosensors comprising photoluminescent nanostructures for the determination of, for example, nitric oxide are generally described. The subject matter of the present invention involves, in some cases, interrelated products, alternative solutions to a particular problem, and/or a plurality of different uses of one or more systems and/or articles.

In one aspect, a nanosensor can include a photoluminescent nanostructure and a polymer interacting with the photoluminescent nanostructure. The polymer can include a phenyl group. The nanosensor can emit a first emission of electromagnetic radiation in the absence of an analyte, and the nanosensor can emit a second emission of electromagnetic radiation upon interacting with the analyte. The analyte concentration can be less than about 100 micromolar.

In another aspect, a nanosensor can comprise a photoluminescent nanostructure, and a polymer interacting with the photoluminescent nanostructure. The nanosensor can emit a first emission of electromagnetic radiation in the absence of nitric oxide, and the nanosensor can emit a second emission of electromagnetic radiation upon interacting with nitric oxide at concentrations of less than about 100 micromolar. The interaction between the nitric oxide and the nanosensor can be reversible.

In another aspect, a nanosensor can include a photoluminescent nanostructure, and a polymer interacting with the photoluminescent nanostructure. The nanosensor can emit a first emission of electromagnetic radiation in the absence of an analyte, and the nanosensor can emit a second emission of electromagnetic radiation upon interacting with the analyte at analyte concentrations of less than about 100 micromolar. In some instances, the analyte has a molecular weight of less than about 1000 g/mol.

In another aspect, a nanosensor for detecting an analyte can include a photoluminescent nanostructure and a polymer, which can interact with the photoluminescent nanostructure, where the nanosensor can emit a first emission of electromagnetic radiation in the absence of the analyte, and the nanosensor can emit a second emission of electromagnetic radiation upon interacting with the analyte at concentrations of less than about 100 micromolar.

In another aspect, a method can include exposing a nanosensor including a photoluminescent nanostructure and a polymer interacting with the photoluminescent nanostructure to a solution containing nitric oxide at a concentration of less than about 100 micromolar. The method may further include determining the nitric oxide based upon an interaction between the nitric oxide and the nanosensor.

In another aspect, a method can include exposing a nanosensor including a photoluminescent nanostructure and a polymer interacting with the photoluminescent nanostructure to a solution containing an analyte at a concentration of less than about 100 micromolar and determining the analyte based upon an interaction between the analyte and the nanosensor.

In some embodiments, the interaction between the analyte and the nanosensor can be reversible. The interaction between the polymer and the photoluminescent nanostructure can be reversible without breaking any covalent bonds. In some embodiments, the interaction between the polymer and the photoluminescent nanostructure can be reversible via dialysis. In some embodiments, the interaction between the analyte and the nanosensor includes an interaction between the analyte and the photoluminescent nanostructure.

In some embodiments, the photoluminescent nanostructure can include a carbon nanotube. The carbon nanotube can be a single-walled carbon nanotube, such as a semiconductive single-walled carbon nanotube.

In some embodiments, the polymer can include a polysaccharide, for example, dextran. In some embodiments, the polymer can include an oligonucleotide or a polynucleotide. The oligonucleotide can include oligo(AT), or the polynucleotide can include poly(AT).

In some embodiments, the photoluminescent nanostructure can emit near-infrared radiation in the absence of the analyte or in the presence of the analyte. The nanosensor can emit electromagnetic radiation of a first intensity in the absence of the analyte, and the nanosensor can emit electromagnetic radiation of a second intensity that is less than the first intensity upon interacting with the analyte.

In some embodiments, the analyte can be analyte within a cell. In some embodiments, the analyte can be produced by a cell. The analyte can have a molecular weight of less than 1000 g/mol, of less than 100 g/mol, or less than 30 g/mol. In some embodiments, the analyte can be nitric oxide.

In some embodiments, the concentration of the analyte can be less than 100 micromolar, less than 10 micromolar or less than 1 micromolar. In some embodiments, a single molecule of the analyte can be present.

In some embodiments, a method can further include exposing the photoluminescent nanostructure to the interior of a cell. The method can further include determining an analyte within a cell. The method can further include determining an analyte produced by a cell. The method can further include determining an analyte for the diagnosis or management of at least one of asthma, rheumatoid arthritis, multiple sclerosis, tuberculosis, Alzheimer's disease, and cancer. In some embodiments, a method can further include determining the presence of a single analyte molecule.

Other advantages and novel features of the present invention will become apparent from the following detailed description of various non-limiting embodiments of the invention when considered in conjunction with the accompanying figures.

BRIEF DESCRIPTION OF THE DRAWINGS

FIG. 14C: Mean and variance of the kf,MLE estimated from the birth-and-death Markov model as a function of concentration of NO. FIG. 14D: Mean (square) and standard deviation (error bar) of kf,MLE is plotted against concentration of NO in a log-log scale. Single site adsorption rate constant of NO adsorption is estimated by fitting the data with the rate constant relationship, kf=ksingle siteC, and ksingle site is estimated to be 0.16 sec-1 µM NO-1. The red dotted line shows the linearly fitted curve in log-log scale.

DETAILED DESCRIPTION

Figure 1A:
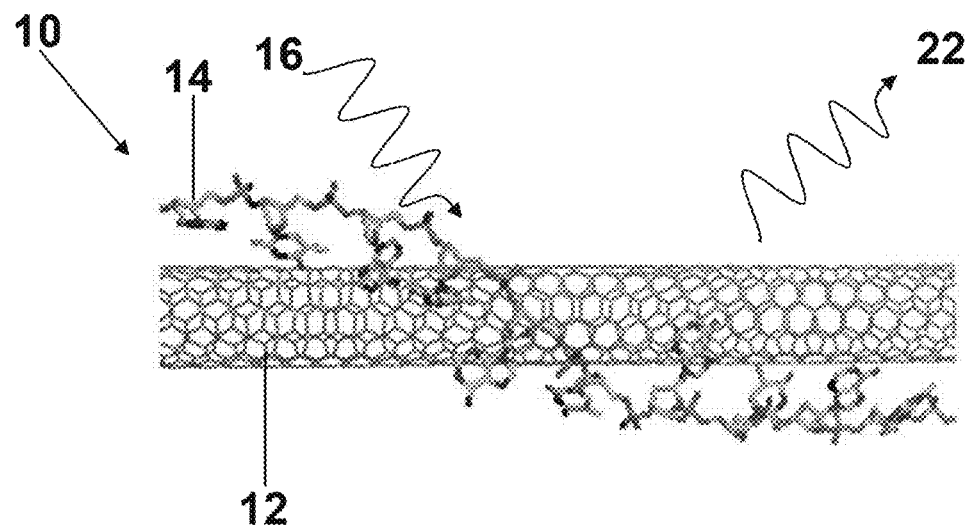
FIGS. 1A-1B include schematic illustrations of nanosensors, according to one set of embodiments.

Systems and methods related to optical nanosensors comprising photoluminescent nanostructures for the determination of, for example, nitric oxide are generally described. Generally, the nanosensors comprise a photoluminescent nanostructure and a polymer that interacts with the photoluminescent nanostructure. In some cases, the interaction between the polymer and the nanostructure can be non-covalent (e.g., via van der Waals interactions). The nanosensors comprising a polymer and a photoluminescent nanostructure may be particularly useful in determining the presence and/or concentration of relatively small molecules (e.g., nitric oxide), in some embodiments. In addition, in some instances the nanosensors may be capable of determining relatively low concentrations of analytes, in some cases determining as little as a single molecule. In some embodiments, the interaction between the analyte and the nanosensor (e.g., between the analyte and the photoluminescent nanostructure) can be reversible, which may allow, for example, for the reuse of a nanosensor after it has been exposed to an analyte.

Nitric oxide (NO) is a key molecule associated with many bio-functions including cell signaling, host defense, vasodilation, and sometimes cause disorders such as carcinogenesis[1-2]. One difficulty in NO research is that even within one single disease, there are can be conflicting hypotheses regarding the role of NO with no clear answers. To date, it is well agreed that the two fundamental factors of NO effects are the amount of NO as well as the location where it is produced[3-4]. Being a radical, NO is difficult to detect and even more difficult to quantify because of its rapid diffusivity and its high reactivity to species such as oxygen (in vitro) and hemoglobin (in vivo)[5].

An analytical probe capable of directly quantifying NO concentration with high spatial resolution (micron-scale) promises the potential of both accurately measuring NO at single cell level and studying NO-mediated signaling in vitro. The most widely used measuring method, Greiss assay, is robust but indirect, as it only measures the oxidation product of NO, nitrite, instead of NO itself. In addition, techniques such as NO electrodes (reviewed in reference [5]), electron paramagnetic resonance[5-6] and chemiluminescence[5, 7-8] have shown to quantify NO directly with high sensitivity, but they generally lack spatial resolution, and the latter two usually require complex instrumentation. Another alternative to quantify NO with good spatial resolution is the commonly used fluorescent probes[9-12] combined with microscopy. Although easy to use, organic fluorescence-based probes suffer from photobleaching threshold [9-12] preventing them from long-term imaging, and most of them are indirect[9-11] or non-quantitative[12].

Single-walled carbon nanotubes (SWNT) are useful materials for optical sensing and imaging. SWNT are cylindrical graphene layers with nanometer-sized diameters that emit stable near-infrared (NIR) light with no reported photobleaching threshold[13-15], which allows prolonged imaging in living cells and tissues[15-19]. Moreover, their one-dimensional electronic structure results in great sensitivity to analytes of interest, and even single-molecule adsorption on the sidewall of the SWNT can be recorded through quenching of excitons, or in other words, changes in fluorescence [20-25]. The recorded fluorescence modulation supplemented with proper calibration provides a sensitive determination of the concentration of the quencher molecule [18-19, 23-24]. Furthermore, compared with small molecule fluorescent probes, non-diffusive SWNTs allows otherwise impossible quantification of molecules with precise spatial resolution.

The nanosensors described herein may exhibit one or more advantageous properties relative to traditional sensors. The nanosensors described herein generally determine the analyte via a direct interaction between the analyte and a component of the nanosensor (e.g., the photoluminescent nanostructure), rather than via an interaction between a by-product of a reaction involving an analyte and a component of the nanosensor. The ability to determine the analyte based upon such a direct interaction can be useful in reducing or effectively eliminating unwanted interference between the analyte of interest and a background species. The nanosensors described herein can also exhibit relatively low amounts of undesired photobleaching, which can reduce or effectively eliminate distortions in the signal produced by the photoluminescent nanosensor. The nanosensors may also exhibit little or no overlapping with auto-fluorescence from endogenous fluorophores, in some cases. Moreover, the nanosensors described herein can emit wavelengths capable of penetrating human tissue (e.g., near-infrared radiation), making the nanosensors particularly suitable, for example, for in vivo testing in humans. In addition, as mentioned, the nanosensors described herein can be capable of determining relatively small analytes, optionally at very low concentrations.

The nanosensors described herein may be useful in a wide variety of applications, and may be particularly useful in determining the presence and/or concentration of nitric oxide (NO) in some embodiments. For example, the nanosensors can be used to determine NO as a pollutant. In addition, accumulating evidence suggests that elevated levels of NO during inflammation may be associated with numerous disorders such as, for example, asthma, rheumatoid arthritis, multiple sclerosis, tuberculosis, Alzheimer's disease, and cancer. The ability to determine nitric oxide may be helpful in diagnosing and/or managing such conditions. For example, the amount of nitric oxide in exhaled air can be useful in the treatment of asthma by providing information that can be used to diagnose subjects, distinguish subjects who will benefit from inhaled corticosteroids from those who will not, predict exacerbations, predict successful steroid reduction or withdrawal, and/or adjust steroid doses. Such applications are described, for example, in Pijnenburg, M. W. H., et al., "Exhaled nitric oxide in childhood asthma: a review," *Clinical and Experimental Allergy*, 38, pp. 246-259, which is incorporated herein by reference in its entirety.

The nanosensors described herein may also be useful in determining the amount of NO released by NO-releasing drugs. NO moieties have been attached to non-steroidal anti-inflammatory drugs (NSAIDs) to counteract side-effects associated with the use of NSAIDs. The resulting new chemical entities, termed 'NO-NSAIDs', have been shown to not only reduce the side effects associated with conventional NSAIDs, but have also exhibited significantly higher cytostatic and cytocidal activity than that of the native molecule in different cancer cell lines in pre-clinical mice models. NO-donating compounds may also be useful in the treatment of cardiovascular disease, among others. The use of the nanosensors described herein to quantify the effects of such drugs may be useful, for example, in studying the effects of such drugs in clinical trials.

In one aspect, nanosensors comprising photoluminescent nanostructures are provided. As used herein, the term "nanostructure" refers to articles having at least one cross-sectional dimension of less than about 1 micron. In some embodiments, nanostructures can have at least one cross-sectional dimension of less than about 500 nm, less than about 250 nm, less than about 100 nm, less than about 75 nm, less than about 50 nm, less than about 25 nm, less than about 10 nm, or, in some cases, less than about 1 nm. Examples of nanostructures include nanotubes (e.g., carbon nanotubes), nanowires (e.g., carbon nanowires), graphene, and quantum dots, among others. In some embodiments, the nanostructures include a fused network of atomic rings, the atomic rings comprising a plurality of double bonds.

A "photoluminescent nanostructure," as used herein, refers to a class of nanostructures that are capable of exhibiting photoluminescence. In some embodiments, photoluminescent nanostructures exhibit fluorescence. In some instances, photoluminescent nanostructures exhibit phosphorescence. Examples of photoluminescent nanostructures suitable for use include, but are not limited to, single-walled carbon nanotubes (SWCNTs), double-walled carbon nanotubes (DWCNTs), multi-walled carbon nanotubes (MWCNTs), semi-conductor quantum dots, semi-conductor nanowires, and graphene, among others.

In some embodiments, the systems and methods described herein may allow for selective determination of an analyte. The term "selective" is used to indicate an interaction that is sufficiently specific that it can be used to distinguish the analyte in practice from other chemical species in the system in which the nanosensor is to be employed. For example, in some cases, the nanosensors described herein can determine the presence of NO without substantial interference from other compounds such as $NO_2^-$, $NO_3^-$, $ONO_2^-$, HNO, $OCl^-$, hydroxyl radicals, $H_2O_2$, and the like. In some embodiments, the analyte may produce a change in photoluminescence of a nanostructure that is at least about 2 times, at least about times, at least about 10 times, at least about 50 times, or at least about 100 times greater than the largest change in photoluminescence produced by another entity (e.g., a background molecule).

Figure 1B:
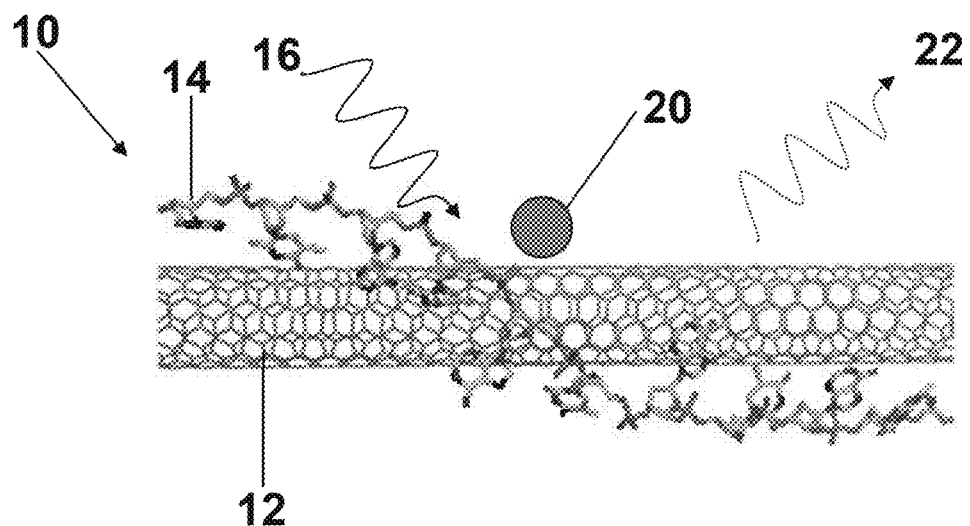

FIGS. 1A-1B include schematic diagrams of a nanosensor, according to one set of embodiments. In FIG. 1A, nanosensor 10 comprises photoluminescent nanostructure 12 and polymer 14 that interacts with the photoluminescent nanostructure. The photoluminescent nanostructure and the polymer can interact with each other, in some embodiments, via van der Waals forces (e.g., physisorption). In some embodiments, the photoluminescent nanostructure and the polymer are not covalently bonded to each other.

While polymer 14 is shown in FIGS. 1A-1B as being helically wrapped around nanostructure 12, it should be understood that the polymer may assume any suitable shape or conformation when interacting with the nanostructure. In some embodiments, the polymer may at least partially surround the nanostructure. A first entity is said to "at least partially surround" a second entity if a closed loop can be drawn around the second entity through only the first entity. In some cases, the polymer may be positioned proximate to the nanostructure such that it completely surrounds the nanostructure with the exception of relatively small volumes. The presence of these small volumes may allow for the passage of an analyte such that the analyte and the photoluminescent nanostructure can interact (e.g., via van der Waals forces, via electrical communication, etc) while optionally preventing non-analyte entities from interacting with the photoluminescent nanostructure. A first entity is said to "completely surround" a second entity if closed loops going through only the first entity can be drawn around the second entity regardless of direction.

In FIG. 1A, incident electromagnetic radiation 16 interacts with the photoluminescent nanostructure, in the absence of the analyte, resulting in a first emission of radiation 18. The emission of radiation can be produced, for example, via photo-induced band gap fluorescence. For example, single-walled carbon nanotubes (e.g., semi-conductive single-walled carbon nanotubes) are known to exhibit band gap fluorescence when photo-induced by electromagnetic radiation of appropriate wavelength. In some embodiments, the emission of radiation from a nanostructure can occur despite the substantial absence of a dopant or the substantial absence of a p-n junction within the nanostructure. For example, single-walled carbon nanotubes can exhibit photo-induced band gap fluorescence despite comprising no p-n junction or dopants.

In some embodiments, the photoluminescent nanostructure may be substantially free of covalent bonds with other entities (e.g., other nanostructures, a current collector, the surface of a container, a polymer, an analyte, etc.). The absence of covalent bonding between the photoluminescent nanostructure and another entity may, for example, preserve the photoluminescent character of the nanostructure. As a specific example, single-walled carbon nanotubes may exhibit modified or substantially no fluorescence upon forming a covalent bond with another entity (e.g., another nanotube, a current collector, a surface of a container, and the like).

In FIG. 1B, analyte 20 is interacts with photoluminescent nanostructure 12. The term "analyte" generally refers to any chemical species which is to be determined (e.g., quantitatively or qualitatively). Analyte 20 can, in some cases, interact with photoluminescent nanostructure 12 such that no covalent bonds are formed between the analyte and the photoluminescent nanostructure. In some embodiments, the analyte and the photoluminescent nanostructure may interact via van der Waals forces.

In some embodiments, the interaction between the analyte and the nanosensor may be reversible. Not wishing to be bound by any theory, the reversibility of the interaction between the analyte and the nanosensor may be due, in some cases, to the non-covalent interaction between the analyte and the nanosensor. In some embodiments, the interaction between the analyte and the nanosensor can be reversed without breaking any covalent bonds between the analyte and the nanosensor. For example, in some cases, the interaction between the nanosensor and the analyte can be reversed via dialysis of the analyte-adsorbed nanosensor. One of ordinary skill in the art would be familiar with the process of dialysis, which generally refers to the process of separating entities (e.g., analyte and nanosensor) in a fluid (e.g., in solution) based upon differences in their rates of diffusion through a membrane (e.g., a semipermeable membrane). The ability to reverse the interaction between the analyte and the nanosensor can allow for re-use of the nanosensor after it has been exposed to an analyte.

Referring back to FIG. 1B, in some embodiments, incident electromagnetic radiation 16 can interact with a photoluminescent nanostructure that is interacting with analyte 20 to produce a second emission of radiation 22, which can be substantially different than first emission of radiation 18. In some cases, the second emission of radiation produced by the nanostructure in association with the analyte is of a different intensity (e.g., larger or smaller intensity) or different wavelength (e.g., shorter or longer wavelength) relative to the first emission of radiation produced by the nanostructure in the absence of an interaction with the analyte. For example, in some cases, the nanostructure may exhibit photoluminescence bleaching (i.e., a decrease in photoluminescent intensity) when associated with the analyte. In some embodiments, substantially no radiation is emitted by the nanostructure (e.g., after interacting with incident electromagnetic radiation) when it is interacting with an analyte.

The analyte can be, in some cases, in electrical communication with the photoluminescent nanostructure. In some embodiments, the photoluminescent nanostructure and the polymer are in direct electrical communication with each other. As used herein, two entities are said to be in "direct electrical communication" with each other when they are capable of directly exchanging electrons with each other, without the electrons passing through a third entity. In contrast, "indirect electrical communication" refers to situations in which first and second entities are capable of exchanging electrons with each other only via a third entity. In some cases, the polymer may donate electrons to the photoluminescent nanostructure, producing excess electrons on the nanostructure. Such electron transfer may alter the way in which the nanostructure participates in direct electrical communication with an analyte. For example, in some embodiments, the polymer may comprise lone pairs of electrons on a pendant group (e.g., an amine) which can be transferred to the nanostructure and subsequently transferred to the analyte. Such electron transfer from the nanostructure to the analyte can produce, in some embodiments, a change in the luminescent nature of the nanostructure (e.g., photoluminescent bleaching). Examples of pendant groups that may be suitable for such electron transfer include, but are not limited to, amine groups (e.g., amino groups, diamino groups, etc.), imine, potassium, cesium, and the like.

In some cases, the polymer can adopt a shape such that it allows the analyte to interact with the photoluminescent nanostructure, but inhibits other molecules from interacting with the photoluminescent nanostructure. For example, after the polymer adopts the shape, interactions between the analyte and the photoluminescent nanostructure can be relatively energetically favored, while interactions between the photoluminescent nanostructure and non-analyte entities can be relatively energetically disfavored (e.g., due to steric hindrance). In some cases, the polymer may comprise pendant groups that, upon interacting with the photoluminescent nanostructure, transform the shape of the polymer relative to the shape the polymer would possess in the absence of the interaction with the photoluminescent nanostructure, such that the polymer at least partially surrounds the photoluminescent nanostructure. The transformed shape of the polymer may comprise openings through which the analyte can pass (e.g., due to being energetically favored) and interact with the photoluminescent nanostructure, in some cases. Also, in some embodiments, the openings may reduce or eliminate interaction between the photoluminescent nanostructure and at least one or substantially all background entities (e.g., due to being energetically disfavored). In some cases, the polymer can comprise pendant groups that enhance the selective passage of the analyte described above (e.g., via steric effects) without interacting with the photoluminescent nanostructure. As a specific example, dextran can be modified to contain pendant groups capable of participating in pi-pi interactions with the aromatic groups on carbon nanotubes (e.g., phenyl groups). The dextran, which may not generally adsorb to carbon nanotubes in the absence of the pendant groups, may interact with the carbon nanotube via the pi-pi interactions between the pendant groups and the aromatic rings within the nanotube. This can result in perturbations to the dextran structure such that interactions with analyte (e.g., NO) are energetically favored, while interactions with other molecules are not energetically favored.

In some cases, nanosensors may be useful in determining relatively small analytes. For example, in some embodiments, the analyte can have a molecular weight of about 1000 g/mol or less, about 500 g/mol or less, about 100 g/mol or less, or about 30 g/mol or less. For example, the nanosensors can be used to determine nitric oxide, which has a molecular weight of about 30 g/mol. Exemplary analytes that can be determined using the systems and methods described herein include, for example, nitric oxide, hydrogen peroxide, hydroxyl radical, glutamate, aspartate, serine, g-aminobutyric acid, glycine, dopamine, norepinephrine, epinephrine, serotonin, melatonin, acetylcholine, adenosine, anandamide, histamine, and the like.

In some embodiments, the systems and methods described herein may be capable of determining relatively low concentrations of an analyte. The ability to determine low concentrations of an analyte may be useful, for example, in detecting trace pollutants or trace amounts of toxins within a subject. In some embodiments, nanosensors can determine analyte concentrations of less than about 100 micromolar, less than about 10 micromolar, less than about 1 micromolar, less than about 100 nanomolar, less than about 10 nanomolar, or less than about 1 nanomolar. In some cases, nanosensors can be used to determine a single molecule of an analyte.

A variety of polymers may be used in association with the embodiments described herein. In some embodiments, the polymer may comprise a polysaccharide such as, for example, dextran, amylose, chitin, or cellulose. In some embodiments, the polymer may comprise a protein. Examples of suitable proteins include, but are not limited to glucose oxidase, bovine serum albumin and alcohol dehydrogenase. The polymer may also comprise a synthetic polymer (e.g., polyvinyl aclohol, poly(acrylic acid), poly(ethylene oxide), poly(vinyl pyrrolidinone), poly(allyl amine), poly(2-vinylpyridine), poly(maleic acid), and the like), in some embodiments. In some embodiments, the polymer may comprise a polynucleotide. For example, the polymer may comprise a series of repeated base pairs (e.g., repeated adenine-thymine (AT) base pairs, repeated guanine-thymine (GT) base pairs, etc.) In some embodiments, the polymer may comprise at least about 5, at least about 15, at least about 25, at least about 50, or at least about 100, between 5 and 30, or between 10 and 20, or about 15 repeated base pairs (e.g., AT, GT, and the like) in succession.

In another aspect, methods for sensing an analyte using nanosensors comprising photoluminescent nanostructures are provided. The method can comprise providing a photoluminescent nanosensor comprising a photoluminescent nanostructure and a polymer that interacts with the photoluminescent nanostructure. The polymer may interact with the photoluminescent nanostructure, for example, via any of the mechanisms described above. The method may further comprise exposing the photoluminescent nanosensor to a composition containing an analyte (e.g., any of the analytes described above including, for example, nitric oxide). The method may also comprise determining the analyte based upon the interaction between the analyte and the photoluminescent nanosensor. In some embodiments, the method may comprise determining an analyte with a relatively low molecular weight (e.g., about 1000 g/mol or less, about 500 g/mol or less, about 100 g/mol or less, or about 30 g/mol or less). In some instances, the concentration of the analyte may be relatively low (e.g., less than about 100 micromolar, less than about 10 micromolar, less than about 1 micromolar, less than about 100 nanomolar, less than about 10 nanomolar, less than about 1 nanomolar, or about a single molecule of the analyte).

In some embodiments, the method may comprise exposing the nanosensor to electromagnetic radiation. Sources of electromagnetic radiation that can be used include, but are not limited to, a lamp (e.g., an infrared lamp, ultraviolet lamp, etc.), a laser, LED, or any other suitable source. In addition, the method may further comprise sensing electromagnetic radiation (e.g., the intensity and/or wavelength) or the absorption of electromagnetic radiation, for example, emitted by the nanosensor. Sensing can be performed using, for example, a UV-vis-nIR spectrometer, a florometer, a fluorescence microscope, visual inspection (e.g., via observation by a person) or any other suitable instrument or technique.

In yet another aspect, a method of making a photoluminescent nanosensor is provided. The method of making the nanosensor may comprise, in some cases, exposing a photoluminescent nanostructure to a polymer capable of interacting with the photoluminescent nanostructure (e.g., via any of the mechanisms described above). In some embodiments, the photoluminescent nanostructure, the polymer or both may be provided within a fluid (e.g., a liquid). For example, exposing a photoluminescent nanostructure to the polymer can comprise adding the polymer to a fluid containing a photoluminescent nanostructure. Exposing a photoluminescent nanostructure to a polymer can also comprise adding a photoluminescent nanostructure to a fluid containing a polymer, in some cases. One of ordinary skill in the art will be able to identify other suitable methods for exposing a photoluminescent nanostructure to a polymer.

As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles (e.g., cells, vesicles, etc.), viscoelastic fluids, and the like. In some embodiments, the fluid may comprise water, chloroform, acetonitrile, N-methylpyrrolidone (NMP), or any other suitable fluid in which nanostructures (e.g., carbon nanotubes) can be suspended. In some embodiments, a fluid may be selected that is capable of forming a stable suspension of photoluminescent nanostructures (e.g., single-walled carbon nanotubes).

Certain embodiments of the present invention are generally directed to the use of nanosensors to determine an analyte (e.g., nitric oxide) within a cell, produced by a cell, and/or consumed by a cell. As used herein, a "cell" is given its ordinary meaning as used in biology. The cell may be any cell or cell type. In some embodiments, the cell is a human cell. The cell may be a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell.

The term "determining," as used herein, generally refers to the analysis or measurement of a species (e.g., an analyte), for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction.

As described above, a variety of nanostructures can be used in association with the nanosensors described herein. In some embodiments, carbon-based nanostructures are described. As used herein, a "carbon-based nanostructure" comprises a fused network of aromatic rings wherein the nanostructure comprises primarily carbon atoms. In some instances, the nanostructures have a cylindrical, pseudo-cylindrical, or horn shape. A carbon-based nanostructure can comprises a fused network of at least about 10, at least about 50, at least about 100, at least about 1000, at least about 10,000, or, in some cases, at least about 100,000 aromatic rings. Carbon-based nanostructures may be substantially planar or substantially non-planar, or may comprise a planar or non-planar portion. Carbon-based nanostructures may optionally comprise a border at which the fused network terminates. For example, a sheet of graphene comprises a planar carbon-containing molecule comprising a border at which the fused network terminates, while a carbon nanotube comprises a nonplanar carbon-based nanostructure with borders at either end. In some cases, the border may be substituted with hydrogen atoms. In some cases, the border may be substituted with groups comprising oxygen atoms (e.g., hydroxyl). In other cases, the border may be substituted as described herein.

In some embodiments, the nanostructures described herein may comprise nanotubes. As used herein, the term "nanotube" is given its ordinary meaning in the art and refers to a substantially cylindrical molecule or nanostructure comprising a fused network of primarily six-membered rings (e.g., six-membered aromatic rings). In some cases, nanotubes may resemble a sheet of graphite formed into a seamless cylindrical structure. It should be understood that the nanotube may also comprise rings or lattice structures other than six-membered rings. Typically, at least one end of the nanotube may be capped, i.e., with a curved or nonplanar aromatic group. Nanotubes may have a diameter of the order of nanometers and a length on the order of microns, tens of microns, hundreds of microns, or millimeters, resulting in an aspect ratio greater than about 100, about 1000, about 10,000, or greater. In some embodiments, a nanotube can have a diameter of less than about 1 micron, less than about 500 nm, less than about 250 nm, less than about 100 nm, less than about 75 nm, less than about 50 nm, less than about 25 nm, less than about 10 nm, or, in some cases, less than about 1 nm.

In some embodiments, a nanotube may comprise a carbon nanotube. The term "carbon nanotube" refers to nanotubes comprising primarily carbon atoms. Examples of carbon nanotubes include single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

In some embodiments, the nanostructures comprise non-carbon nanotubes. Non-carbon nanotubes may be of any of the shapes and dimensions outlined above with respect to carbon nanotubes. The non-carbon nanotube material may be selected from polymer, ceramic, metal and other suitable materials. For example, the non-carbon nanotube may comprise a metal such as Co, Fe, Ni, Mo, Cu, Au, Ag, Pt, Pd, Al, Zn, or alloys of these metals, among others. In some instances, the non-carbon nanotube may be formed of a semi-conductor such as, for example, Si. In some cases, the non-carbon nanotubes may be Group II-VI nanotubes, wherein Group II consists of Zn, Cd, and Hg, and Group VI consists of O, S, Se, Te, and Po. In some embodiments, non-carbon nanotubes may comprise Group III-V nanotubes, wherein Group III consists of B, Al, Ga, In, and Tl, and Group V consists of N, P, As, Sb, and Bi. As a specific example, the non-carbon nanotubes may comprise boron-nitride nanotubes.

In some embodiments, the nanotube may comprise both carbon and another material. For example, in some cases, a multi-walled nanotube may comprise at least one carbon-based wall (e.g., a conventional graphene sheet joined along a vector) and at least one non-carbon wall (e.g., a wall comprising a metal, silicon, boron nitride, etc.). In some embodiments, the carbon-based wall may surround at least one non-carbon wall. In some instances, a non-carbon wall may surround at least one carbon-based wall.

The term "quantum dot" is given its normal meaning in the art and is used to refer to semi-conducting nanostructures that exhibit quantum confinement effects. Generally, energy (e.g., light) incident upon a quantum dot will excite the quantum dot to an excited state, after which, the quantum dot will emit energy corresponding to the energy band gap between its excited state and its ground state. Examples of materials from which quantum dots can be made include PbS, PbSe, CdS, CdSe, ZnS, and ZnSe, among others.

The photoluminescent nanostructures described herein can be, in some cases, substantially free of dopants, impurities, or other non-nanostructure atoms. For example, in some embodiments, the nanostructure can comprise a carbon nanostructure that is substantially free of dopants. As a specific example, in some embodiments, the nanostructures may comprise single-walled carbon nanotube that contain only aromatic rings (each of which contains only carbon atoms) within the shell portion of the nanotube.

In some embodiments, the photoluminescent nanostructures described herein may emit radiation within a desired range of wavelengths. For example, in some cases, the photoluminescent nanostructures may emit radiation with a wavelength between about 750 nm and about 1600 nm, or between about 900 nm and about 1400 nm (e.g., in the near-infrared range of wavelengths). In some embodiments, the photoluminescent nanostructures may emit radiation with a wavelength within the visible range of the spectrum (e.g., between about 400 nm and about 700 nm).

In some embodiments, a kit including one or more of the compositions previously discussed (e.g., a kit including a nanosensor, a kit including a polymer and a photoluminescent nanostructure from which a nanosensor can be produced, etc.) that can be used to produce and/or employ a nanosensor, is described. A "kit," as used herein, typically defines a package or an assembly including one or more of the compositions of the invention, and/or other compositions associated with the invention, for example, as previously described. Each of the compositions of the kit may be provided in liquid form (e.g., a suspension of nanosensors, etc.), or in solid form. In certain cases, some of the compositions may be constitutable or otherwise processable, for example, by the addition of a suitable solvent, other species, or source of energy (e.g., electromagnetic radiation), which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

The following examples are intended to illustrate certain embodiments of the present invention, but do not exemplify the full scope of the invention.

Example 1

This example describes a 3,4-diaminophenyl-functionalized dextran (DAP-dex) wrapping for SWNTs that imparts rapid and selective fluorescence detection of nitric oxide (NO) in the near infrared (nIR). In this example, the donation of lone-pair electrons in amines can increase electron density and mobility in SWNTs. The SWNT/DAP-dex hybrid can function as an assay for NO based on transition bleaching. In addition, the SWNT/DAP-dex hybrid can exhibit enhanced selectivity to NO relative to other reactive nitrogen and oxygen species. The NO binding appeared to be non-covalent, and the SWNT/DAP-dex nanosensor can reversibly detect NO via the fluorescence bleaching mechanism. Spectral evidence supports a mechanism of electron transfer from the top of the valence band of SWNTs to the lowest unoccupied molecular orbital (LUMO) of the NO radical. The SWNT/DAP-dex nanosensor can be used for the real-time and spatially resolved detection of NO within living cells at nanomolar concentrations. NO produced by stimulating inducible NO synthase (iNOS) in Raw 264.7 macrophage cells was detected in real time using the fluorescence bleaching of SWNT/DAP-dex. In addition, the potential for the SWNT nanosensor to be used for the in vivo detection of NO using any platform has been demonstrated by injecting nanosensor complexes into a recently deceased mouse as a tissue phantom.

Preparation of SWNT/DAP-Dex

Figure 2A:
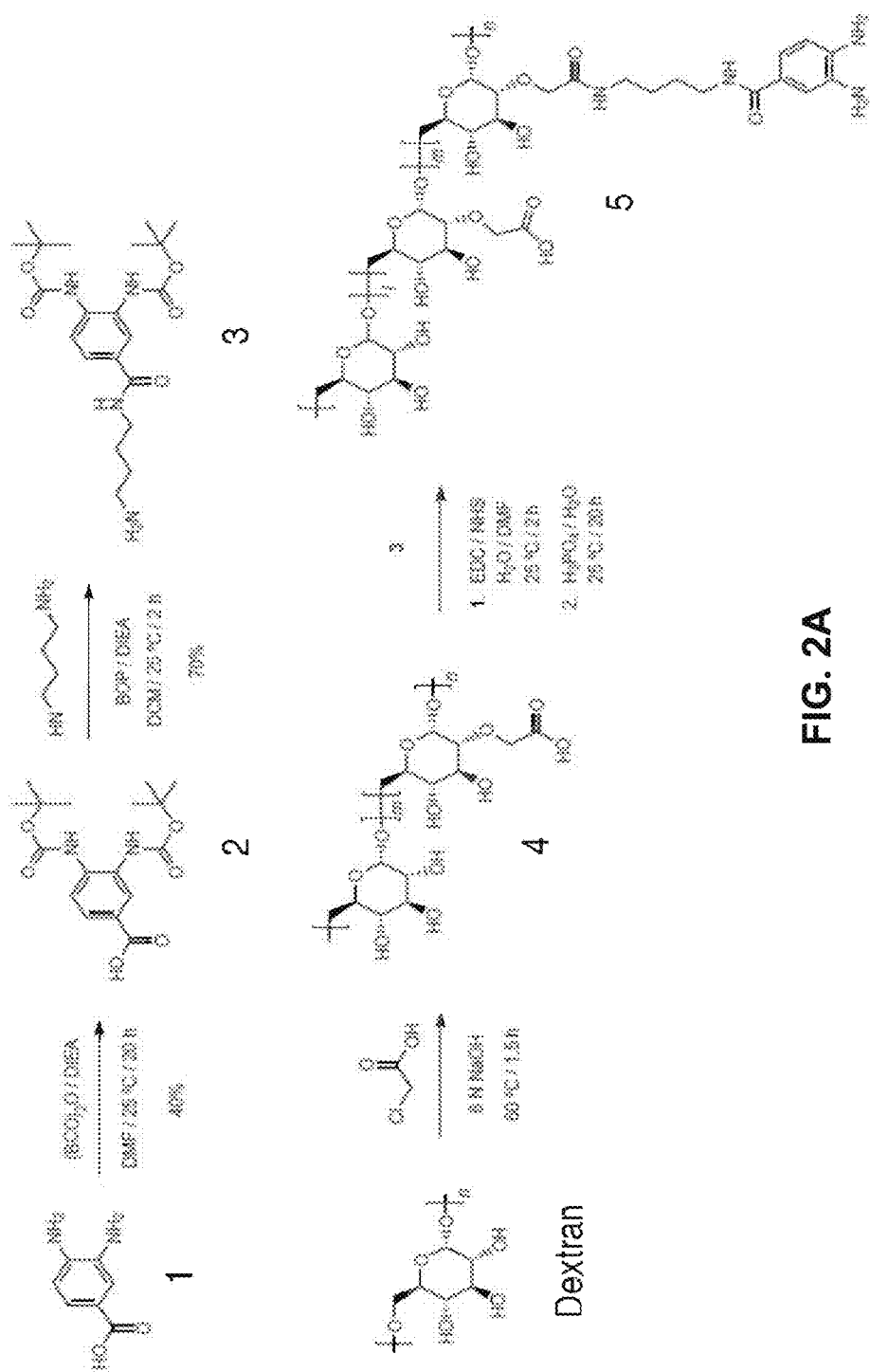
FIGS. 2A-2B include schematic illustrations of (A) the synthesis of DAP-dex and (B) the preparation of SWNT/DAP-dex by dialysis and a mechanism for nIR fluorescence bleaching, according to one set of embodiments.

To suspend SWNTs individually in water and render higher selectivity and sensitivity for NO, DAP-dex (5 in FIG. 2A) was synthesized as shown in FIG. 2A. First, 3,4-diaminobenzoic acid (DABA, 1 in FIG. 2A) was protected with a t-butyloxycarbonyl (BOC) group. This was accomplished by dissolving a 3.0 g portion of DABA (19.71 mmol) in 100 ml of N,N-dimethylformamide (DMF). 7.64 g of N,N-diisopropylethylamine (DIEA, 59.13 mmol) was added to the DABA-DMF solution. A 10.32 g portion of di-tbutyl dicarbonate (($BOC)_2O$, 47.30 mmol) was slowly added to the DABA mixture in an ice bath, and the resulting solution was left to stir for 20 hours at 25° C. To work up the reaction, an excess of DCM was added to the reaction mixture, and then the di-BOC-protected DABA (BOC-DABA, 2 in FIG. E1A) was extracted with an excess of an aqueous solution of sodium hydroxide (1 M, 500 ml). After acidifying the aqueous solution with an aqueous solution of HCl (1 M), BOC-DABA was immediately extracted with an excess of ethyl acetate. After evaporating the ethyl acetate, BOC-DABA was purified using column chromatography (hexane:ethyl acetate, 2:1 v/v) to produce a 40% yield.

To synthesize (5-(4-aminobutylcarbamoyl)-2-t-butoxycarbonylaminophenyl)carbamic acid t-butyl ester (BOC-DABA-$NH_2$, 3 in FIG. 2A), 1.98 ml of 1,4-diaminobutane (19.72 mmol) was dissolved in 60 ml of dichloromethane (DCM). After dissolving 1.39 g of BOC-DABA (3.94 mmol), 1.92 g of (benzotriazol-1-yloxy)tris (dimethylamino)phosphonium hexafluorophosphate (4.34 mmol), and 0.89 ml of DIEA (5.13 mmol) in 40 ml of DCM, the solution was added dropwise to 1,4-diaminobutane solution for 20 minutes at 25° C. The resulting mixture was left to stir for a further three hours at 25° C. After evaporating DCM, the desired product, aminobutylated BOC-DABA (BOC-DABA-$NH_2$), was separated using column chromatography (DCM:MeOH, 5:1 v/v) to achieve a 70% yield.

Dextran (9-11 kDa) was carboxymethylated using chloroacetic acid in an aqueous solution of sodium hydroxide for 1.5 hours at 60° C. From the results of acidimetric titration and mass increase, 24 wt % of carboxylic acid (4.19 mmol carboxylic acid per gram) was introduced onto dextran (CM-dex, 4 in FIG. 2A). 0.8 g of N-(3-dimethylaminopropyl)-N'-ethylcarbodiimide hydrochloride (4.19 mmol) and 0.96 g of N-hydroxysuccinimide (8.38 mmol) were added to 1.0 g of carboxymethylated dextran dissolved in 30 ml of $H_2O$. 0.89 g of BOC-DABA-$NH_2$ was dissolved in DMF and added to the dextran solution. The resulting mixture was left to stir for ten hours at 25° C. Then, after evaporating $H_2O$ with the addition of 30 ml EtOH, the reagents were washed out with EtOH several times to obtain the pure product. The BOC protecting group was removed in an aqueous solution of 2.46 g $H_3PO_4$ (25.14 mmol) over 20 hours at 25° C. The desired product, DAP-dex (5 in FIG. E1A), was precipitated in an excess of EtOH.

The DAP group in DAP-dex was indicated by a feature at 260 nm in the ultraviolet-visible (UV-vis) spectrum. The amount of substituted DAP group was determined by measuring the absorbance at 260 nm and comparing the result to a calibration curve. According to the UV-vis analysis, 11 wt % DAP was introduced onto CM-dex. The DAP-dex was also analyzed using Fourier transform infrared (FTIR) spectroscopy. Two specific bands at 1,650 $cm^{-1}$ and 1,530 $cm^{-1}$ were observed in FTIR spectra of DAP-dex, which corresponded to the (C=O) stretching band and the (—NH) bending vibration bend, respectively. As DAP-dex is very soluble in water, the amount of substituent did not diminish the solubility of the original dextran in water. For all the detection experiments, DAP-dex with a diaminophenyl content of 11 wt % was used.

Figure 2B:
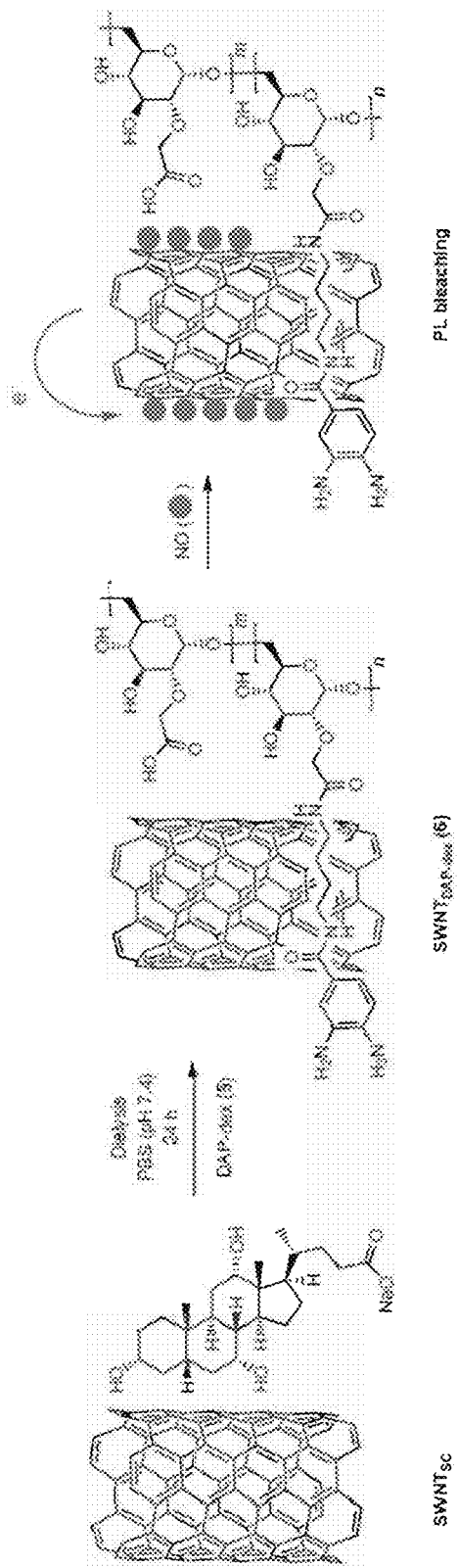
Figure 3A:
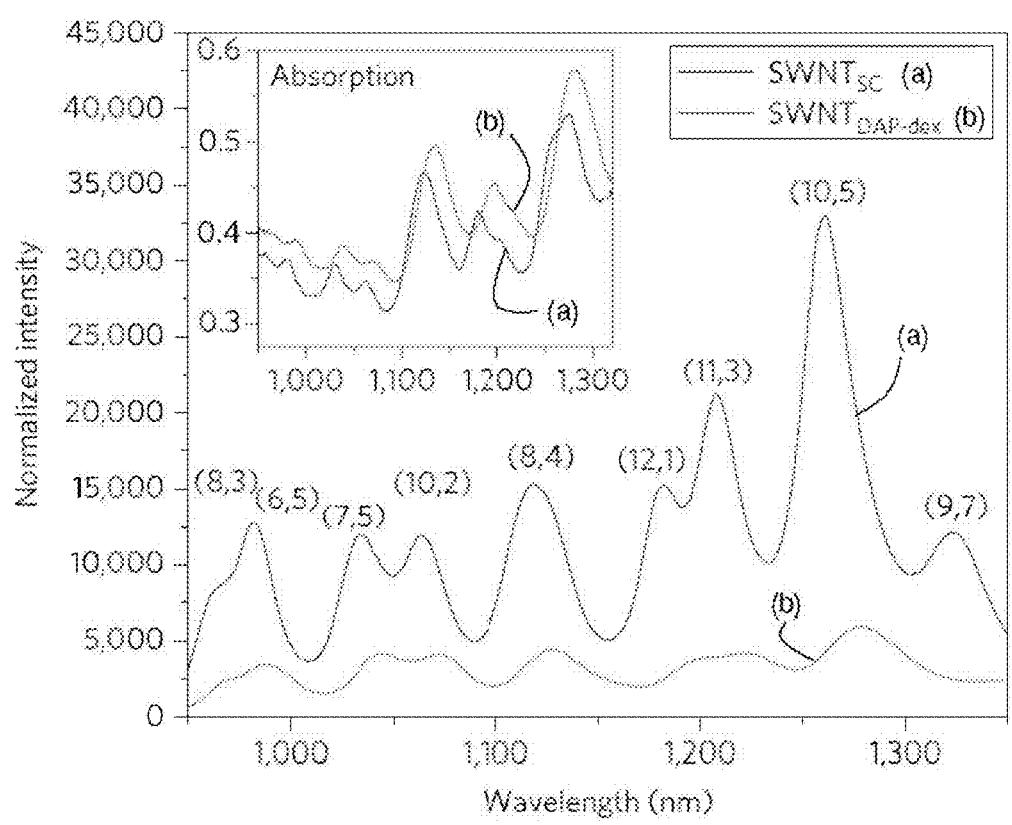
FIGS. 3A-3C include plots of the nIR fluorescence response of SWNT/DAP-dex nanosensors to NO, according to one set of embodiments.

To resuspend SWNTs with DAP-dex, dialysis of a mixture of 0.3 wt % DAP-dex and SWNTs suspended in sodium cholate (SWNT/SC, 12 mg $ml^{-1}$) against phosphate-buffered saline (PBS, 50 mM, pH 7.4) was carried out for 24 hours at 25° C., which removed sodium cholate and SWNTs suspended in DAP-dex. FIG. 2B includes a schematic illustration of the preparation of SWNT/DAP-dex (6 in FIG. 2B) by dialysis, as well as a mechanism for nIR fluorescence bleaching by NO. (In FIG. 2B, "PL" stands for photoluminescence.) As shown by atomic force microscopy and optical images, dialysis of SWNT/SC without DAP-dex caused SWNT aggregation, but SWNTs with DAP-dex were well suspended. Approximately 90% of the initial SWNT/SC was shown to be resuspended with DAP-dex based on the UV-vis-nIR absorption analysis. The fluorescence and absorption spectra (FIG. 3A) showed that a red shift (~18 nm or 14.5 meV) occurred for the SWNT/DAP-dex hybrid when sodium cholate was replaced with DAP-dex, which was similar to the shift observed in DNA-SWNTs. The normalized fluorescence intensity of SWNT/DAP-dex was lower compared to SWNTs suspended in sodium cholate, although the absorption intensities were similar to each other (see inset in FIG. 3A). This behavior observed in SWNT/DAP-dex was consistent with a mechanism of photoinduced excited-state electron transfer from the nanotube conduction band to the LUMO of an adsorbing molecule. Further, the reduction potential of the DAP group measured by cyclic voltammetry was −0.15 V (versus a normal hydrogen electrode), lying within the gap between the valence and conduction bands of SWNTs in this range, supporting the mechanism for the initial diminution of nIR fluorescence. In spite of this initial diminution, the residual nIR fluorescence of SWNT/DAP-dex was adequate for NO detection, as described below.

nIR Fluorescence Response of SWNT/DAP-Dex to NO

Figure 3B:
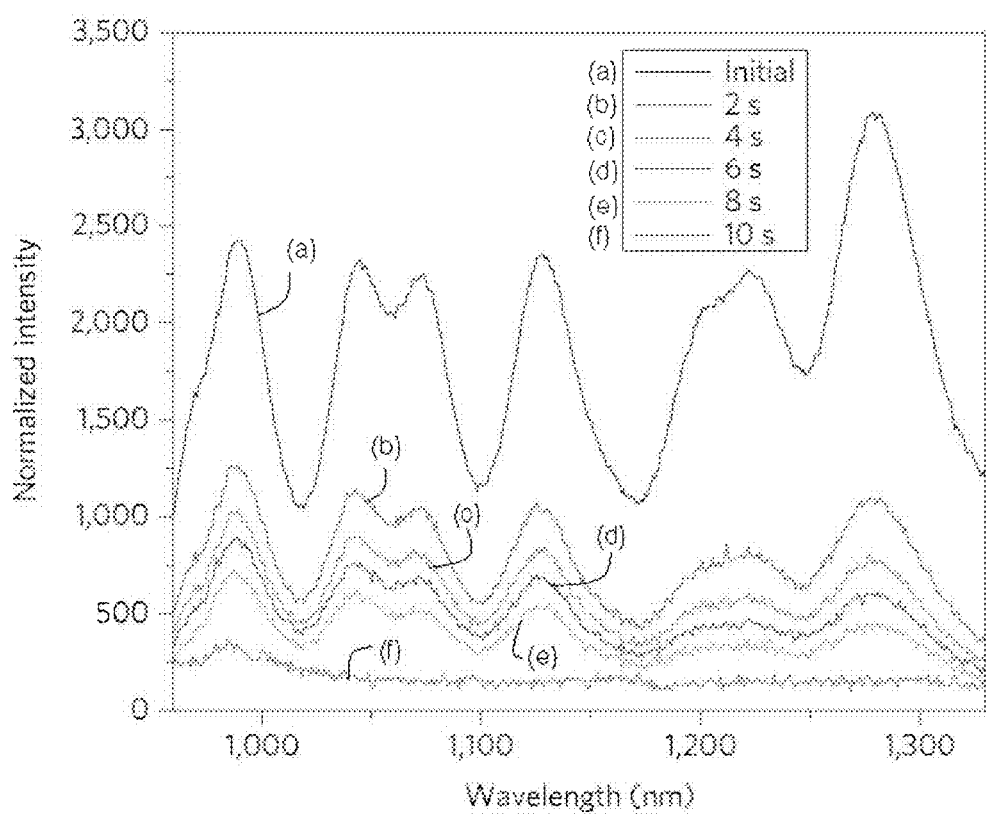
Figure 3C:
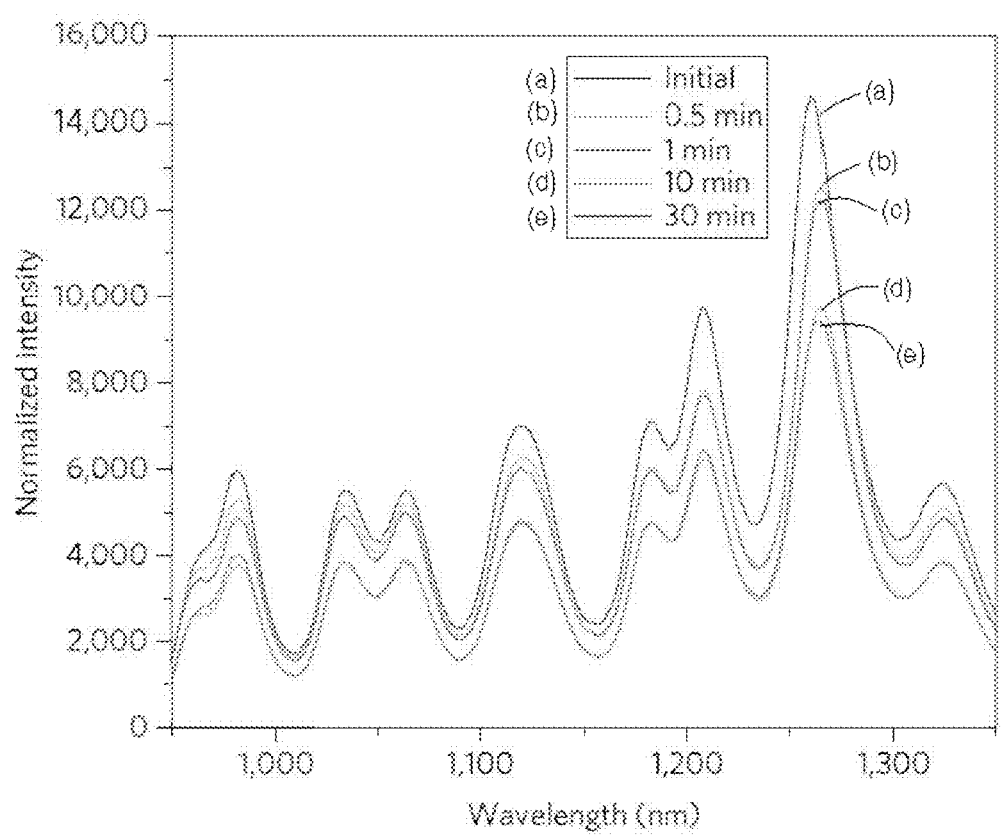

The nIR fluorescence responses of SWNT/DAP-dex and SWNT/SC to NO were investigated. nIR fluorescence spectra were acquired for one second using 785 nm excitation (85 mW). The NO solution was prepared by bubbling pure NO gas through PBS (50 mM, pH 7.4) that had been reoxidized by bubbling argon through it for two hours before the NO introduction. The concentration of NO was measured by a horseradish peroxidase assay. Each SWNT solution (in PBS, pH 7.4, 50 mM) was also bubbled with argon for two hours to remove dissolved oxygen prior to NO addition. As shown in FIG. 3B, the addition of a NO solution (30 micromolar) to a SWNT/DAP-dex solution leads to quick bleaching of nIR fluorescence, which indicates that rapid NO detection with substantial fluorescence bleaching at a physiological pH is possible on a SWNT/DAP-dex hybrid. However, this distinct transition bleaching of fluorescence was not observed in SWNT/SC, even 30 minutes after the same amount of NO was added to a SWNT/SC solution (FIG. 3C). These results suggest that NO detection by nIR-fluorescence bleaching was mediated by the polymer wrapping around the SWNT.

The effect of SWNT-wrapping molecules on NO detection was further investigated in terms of selectivity and transition bleaching rate. Phenoxy-modified carboxymethylated dextran (PhO-dex) was synthesized, which does not include amine and amide groups. The SWNTs were resuspended with PhO-dex via dialysis. Next, the fluorescence responses of SWNT/DAP-dex, SWNT/PhO-dex, and SWNT/SC for NO were investigated. The fluorescence intensity was measured as $I/I_o$ (current intensity/initial intensity based on (10.5) SWNT). The fluorescence intensities were measured ten minutes after the addition of a 30 micromolar solution of each analyte (shown on the x-axis of FIG. 4A) in PBS solution (pH 7.4, 50 mM).

Figure 4A:
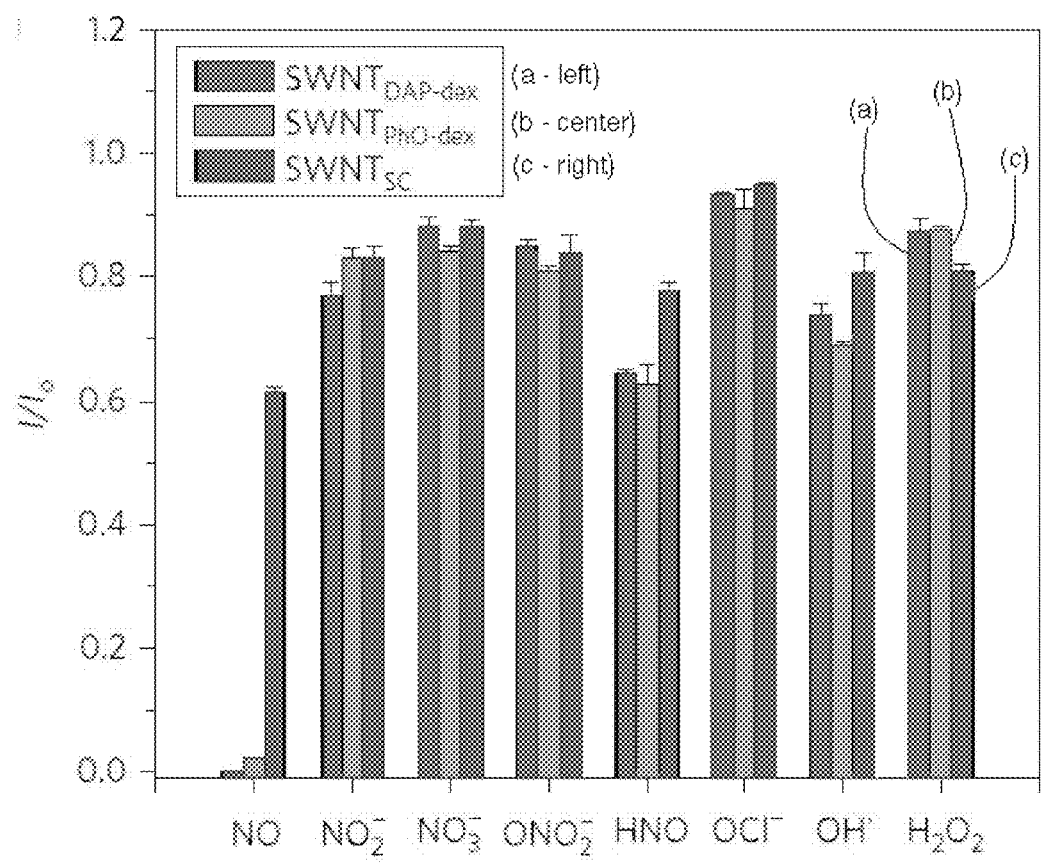
FIGS. 4A-4D include plots of (A) the fluorescence intensity of a plurality of nanosensors, (B) fluorescence bleaching rates of a plurality of nanosensors, (C) fluorescence bleaching rates for NO as a function of emission energy for SWNT/DAP-dex and SWNT/PhO-dex, and (D) the fluorescence intensity of SWNT/DAP-dex as a function of NO concentration, according to one set of embodiments.

As shown in FIG. 4, nIR fluorescence of SWNT/DAP-dex was bleached selectively by NO more than by many other reactive nitrogen and oxygen species present in typical biological systems, including $NO_2^-$, $NO_3^-$, $ONO_2^-$, HNO, $OCl^-$, hydroxyl radicals, and $H_2O_2$ (FIG. 4A). Other oxidative species, such as b-nicotinamide adenine dinucleotide ($NAD^+$) and ferric iron ($Fe^{3+}$), that exist in physiological systems and interfere with the selectivity for NO detection in other systems were also investigated at similar concentrations (30 micromolar) as the tested NO. $NAD^+$ and $Fe^{3+}$ did not bleach the fluorescence of SWNT/DAP-dex appreciably. These results indicate that SWNT/DAP-dex may allow for NO detection in vitro or in vivo.

Figure 4B:
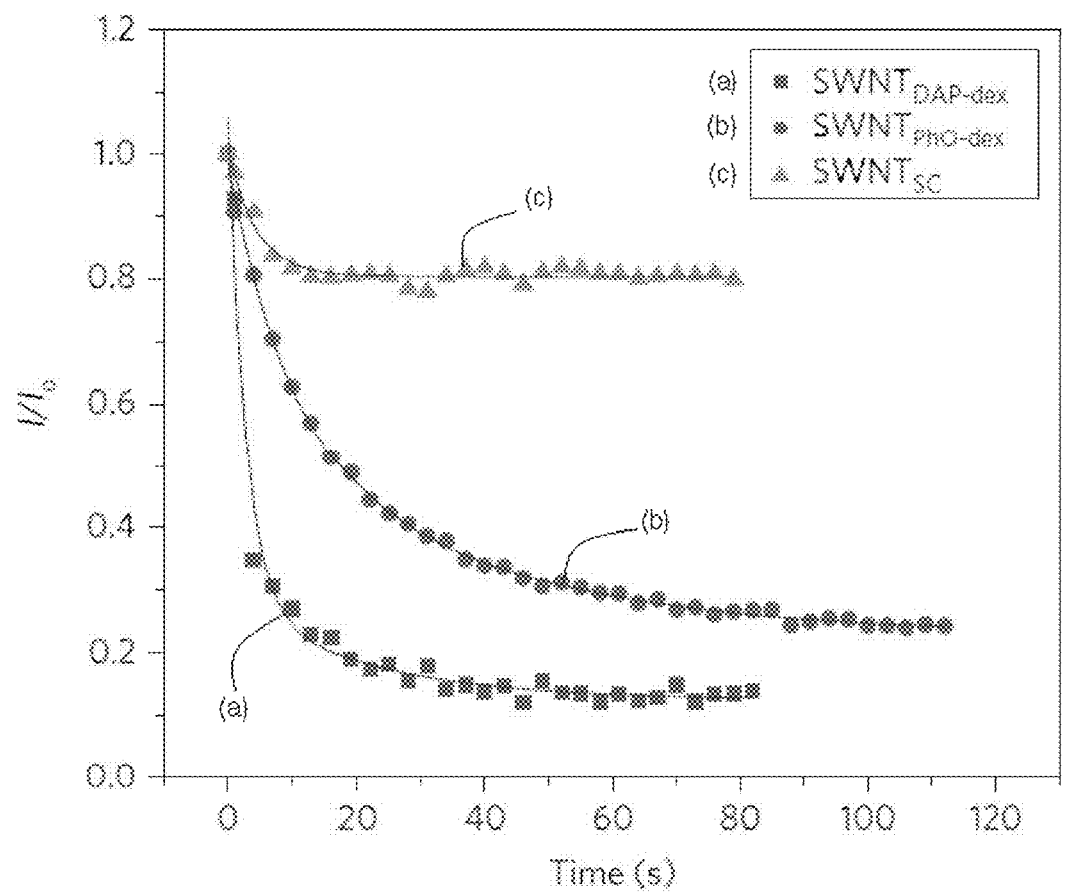
Figure 4C:
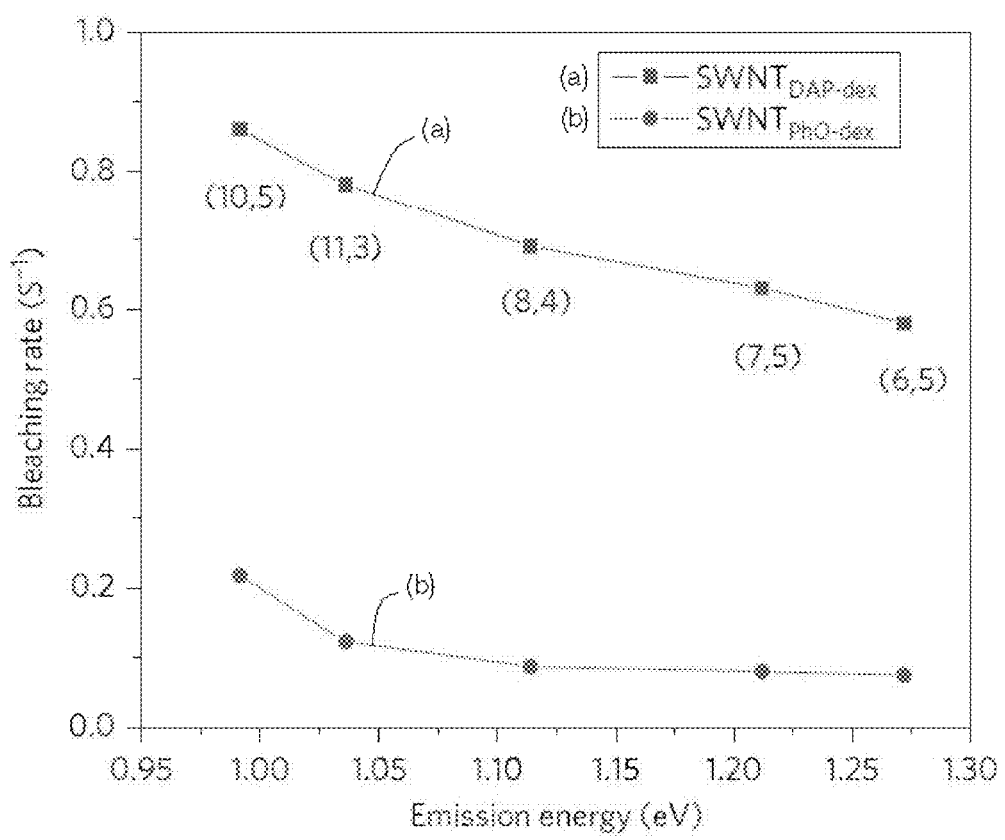
Figure 4D:
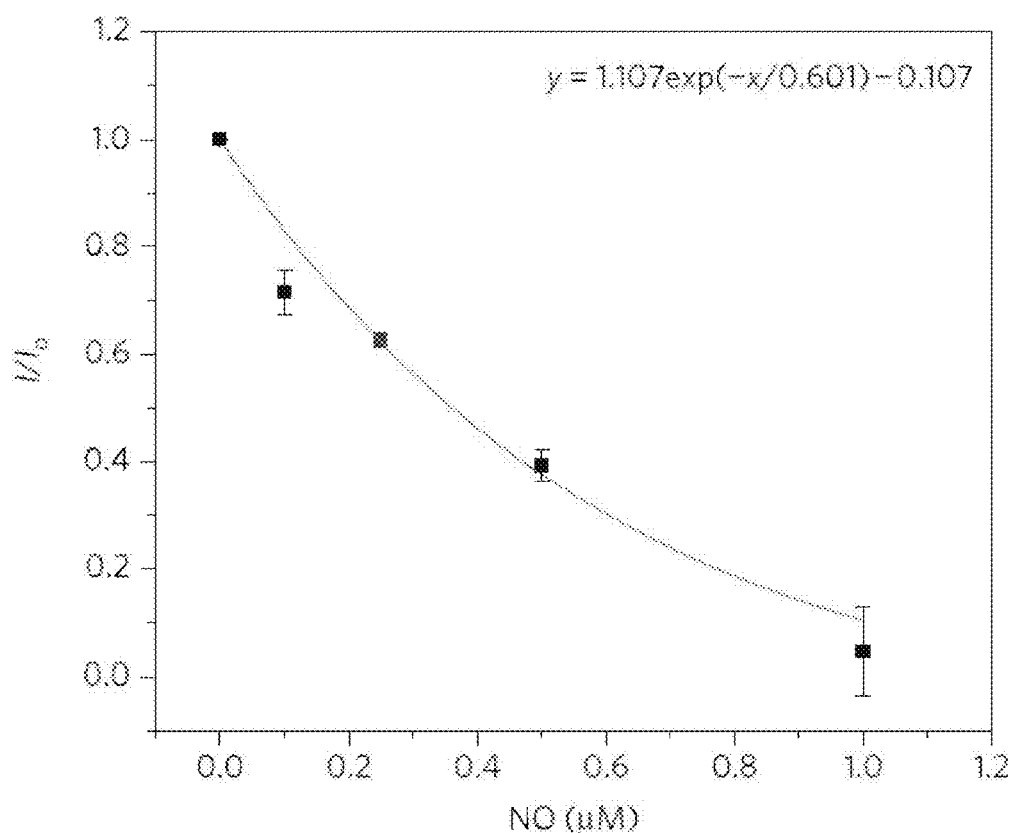

A smaller, less selective, and slower response was observed from SWNTs suspended with Pho-dex (SWNT/PhO-dex). In addition, little selectivity for NO was observed with SWNT/SC. The effect of wrapping functionalities on NO detection was more obviously observed in the transition bleaching rates of nIR fluorescence, as shown in FIGS. 4B-4C, which include plots of fluorescence intensity as a function of time for various nanosensors at a 2.7 micromolar concentration of NO. For these measurements, the intensity of (10.5) SWNT was measured. It was found that the fluorescence of SWNT/DAP-dex was bleached by NO significantly faster than those from SWNT/PhO-dex and SWNT/SC. The bleaching rate of SWNT/DAP-dex ($k_{DAP-dex}=0.856$ $s^{-1}$) was almost fivefold faster than the rates of SWNT/PhO-dex ($k_{PhO-dex}=0.217$ $s^{-1}$) and SWNT/SC ($k_{sc}=0.204$ $s^{-1}$). Also, the fluorescence of SWNTs with small bandgap decayed faster than that of those with large bandgaps (FIG. 4C). Not wishing to be bound by any theory, this may have been because the difference in the gap between the valence band and the LUMO of NO is greater for the former than for the latter. This indicated that the DAP-dex wrapping around the SWNTs was responsible for the selectivity of and rapid response to NO, both of which are useful for the real-time and immediate detection of NO valuable in determining the temporal distribution of NO in biological systems. FIG. 4D includes a plot of fluorescence intensity (based on (10.5) SWNT) as a function of NO concentration, measured ten minutes after the addition of each NO solution. The error bars in FIG. 4D were determined from the mean and standard deviation. The smallest concentration of NO detected using SWNT/DAP-dex was 100 nM (FIG. 4D). However, based on a calibration curve from FIG. 4D, the concentration at three times the noise value for a typical experiment with a signal-to-noise ratio of seven was 70 nM of NO.

Figure 5A:
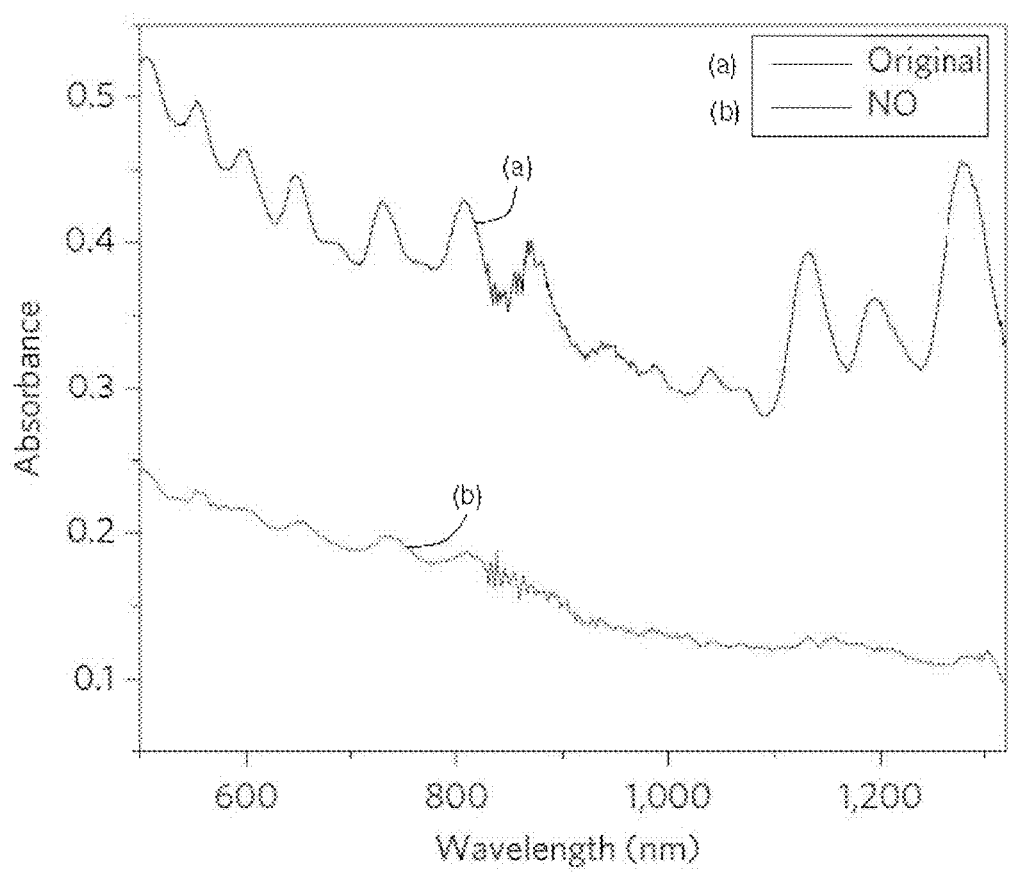
FIGS. 5A-5D include (A) absorption spectra of SWNT/DAP-dex after the addition of 30 micromolar NO solution, (B) Raman spectra of SWNT/DAP-dex after the addition of 30 micromolar NO solution, (C) recovered fluorescence spectra of bleached SWNT/DAP-dex after the addition of NADH (150 micromolar), and (D) fluorescence intensity as a function of time, according to one set of embodiments.
Figure 5B:
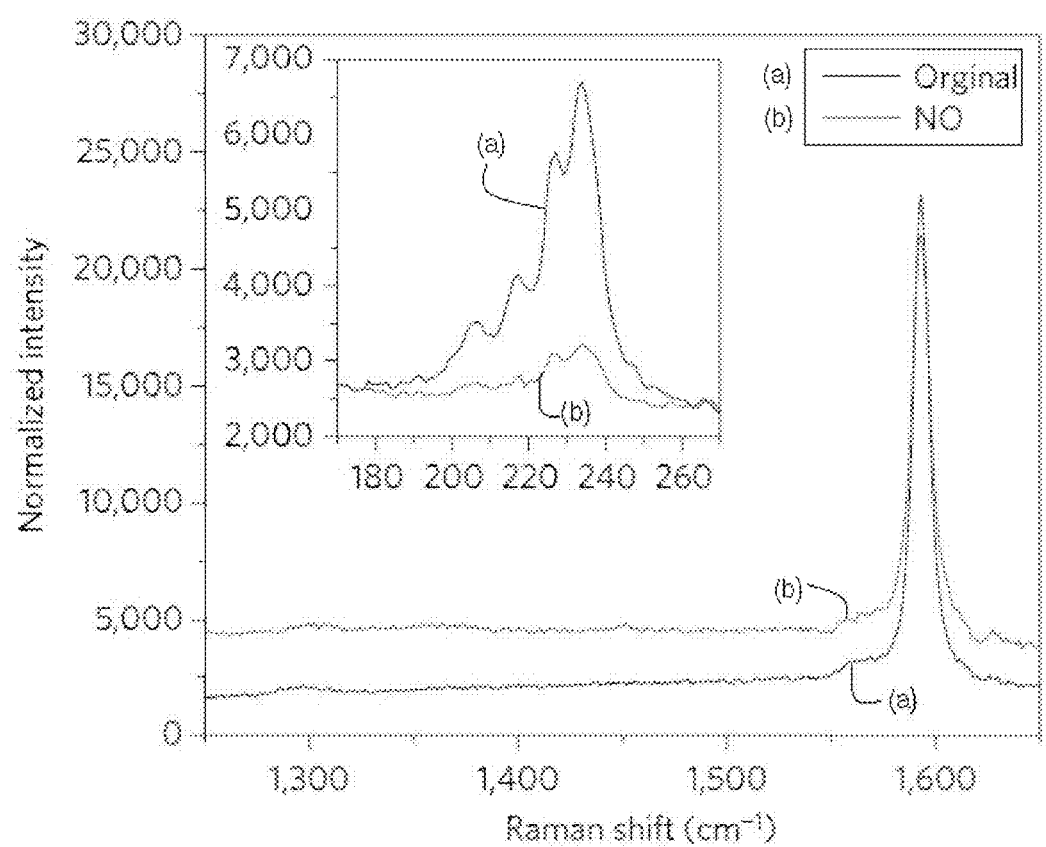
Figure 5C:
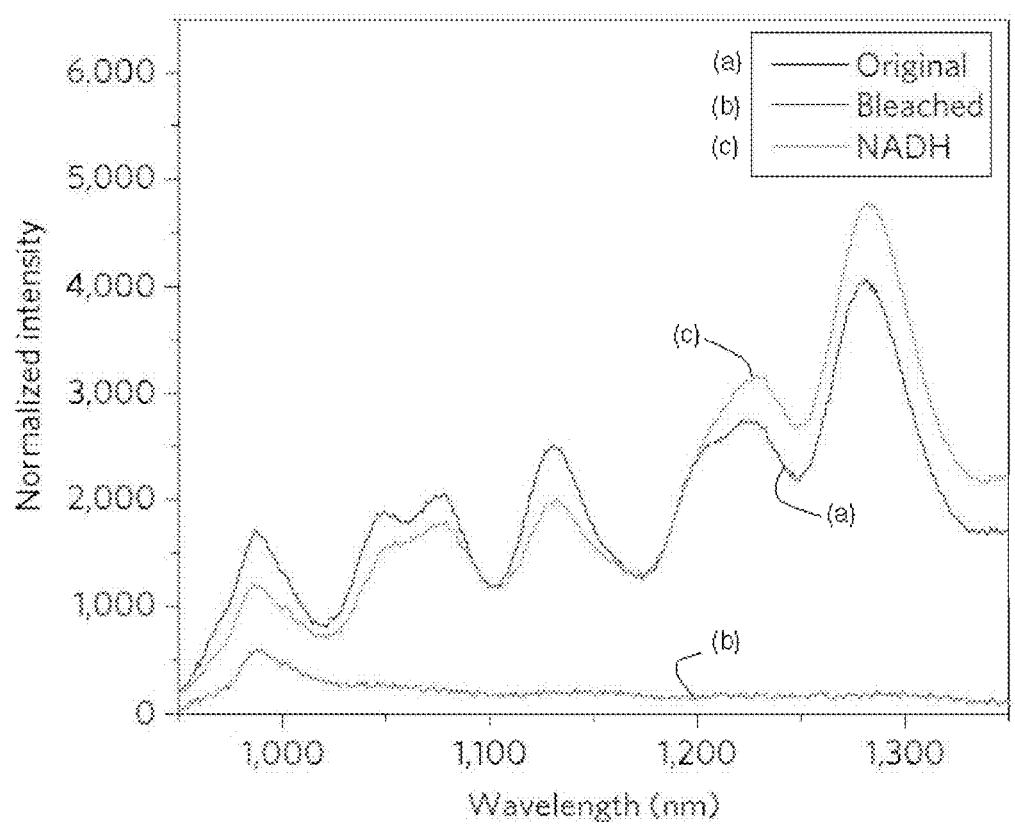
Figure 5D:
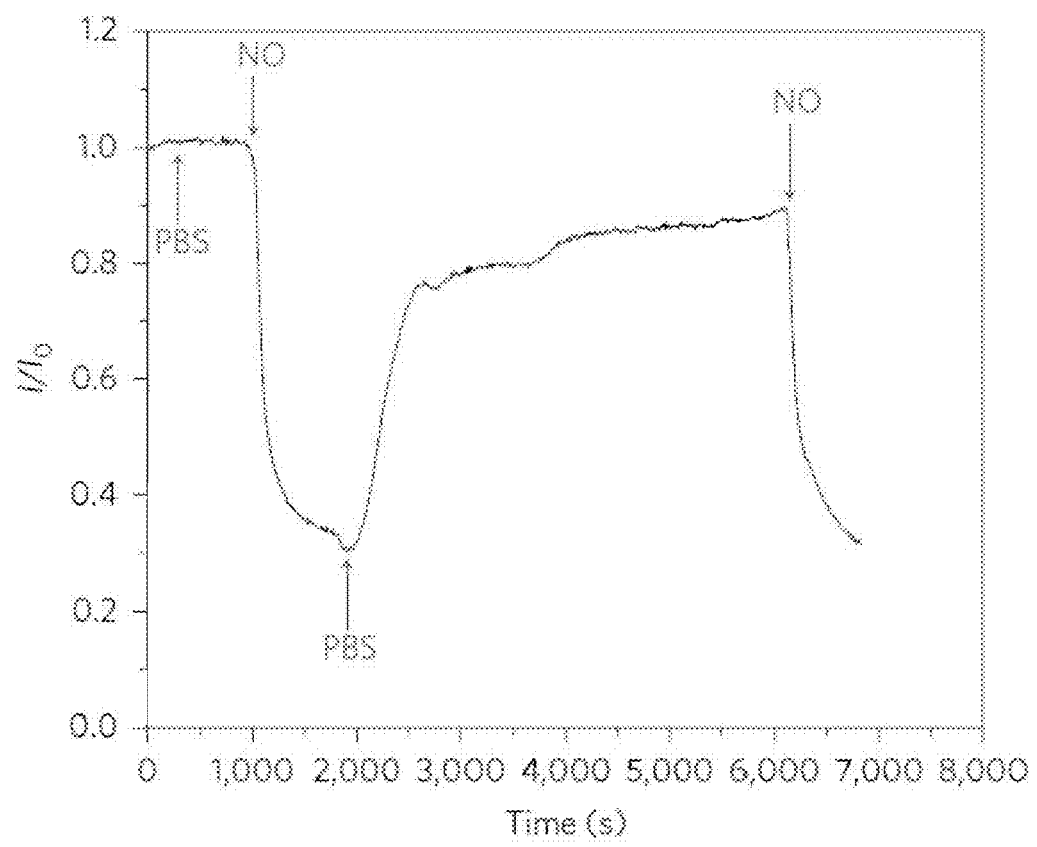

SWNT/DAP-dex at saturation (that is, nIR fluorescence completely bleached by NO) was analyzed to elucidate the bleaching mechanism. As shown in FIG. 5, visible and nIR absorption features of SWNTs changed after the addition of NO. FIG. 5A includes absorption spectra of SWNT/DAP-dex after the addition of 30 micromolar NO solution, showing a large decrease in absorbance for SWNTs with small bandgaps. In particular, the first van Hove transitions almost disappeared (FIG. 5A). The selectivity for nanotubes of small bandgap identified this as a transition photobleaching mechanism. FIG. 5B includes Raman spectra of SWNT/DAP-dex after the addition of 30 micromolar NO solution. The Raman spectra of SWNT/DAP-dex after the addition of NO showed that the intensity of the radial breathing mode (RBM) relative to the G peak decreased (see inset), as expected, through its loss of resonance enhancement. However, an increase in the disorder mode (D) (1,290 $cm^{-1}$) was not observed (FIG. 5B), which indicated that the adsorption of the NO radical was non-covalent and potentially reversible. Further evidence to clarify the bleaching mechanism by NO was obtained by a recovery experiment. As shown in FIG. 5C, which includes recovered fluorescence spectra, the addition of b-nicotinamide adenine dinucleotide (NADH, reduced, 150 micromolar), a reducing agent, to the bleached SWNT/DAP-dex solution resulted in substantially complete recovery of nIR fluorescence, which indicated that the SWNT/DAP-dex optical nanosensor may be reversible for NO detection. Further, nearly complete recovery of visible-nIR absorption of SWNT/DAP-dex was observed after the addition of NADH. Both recoveries were consistent with electron transfer from NADH to the oxidized SWNTs and also supported non-covalent attachment of NO to the SWNT sidewall. Reversible detection was evaluated by attempting to dialyze out NO adsorbed on or around SWNTs. FIG. 5D includes a plot of fluorescence intensity (based on (10.5) SWNT) as a function of time. As shown in FIG. 5D, the bleached fluorescence was restored after simply removing NO from SWNT by dialysis, which indicated that NO detection was reversible. The restoration occurred at the diffusion limit through the dialysis membrane, and it was therefore prohibitively difficult to estimate the desorption rate constant from this experiment. Molecules of comparable size have been found to have desorption rate constants between 600 µs$^{-1}$ and 1,130 µs$^{-1}$ for collagen-wrapped SWNTs (Jin, et al., Nano Lett. 8, 4299-4304 (2008)), which suggests that the NO response was rapid enough for dynamic measurements. All of these results agreed with the mechanism asserted above in which electron transfer from the top of the nanotube valence band to the LUMO of NO causes reversible transition bleaching and nIR fluorescence attenuation. The Raman and nIR fluorescence spectra in FIGS. 5A-5D were acquired for one second using 785 nm excitation.

Biological NO Detection on SWNT/DAP-Dex

Of particular merit is the ability to determine temporally and spatially the production of NO in complex biological systems as a means to study signalling pathways. The capability of the SWNT/DAP-dex optical nanosensor was evaluated for both the real-time and spatially resolved detection of NO within cells. Raw 264.7 murine macrophage cells were grown in Dulbecco's modified Eagles' media (DMEM) that contained 10% (v/v) fetal bovine serum, 100 U ml$^{-1}$ penicillin and 100 micrograms ml$^{-1}$ streptomycin at 37° C. in a humidified atmosphere of 5% $CO_2$. To detect NO produced by iNOS in stimulated Raw 264.7 cells, SWNT/DAP-dex (1 microgram ml$^{-1}$) was added to macrophage cells dispersed in 2 ml DMEM, and then incubated for 12 hours at 37° C. to enable adhesion of the cells and uptake of SWNTs. After washing the cells with PBS several times, LPS (20 ng ml$^{-1}$) and IFN-gamma (20 U ml$^{-1}$) were added into the cells. After incubation for six hours at 37° C., the fluorescence response within the cells was monitored using a nIR fluorescence microscope.

As shown in FIG. 6, macrophage cells that incorporated SWNT/DAP-dex within them (1 microgram ml$^{-1}$) showed bright and photostable nIR fluorescence (FIG. 6A, control). nIR fluorescence generated from the macrophage cells was monitored in real time for 330 seconds, and the NO solution (5 micromolar, PBS) was added to the macrophage cells. The fluorescence images of macrophage cells showed a decrease of fluorescence intensity on the addition of NO, and almost complete bleaching was observed 30 seconds after NO treatment (FIG. 6A), which demonstrated that SWNT/DAP-dex could detect NO within the cells in real time. Even though the nanosensor was based on bleaching (or 'turn-off'), the photostability and small diffusion constant of SWNTs enabled a further analysis that was difficult or impossible using previous organic fluorescence probes. Each pixel was normalized by its corresponding intensity at the start of the experiment. As shown in FIG. 6A (imaging of NO), the result was a spatial dependence on the quenching that reflected real-time gradients in NO concentration within the cell. Some regions clearly quenched before others did, and at different rates. Small molecules encounter barriers to diffusion because of the increased viscosity of dense lipid compared to that of the cytoplasm. Hence, gradients at the cellular level were anticipated. Also, the SWNT/DAP-dex optical nanosensor can enable one to quantitatively track real-time nIR fluorescence within the cells, as shown in FIG. 6B. The nIR fluorescence intensity of SWNT/DAP-dex within the cells suddenly decreased on the addition of NO solution (FIG. 6B), with a detection of down to approximately 200 nM of NO within the cells. In a control experiment, Raw 264.7 macrophage cells that incorporated SWNT/DAP-dex within them were monitored in the absence of NO for ten minutes (FIG. 6A, control). Bright nIR fluorescence of SWNT/DAP-dex within the macrophage cells was still observed without photobleaching during laser irradiation for ten minutes. This was more clearly demonstrated in the quantitative tracking of fluorescence intensity (FIG. 6B, control), which indicated that the fluorescence bleaching was caused by NO production in the macrophage cells.

Next, the ability of SWNT/DAP-dex to detect NO spatially within macrophage cells was investigated by measuring the fluorescence in each cell or in a different region of a single cell. The degree of fluorescence bleaching by NO varied among the cells. The overall fluorescence from three individual cells was bleached by approximately 40%, 28% and 20% after the addition of NO. Moreover, differences in fluorescence bleaching in different regions of the same cell could be distinguished. Quantitatively, the one region of the cell was bleached by 30% while another part of the same cell was bleached by 65%. There was little or no correlation of photoluminescence intensity with SWNT concentration; therefore, the nanosensors should be able to resolve gradients in NO concentration present in different compartments of the same cell.

Figure 6A:
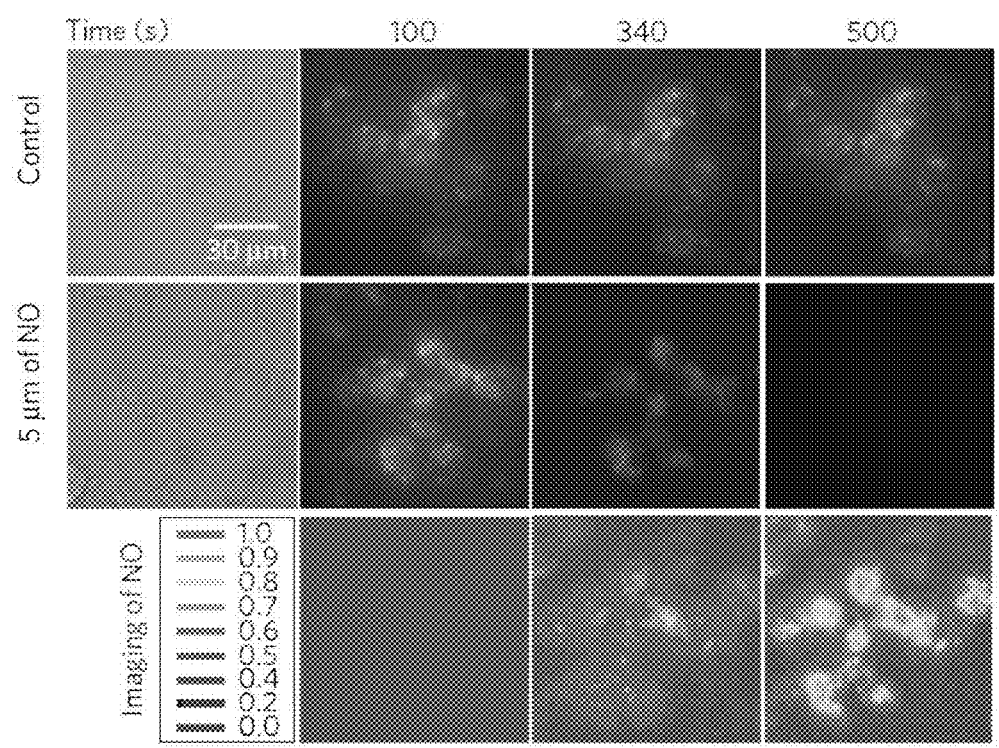
FIGS. 6A-6E illustrate (A) nIR fluorescence images and direct NO mappings of Raw 264.7 cells incorporating SWNT/DAP-dex before and after NO addition, (B) real-time tracking of nIR fluorescence response within Raw 264.7 cells for solutions of NO (5 and 0.5 micromolar), (C) nIR fluorescence response to NO produced by iNOS in Raw 264.7 cells stimulated with LPS (20 ng ml$^{-1}$) and IFN-gamma (20 U ml$^{-1}$), (D) average fluorescence intensity from each cell region responding to NO produced by iNOS in Raw 264.7 cells stimulated with LPS and IFN-gamma, and (E) a mouse placed on the optical stage of a nIR fluorescence spectrometer and fluorescence response to NO (60 micromolar) within the mouse, according to one set of embodiments.
Figure 6B:
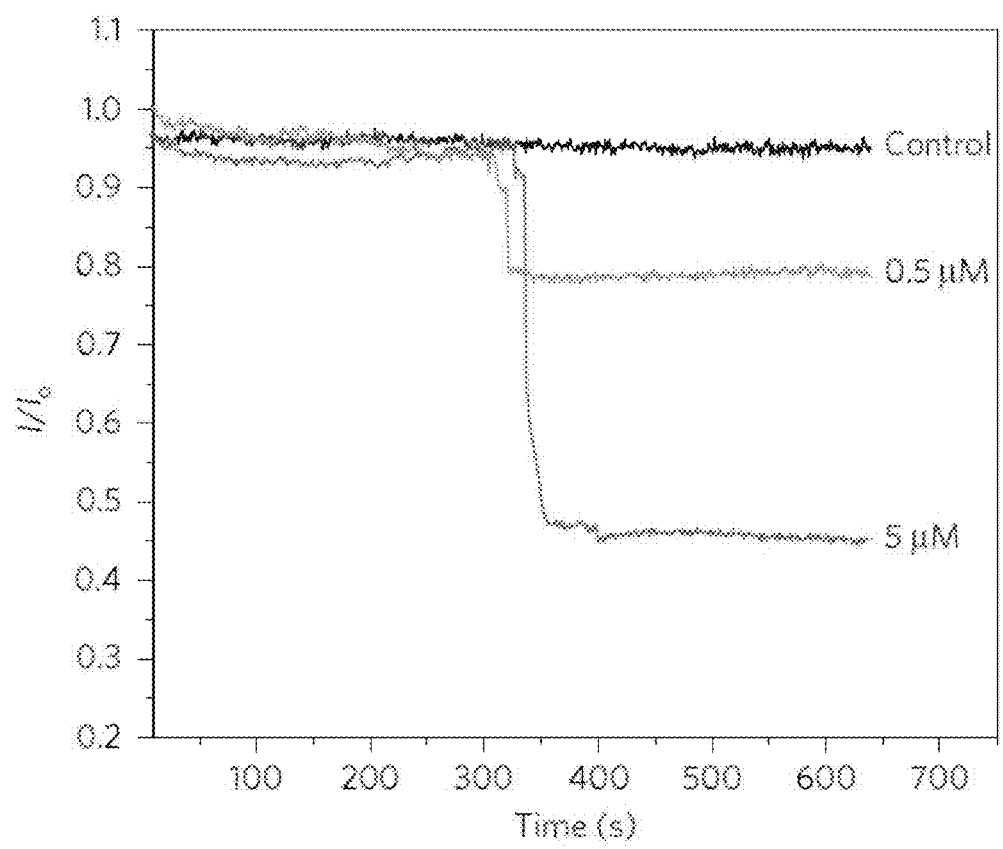
Figure 6C:
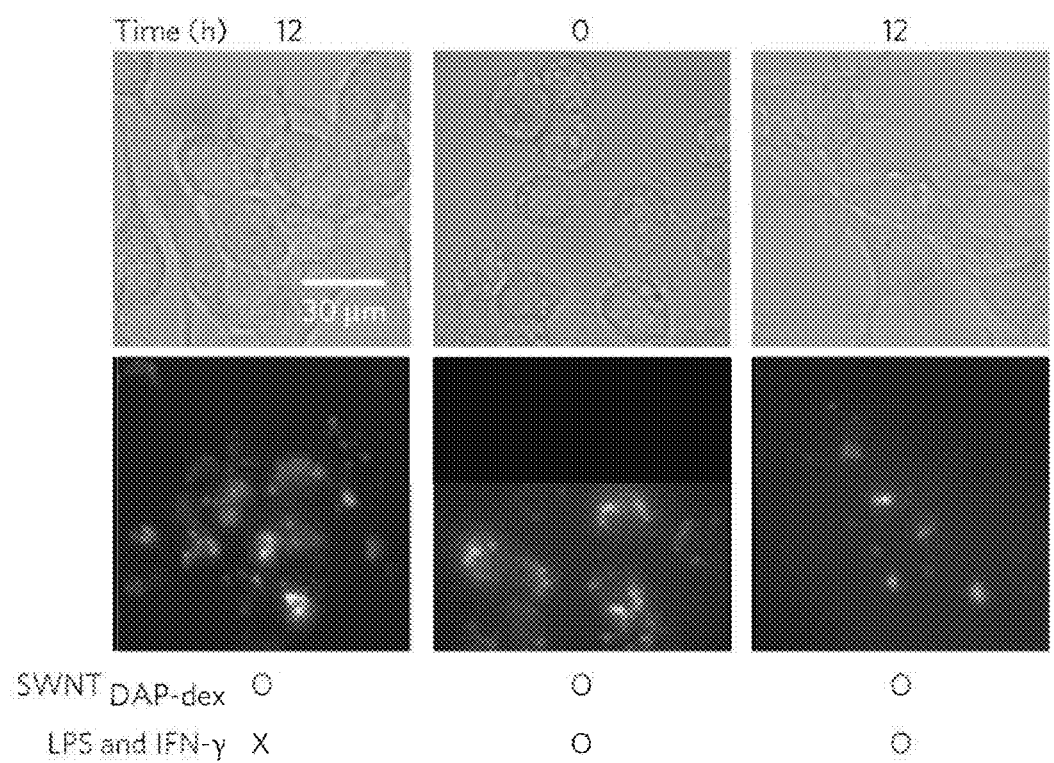
Figure 6D:
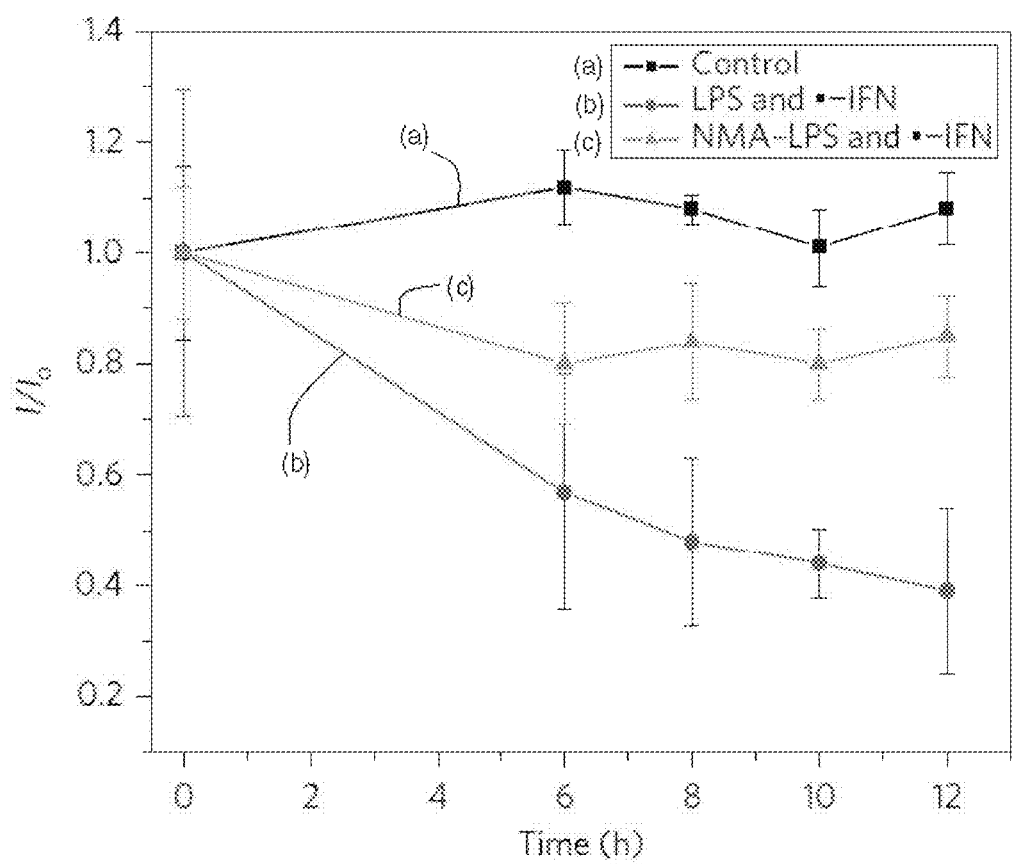

In macrophage cells, it is well known that NO is produced by iNOS. Thus, the detection of time-dependent NO production by Raw 264.7 murine macrophage cells stimulated with lipopolysaccharide (LPS) and interferon-gamma (IFN-$\gamma$) using a SWNT/DAP-dex optical nanosensor was investigated. After macrophage cells had been incubated with SWNT/DAP-dex (1 microgram m$^{-1}$) for 12 hours at 37° C. and washed with PBS, they were treated with LPS (20 ng m$^{-1}$) and IFN-$\gamma$ (20 U m$^{-1}$). After incubation for six hours, the nIR fluorescence response was monitored at intervals of two hours. As shown in FIGS. 6C-6D, the average fluorescence of each cell successively and slowly decreased over 12 hours post activation. The fluorescence bleaching response for Raw 264.7 cells pretreated with $N^G$-methyl-L-arginine (2 mM), a known inhibitor of iNOS that attenuates NO production, became weaker on LPS and IFN-$\gamma$ addition. The fluorescence bleaching was not observed for Raw 264.7 cells that incorporate SWNT/DAP-dex without LPS and IFN-$\gamma$ stimulation. The average fluorescence intensity was almost constant for the 12-hour period of the experiment in non-activated Raw 264.7 cells (FIGS. 6C-6D). These results demonstrated that SWNT/DAP-dex allowed the detection of NO produced by iNOS in Raw 264.7 macrophage cells.

Figure 6E:
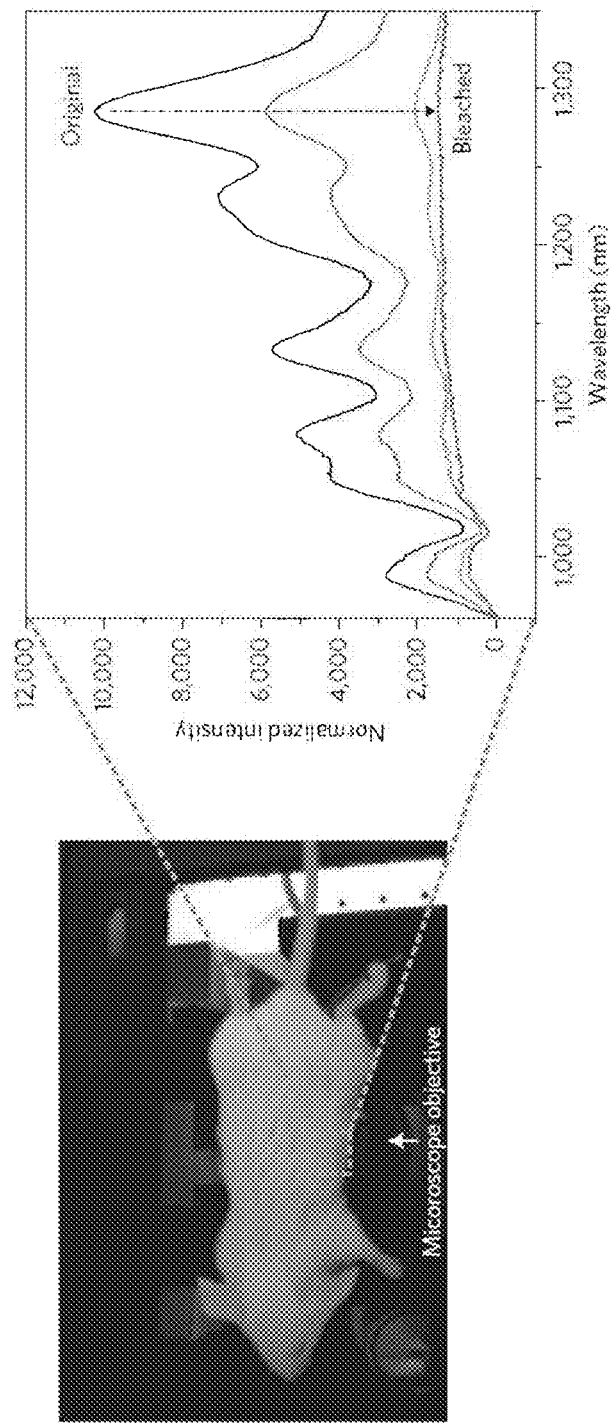

The potential for the in vivo detection of NO using SWNT/DAP-dex (FIG. 6E) was also investigated. A dialysis membrane loaded with a SWNT/DAP-dex solution was inserted into a slit in the abdomen of a $CO_2$-asphyxiated mouse. After imaging, a NO solution (60 micromolar) was injected in the region of the slit and the fluorescence response was monitored in real time. As shown in FIG. 6E, the nIR fluorescence was able to penetrate through tissue with a relatively high signal-to-noise ratio. Ten minutes after NO injection, the fluorescence of SWNT/DAP-dex was bleached completely. The experiment demonstrated that the major barriers to optical detection of NO in vivo (e.g., tissue penetration, scattering, and autofluorescence) can be overcome using the nanosensors described herein.

Cytotoxicity of SWNT/DAP-Dex on Raw 264.7 Cells

To evaluate the cytotoxicity of SWNT/DAP-dex, the LIVE/DEAD viability and cytotoxicity assay that provides simultaneous determination of live and dead cells with two probes (See Pike, C. J., et al., J. Biol. Chem. 270, 23895-23898 (1995)) was carried out on Raw 264.7 cells after 12 hours of incubation with SWNT/DAP-dex (1 and 2 micrograms ml$^{-1}$). According to the results of the test, the survival and death rates of macrophage cells were 100±19% and 2.4±19%, respectively, within the margins of error of the control samples. This indicated that SWNT/DAP-dex was clearly not cytotoxic at all the tested concentrations.

The ability of SWNT/DAP-dex to induce an activation response in Raw 264.7 cells without LPS and IFN-$\gamma$ was also investigated. Such a response would make the use of the nanosensor in vitro and in vivo difficult in this capacity, because the probe itself would stimulate NO from the host immune system. The Griess assay was used to independently assess the activation of cells exposed to SWNT/DAP-dex, and none were detected. The lack of cytotoxicity and immunogenicity is promising for practical applications of the nanosensor.

Nanotube Nanosensor Mechanism

One possible hypothesis was that the lone-pair electrons on the amine moieties of the polymer n-doped the nanotube, which made it electron-rich for direct charge transfer to NO. It would appear that the nanotube surface itself had a basal response to NO, as demonstrated using the sodium cholate and PhO-dex controls. The DAP groups, then, may have increased the rate of NO detection and selectivity by donating lone-pair electrons in the diamino groups to the SWNTs, which may have conferred an increase in electron density. This charge-transfer n-type doping of SWNTs can lead to increases in the Fermi level and the electrochemical potential from the LUMO of NO. This could accelerate the electron transfer from SWNTs to NO. The preferential reaction of NO through these diamine sites may explain both the increase in rate and selectivity of NO for SWNT/DAP-dex. This also may illustrate that engineering a SWNT nanosensor in this manner requires suppression of any non-selective response from interfering molecules.

The hypothesized mechanism suggests how one may use SWNTs rationally to design nanosensors for other analytes. Not wishing to be bound by any theory, there are apparently two components to the selectivity induced by the polymer: its steric adsorption and its redox properties on the nanotube. It is currently difficult to determine how a polymer adsorbs to create a selective gap or binding site for a molecule such as NO. Thus, the responses to NO and a host of other probe molecules can be used to probe the adsorbed phase. The adsorbents may be characterized, for example, through molecular penetration experiments. The dextran backbone alone generally does not adsorb onto SWNTs; phenylation of the dextran can lead to adsorption. The phenyl ring has a favorable energy configuration in the pi-stacking position, and the rings can tether a dextran backbone to the SWNTs with dextran-facing solution. The addition of the diamine can do two things. It can n-dope the carbon nanotube, which can raise the Fermi level, as for many other amine species. It can also perturb the structure of the dextran polymer, altering its conformation to yield a binding site on the nanotube that is more favorable for NO binding. The best evidence for this is simply the selectivity towards NO, which increases dramatically with diamine addition. This effect is not what the diamine construct does for conventional NO nanosensors.

Example 2

In this example, a photoluminescent nanosensor comprising a polynucleotide and a carbon nanotube is described. The nanosensor included a single-walled carbon nanotube (SWNT) partially encapsulated by a poly $d(AT)_{15}$ DNA oligonucleotide (an oligonucleotide comprising 15 AT base pairs in succession) to form a $d(AT)_{15}$-SWNT nanosensor. The nanosensor in this example exhibited sensitivity to nitric oxide and substantially no other analyte during screening.

Figure 7A:
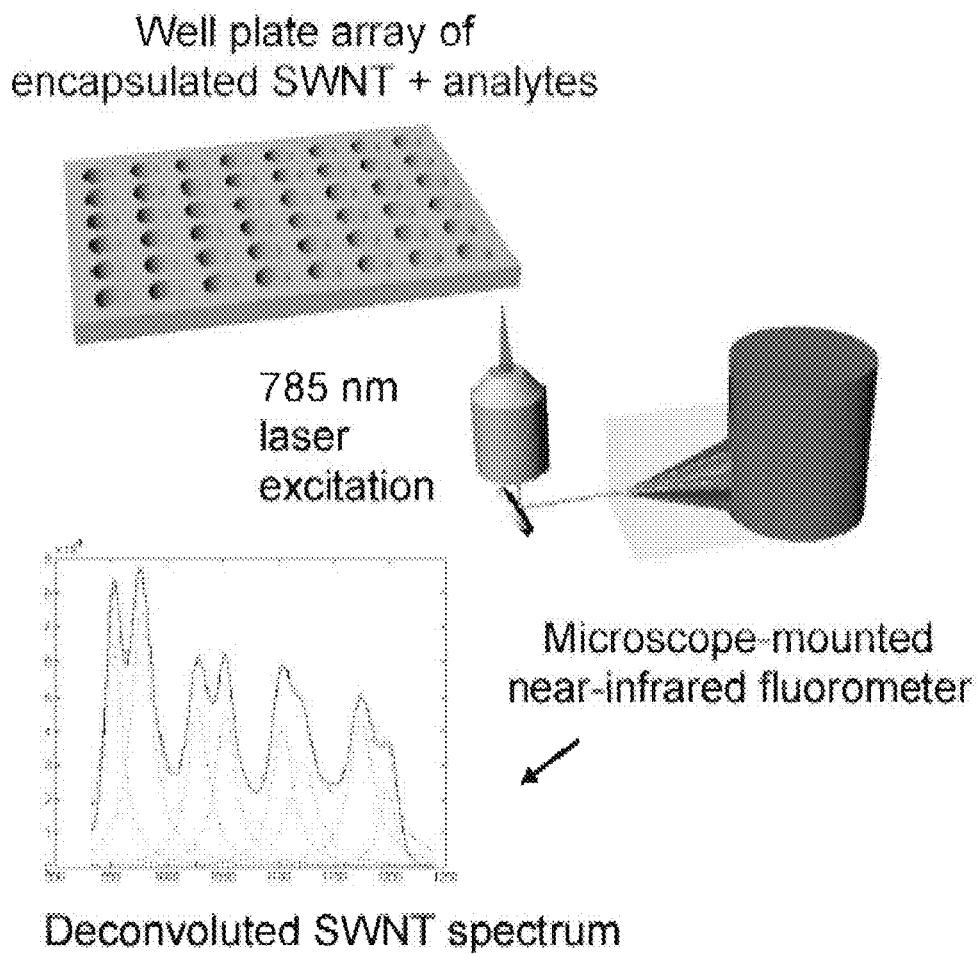
FIGS. 7A-7E include (A) a schematic illustration of a high-throughput assay scheme, and (B-E) responses of various nanotube sensors to a collection of compounds, according to one set of embodiments.
Figure 7B:
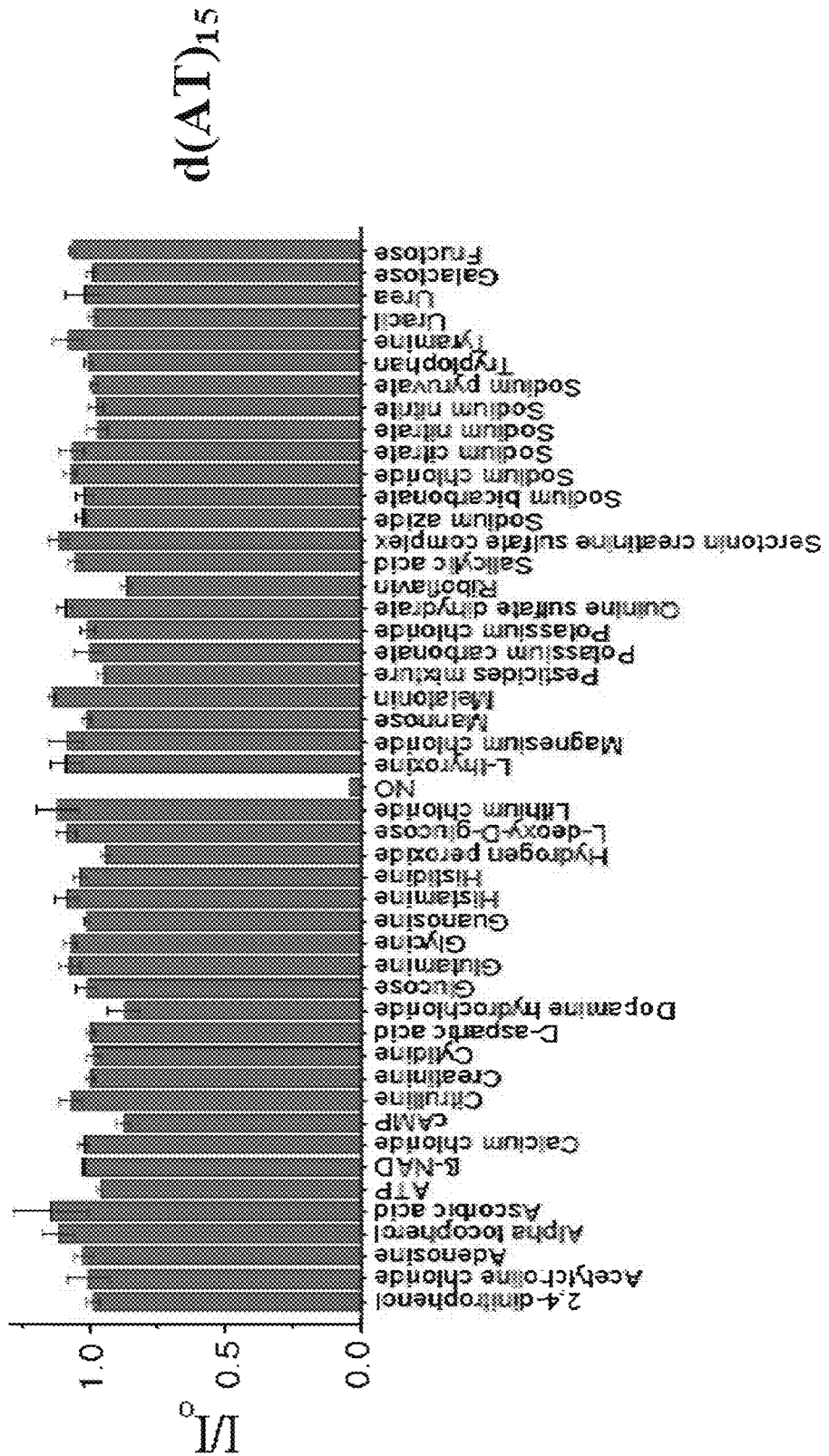
Figure 9A:
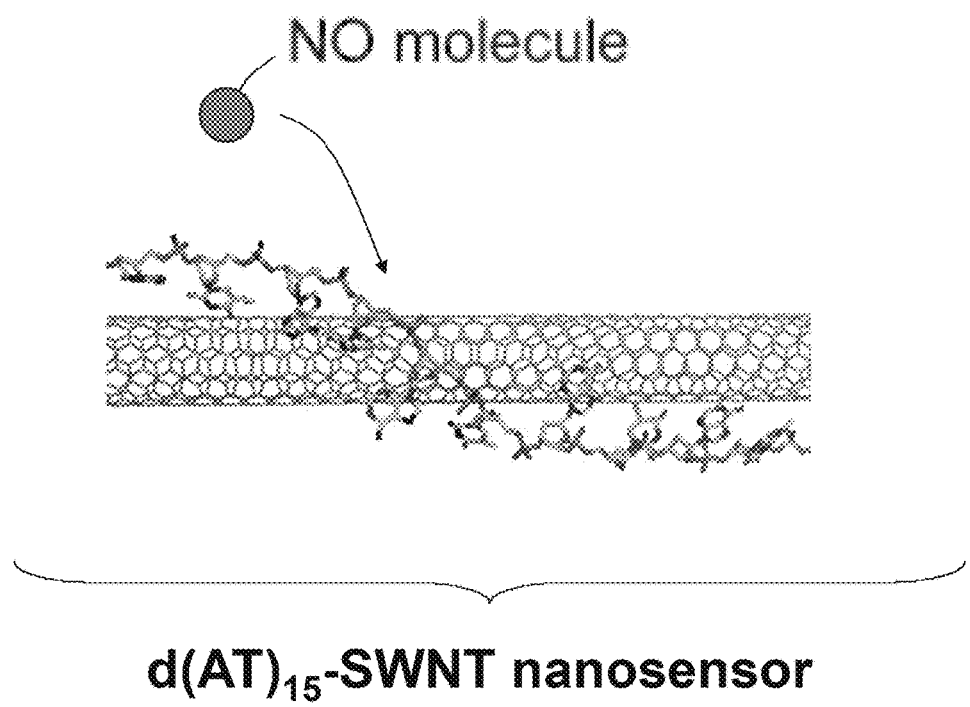
FIGS. 9A-9F include (A) a schematic illustration of NO adsorption on a d(AT)$_{15}$-SWNT complex, resulting in a fluorescence quenching, (B-C) representative fluorescence intensity of a 2×2 pixel spatial binning region on two different individual SWNTs that show B) stepwise quenching and C) stepwise restoration, (D) an exemplary transition density plot (TDP) generated from HMM corresponding to the experiments in B) and C), (E) the algorithm used to correlate transition probabilities between any two distinct states to quenching and de-quenching rate constants, and (F) NO adsorption and desorption rate constants, and equilibrium constants as functions of NO concentration, according to one set of embodiments.
Figure 9B:
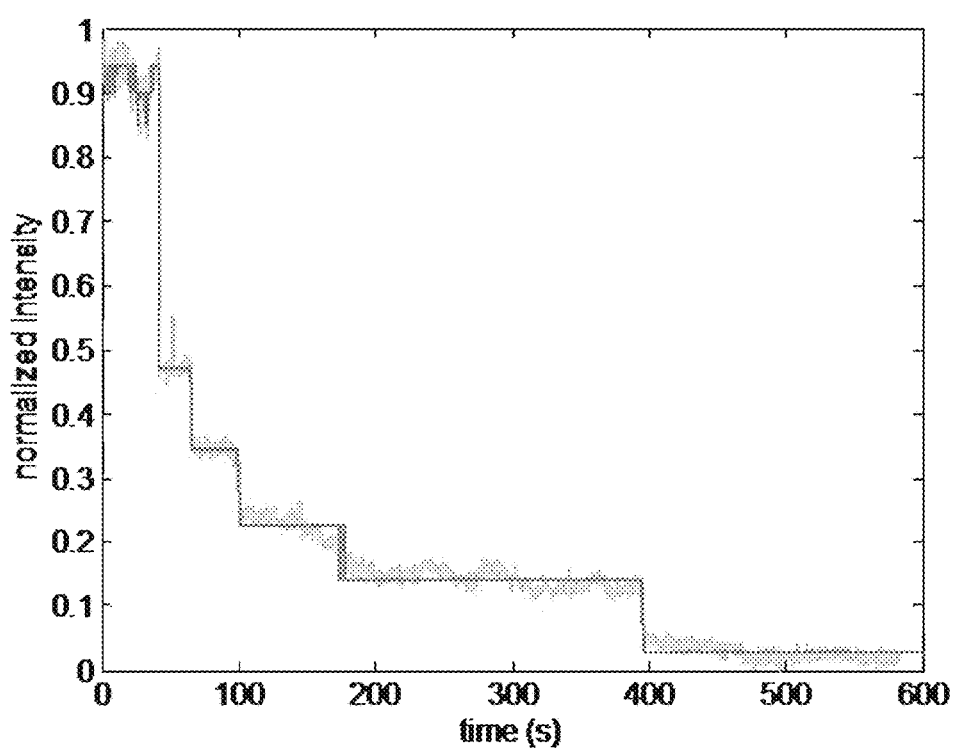
Figure 9C:
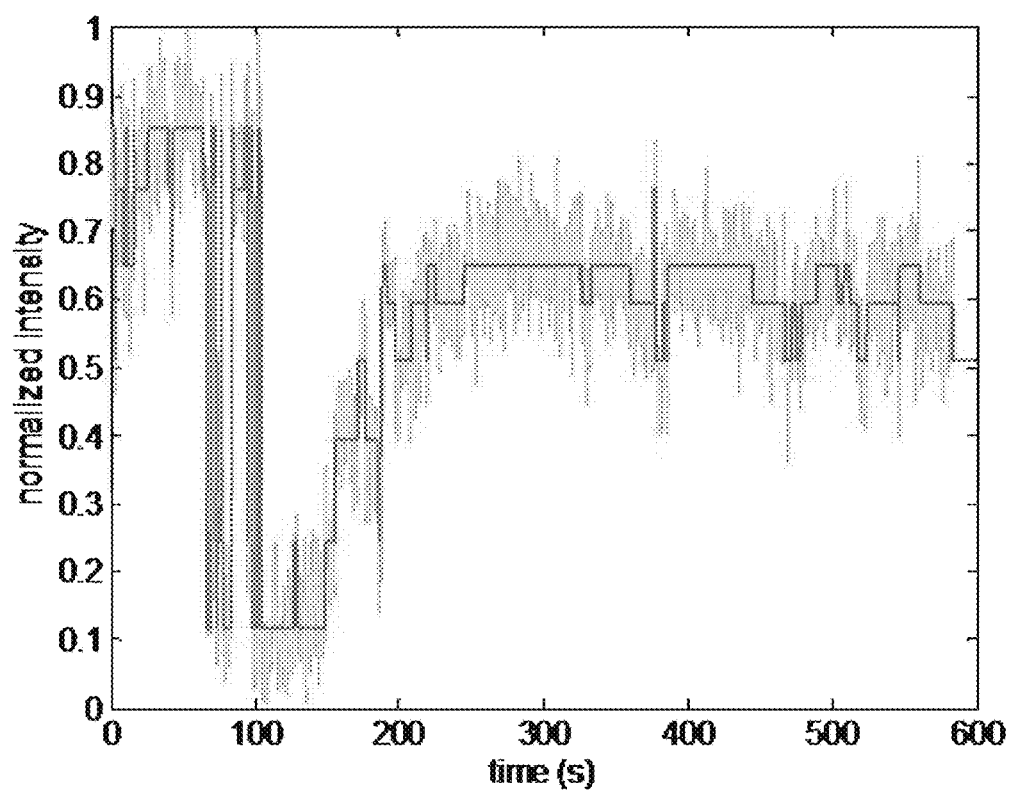

As shown in FIG. 7B, the $d(AT)_{15}$-SWNT nanosensor was screened against the following compounds (listed in order as they appear in FIGS. 7B-7E, from left to right): 2,4-dinitrophenol, acetylcholine chloride, adenosine, alpha-tocophenol, ascorbic acid, ATP, beta-NAD, calcium chloride, cAMP, citruline, creatine, cytidine, D-aspartic acid, dopamine hydrochloride, glucose, glutamine, glycine, guanosine, histamine, histidine, hydrogen peroxide, L-deoxy-D-glucose, lithium chloride, nitric oxide (NO), L-thyroxine, magnesium chloride, mannose, melatonin, a pesticides mixture, potassium carbonate, potassium chloride, quinine sulfate dihydrate, riboflavin, salicylic acid, seratonin/creatinine sulfate complex, sodium azide, sodium bicarbonate, sodium chloride, sodium citrate, sodium nitrate, sodium nitrite, sodium pyruvate, tryptophan, tyramine, uracil, urea, galactose, and fructose. In addition, the nanosensors were screened against creatinine, dopamine, DMSO, ethanol, and methanol, the results of which are not shown in FIGS. 7B-7E. The nanosensors were screened for near-infrared spectroscopic responses. As illustrated in FIG. 7A, the nanosensors were suspended in Tris buffer (20 mM Tris, 100 mM NaCl, pH 7.3) and were placed in a well plate array containing 48 analytes, incubated for 1 hr, and placed on an automated microscope translation stage. The nanotubes were excited by a 785 nm laser and SWNT near-infrared photoluminescence was collected via fluorescence microscope, dispersed in a 250 cm spectrograph, and detected by a 512 pixel InGaAs array. The spectra were deconvoluted into a series of Lorentzian curves; the intensities and center wavelengths were recorded. The resulting outputs are illustrated in FIGS. 9B-9C.

Figure 7C:
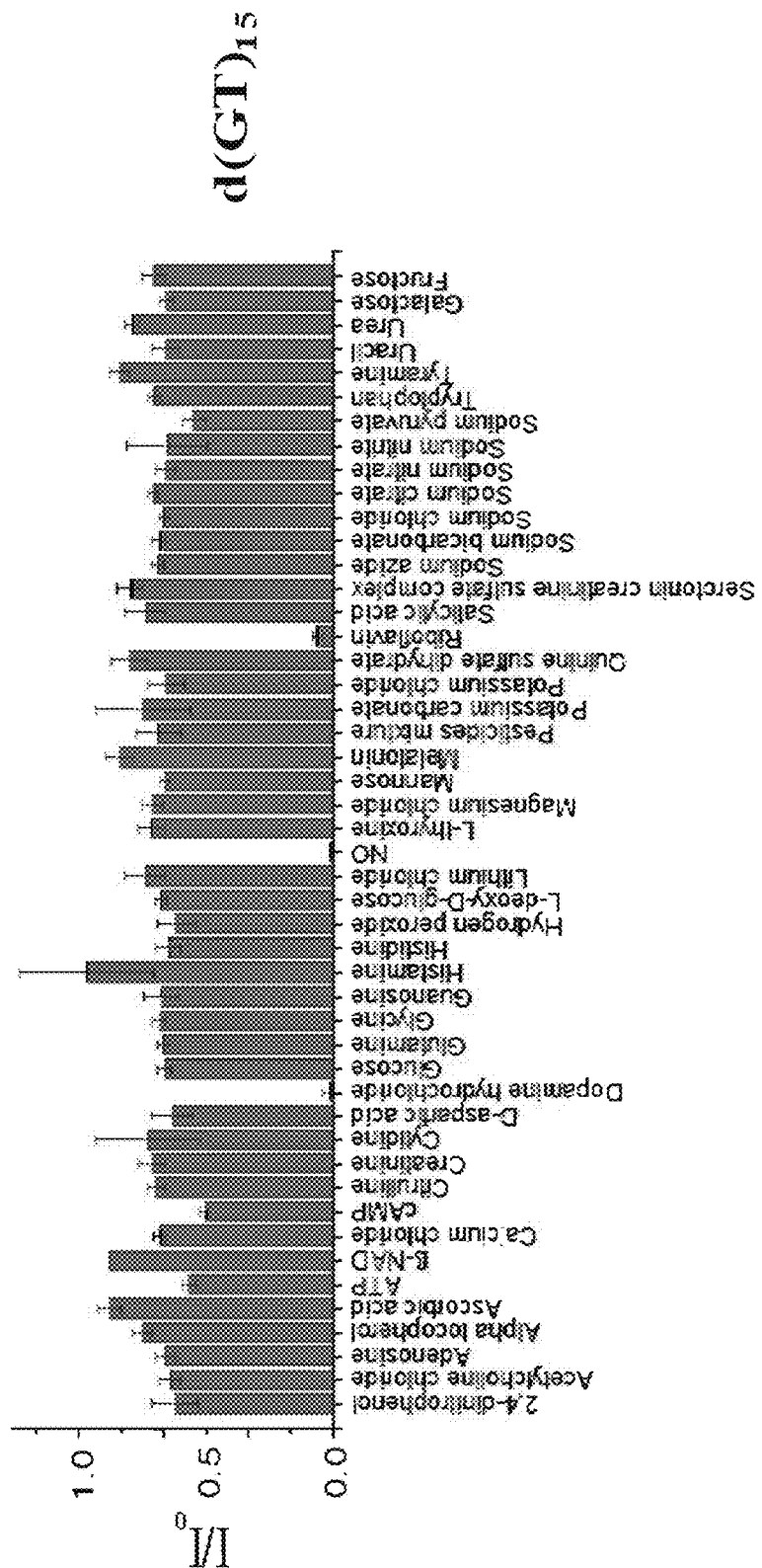
Figure 7D:
Figure 7E:
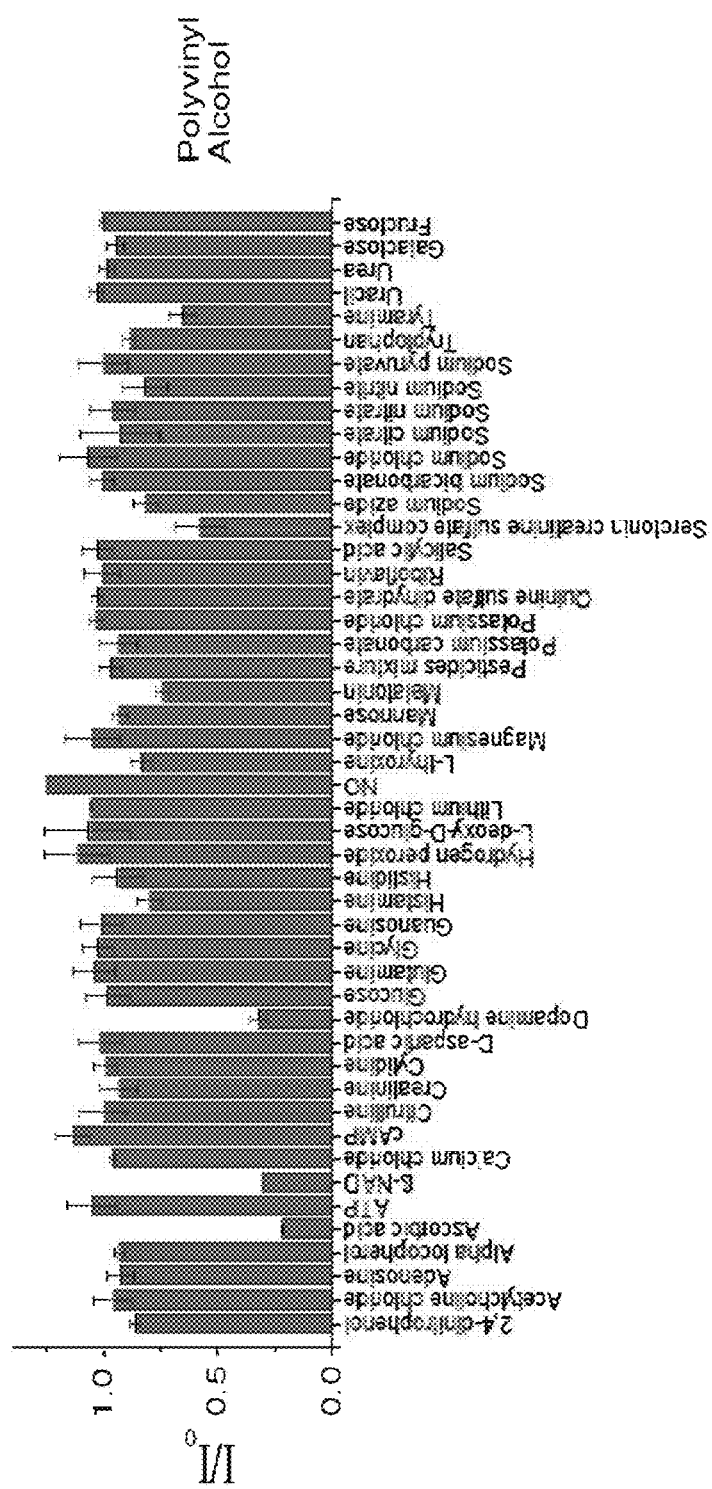

Several polymers were tested including a poly $d(AT)_{15}$ oligonucleotide, a poly $d(GT)_{15}$ oligonucleotide, phenylated dextran, and polyvinyl alcohol, as illustrated in FIGS. 7B-7E. The nanosensor comprising the poly $d(AT)_{15}$ DNA oligonucleotide exhibited sensitivity to NO, but was not sensitive to any other tested analyte (FIG. 7B). The poly $d(GT)_{15}$ sequence responded to dopamine, NO and tyramine (FIG. 7C). The phenylated dextran scaffold exhibited a similar response, with inclusion of some additional amine-baring analytes (FIG. 7D). The poly vinyl alcohol exhibited a substantially complete barrier to nitric oxide, but was sensitive to other neurotransmitters (FIG. 7E).

Example 3

Figure 8A:
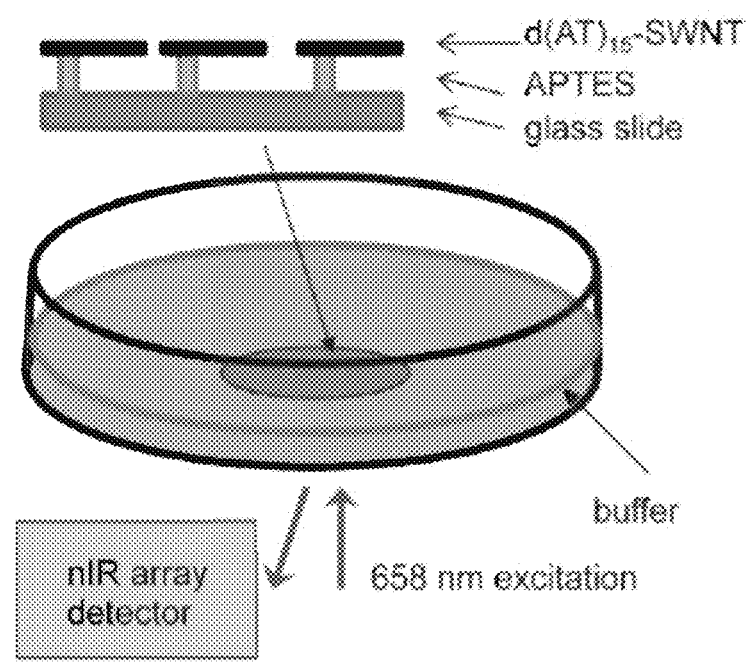
FIGS. 8A-8B include (A) a schematic illustration of an experimental configuration used for single-molecule NO detection, and (B) the fluorescence emission from d(AT)$_{15}$-SWNT, according to one set of embodiments.
Figure 8B:
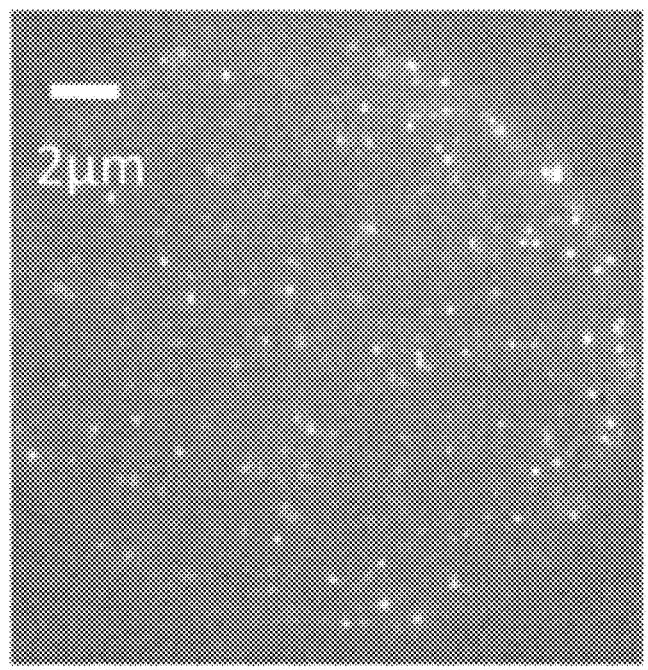

In this example, a photoluminescent nanosensor comprising SWNTs capable of determining single molecule adsorption and desorption of NO molecules is described. In this example, a Petri dish was treated with aminopropyltriethoxysilane (APTES) substrates commonly used for AFM, and buffered by PBS (0.0067 M $PO_4^{3-}$, pH 7.4) (FIG. 8A). Under physiological pH, $d(AT)_{15}$-SWNT adsorbed strongly to APTES through charge-charge interactions, and remained stable (FIG. 8B). Upon laser excitation (658 nm wavelength), $d(AT)_{15}$-SWNT fluoresced at near infrared wavelengths. The emitted light was collected by a 2D InGaAs imaging array (FIGS. 8A-8B). Upon addition of NO, single NO molecule adsorption and desorption events on nanotubes were transduced to a stepwise increase and decrease of SWNT complex fluorescence, as the mobile excitons on the SWNT sidewalls were attacked by the quencher molecule NO. Movies at 200 ms/frame were taken to monitor florescence modulation in real time through the course of 10 min. The image in FIG. 8B was taken with 1 mW laser power at the sample through Alpha Plan-Apo 100×/1.46 oil immersion objective.

Very clear stepwise fluorescence changes from each individual SWNT were observed. Each step was essentially a single molecule event. A stepwise increase (FIG. 9B) indicated single molecule NO adsorption on the SWNT, whereas a stepwise decrease (FIG. 9C) indicated NO desorption from the SWNT. Theoretically, each step should remain the same size (or height). However, if the NO adsorption rate is faster than the sampling rate (5 s$^{-1}$ in this example), several quenching events could happen in a period of time short enough that only bigger steps would be observed, and the step size of those bigger steps could be essentially multiples of a single small step.

Hidden Markov Modeling (HMM) was used to correlate single molecule adsorption and desorption events to rate constants and also to the concentrations of the molecule, as described in Jin, H. et al., *Nano Lett.* 2009, 8, (12), pp 4299-4304, which is incorporated herein by reference in its entirety. Using this algorithm, real quenching and desorption events could uncovered by removing the little noise from the relatively clean data in FIGS. 9B-9C.

Figure 9D:
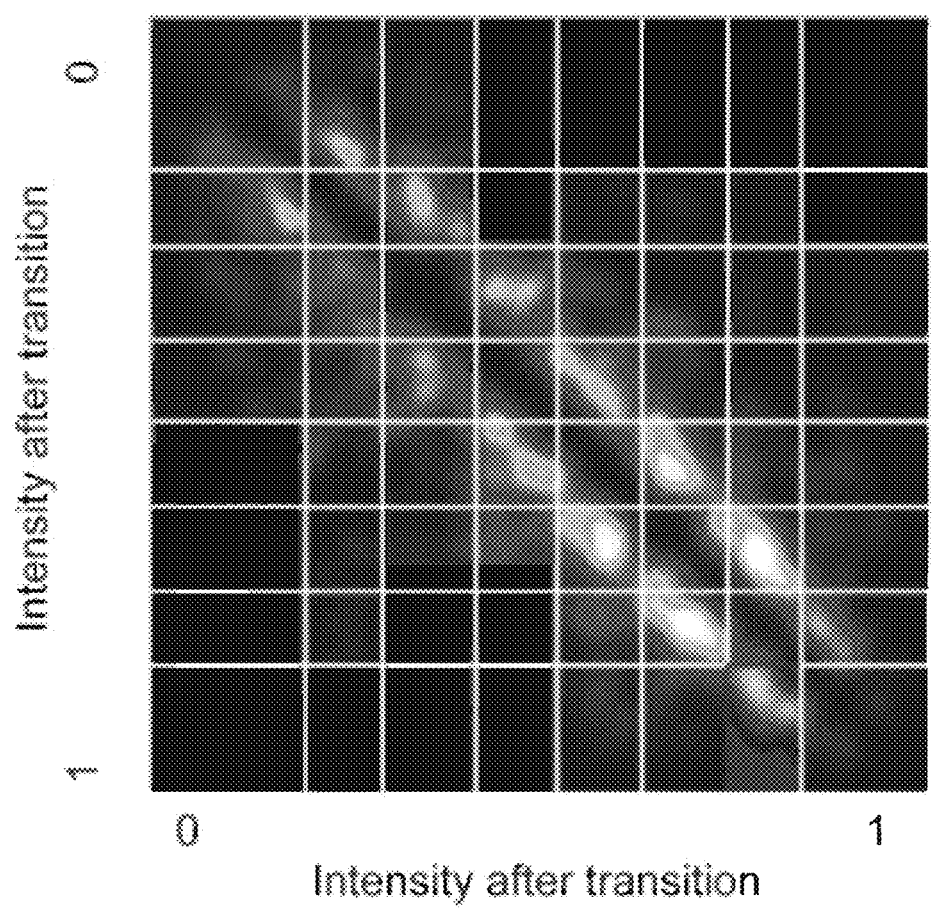
Figure 9E:
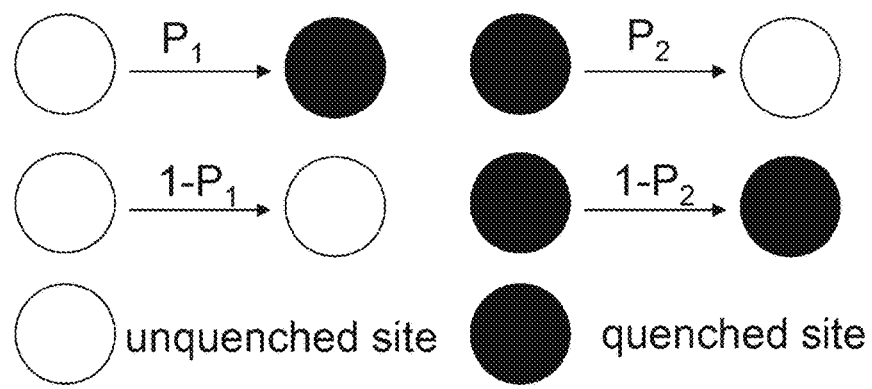
Figure 9F:
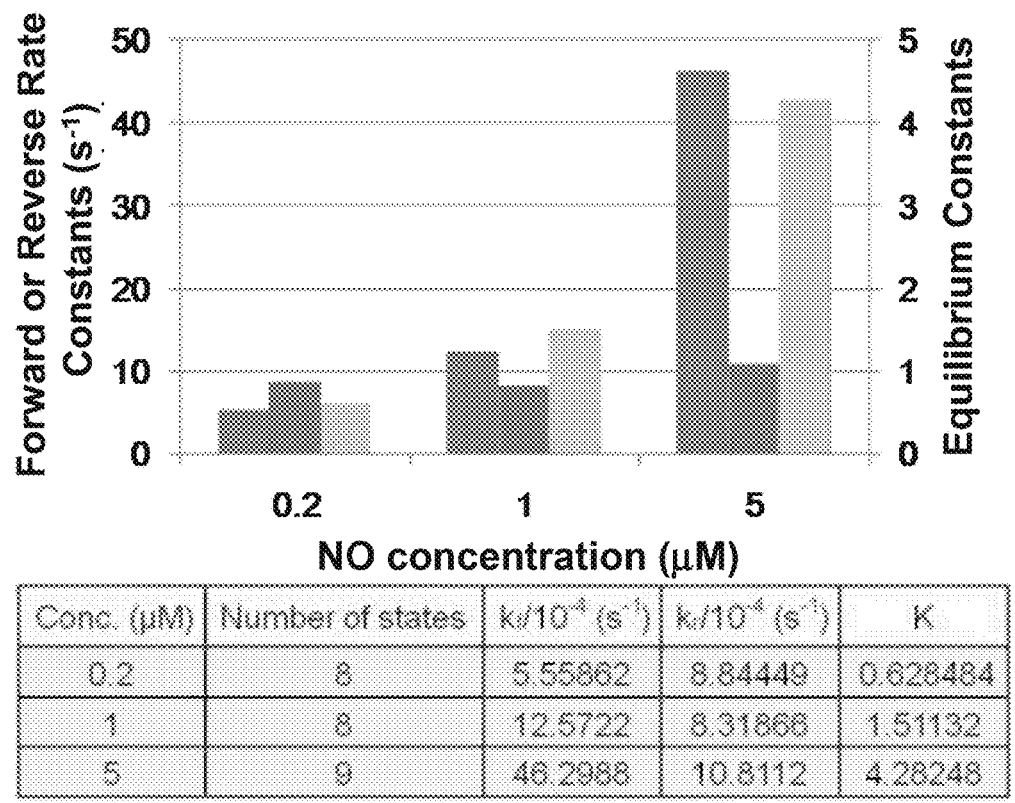

Rate constants and concentrations of NO were correlated to transition probabilities given by HMM. A transition density plot (TDP) was used to further analyze the modeling results from HMM by populating frequent transitions between states. It was found that the $d(AT)_{15}$-SWNT nanosensor exhibited 7 quenchable sites, giving rise to 8 different states (FIG. 9D), where 0 represents the lowest state and 1 represents the highest state. Transition probabilities between any given states were obtained from the HMM and TDP, and further used to calculate single site transition probability. By using Gillespie's theory (*J. Phys. Chem.* 1977, 81, (25), pp 2340-2361, which is incorporated herein by reference in its entirety), rate constants were calculated from single site transition probabilities (FIG. 9E). The results indicated that the NO desorption rate was concentration independent, but the NO adsorption rate increased as the concentration of NO increased (FIG. 9F). The relationship between rate constants and NO concentration can be used to calibrate the nanosensor for detection of low concentrations of NO.

Example 4 ss$(AT)_{15}$ DNA oligonucleotides wrapped SWNT ($AT_{15}$-SWNT) were prepared by suspending HiPCO SWNT in $AT_{15}$-containing 0.1 M NaCl solution. Individually suspended SWNT was confirmed through atomic force microscopy (AFM). In addition, molecular dynamics simulation on the $AT_{15}$-SWNT indicated that bases stacked on the sidewall of the SWNT, while the sugar-phosphate backbone extends away from the surface, which yields the colloidally stabile SWNT suspension. This is consistent with experimental evidence including AFM [26-27] and optical absorption[28] data and simulation results[29-33] reported to date that through pi-pi □ stacking of base on the sidewall of the SWNT and exposing the phosphate back bone to water, DNA keeps SWNT colloidally stable.

Figure 10A:
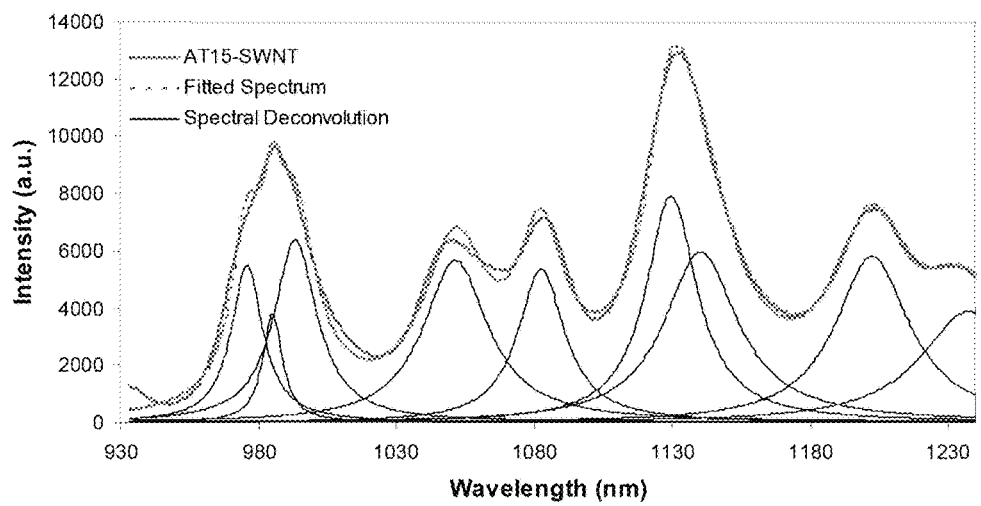
FIG. 10A: nIR fluorescence spectrum (solid green) of AT15-SWNT recorded with a 50× objective upon 785 nm laser excitation. The spectral deconvolution reveals 7 nanotube species and a Raman peak (solid black), and convoluted spectrum (dotted red) as a sum of the individual peaks overlap the actual data.
Figure 10B:
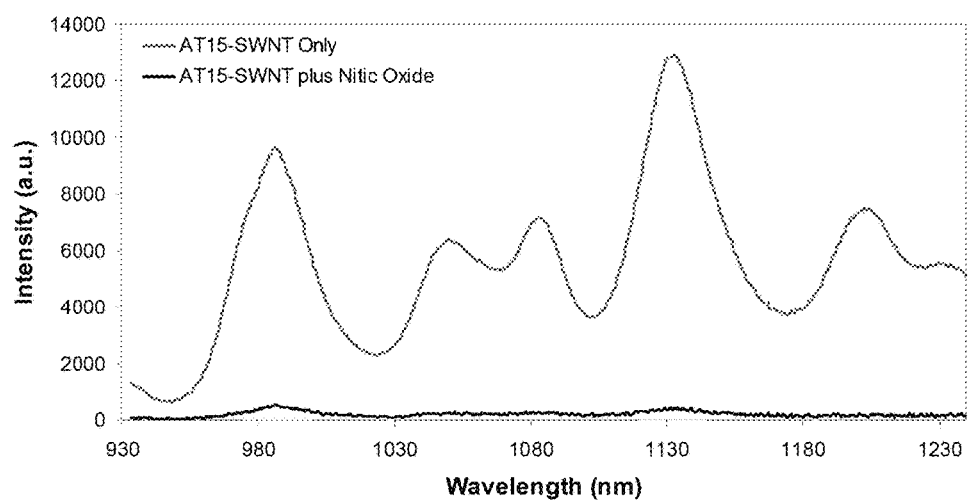
FIG. 10B: Complete quenching (solid blue) of AT15-SWNT fluorescence is observed once the SWNT sample is exposed to NO (60 µM, in 1×PBS).
Figure 11:
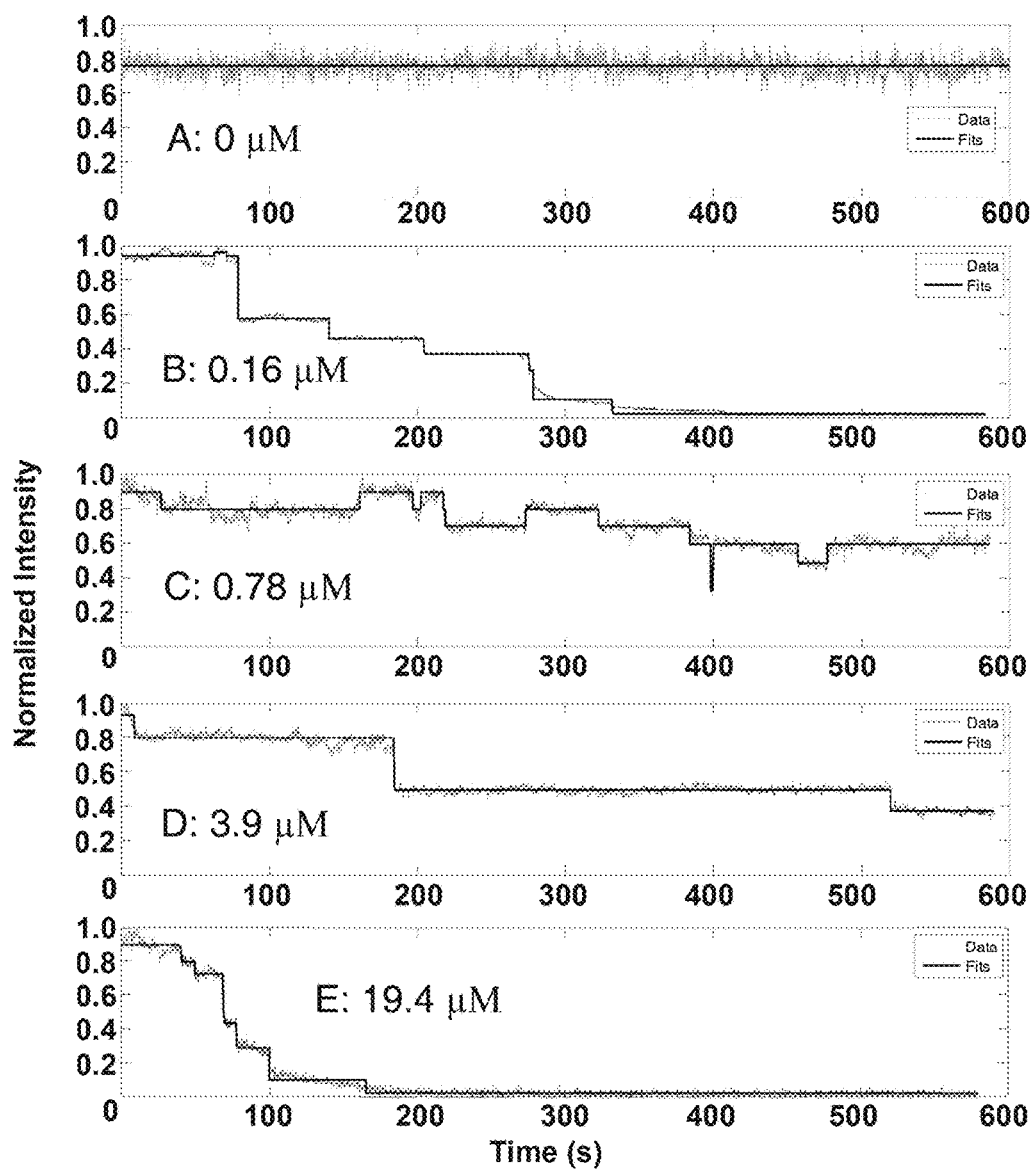
FIGS. 11A-11E: Stepwise fluorescence quenching response of a diffraction-limited segment from the individual SWNT in the sensor array to NO at four different concentrations. Actual experimental data is in red, and the fitted traces (Chi-squared fitting method) is drawn in black.

$AT_{15}$-SWNT showed a very sensitive response to NO spectroscopically. SWNT fluorescence emission spectrum was taken with a home-built near-infrared (nIR) fluorescence microscope. Briefly, upon 785 nm laser excitation, the $AT_{15}$-SWNT (2 mg/l, in 50 mM PBS) sample emits nIR light (900-1300 nm), which is captured by an InGaAs array through a spectrometer. In order to determine individual SWNT species in the SWNT suspension, 2D excitation-emission profile was taken following techniques similar in literature[34]. Using the identified emission peak center of each species, the intensity of each species can be obtained by deconvoluting the fluorescence spectrum using a custom-written Matlab program (FIG. 10A). Upon exposure to nitric oxide (60 µM, in 1×PBS), the fluorescence of all the SWNT species is completely quenched (FIG. 10B).

Materials and methods: DNA Oligonucleotide, Polymer Nanotube Suspension

SWNTs were suspended with both $d(AT)_{15}$ and $d(GT)_{15}$ oligonucleotides using methods similar to those published [16]. Briefly, HiPCO SWNTs purchased from Unidym were suspended with a 30-base (dAdT) or (dGdT) sequence of ssDNA in a 2:1 SWNT:DNA mass ratio in 0.1 M NaCl in distilled water. Samples were sonicated with a 6 mm probe tip (Cole-parmer) for 10 min at power of 10 watts followed by a 180 minute benchtop centrifugation (Eppendorf Centrifuge 5415D) at 16,100×g afterwards the pellet discarded.

For suspension with other polymer materials, SWNTs were first suspended in a 2 wt % sodium cholate (SC) aqueous solution using previously published methods[18, 60]. Briefly, 1 mg/mL NanoC SWNTs were added to 40 mL 2 wt % SC in NanoPure $H_2O$ and were sonicated with a 6 mm probe tip at 40% amplitude (~12 W) for 1 hr in an ice bath. The resulting dark black solution was ultracentrifuged in an SW32 Ti rotor (Beckman Coulter) at 153,700 RCF (max) for 4 hrs to remove unsuspended SWNT aggregates and catalyst particles. The desired polymer for SWNT suspension was then dissolved, at 1 wt %, in the SC-SWNT and the mixture was placed in a 12-14 kD MWCO dialysis bag and dialyzed against 2 L 1×Tris buffer (20 mM, pH 7.3) for 24 hours to remove free SC and allow the polymer to self-assemble on the nanotube surface. The dialysis buffer was changed after 4 hrs to ensure SC removal. The resulting suspensions were clear to the eye and were free of SWNT aggregates, indicating successful suspension[61].

Materials and Methods: Modelling on $AT_{15}$-SWNT Structure

Computations were performed using commercial software package, HyperChem (HyperCube, Fla.). $d(AT)_{15}$ oligonucleotides was obtained from the nucleic acid database, and was drawn in the vicinity to the SWNT. After geometry optimization was performed on the $AT_{15}$ DNA, molecular dynamics simulation using Amber force field was conducted on the $AT_{15}$-SWNT complex. The simulation was run for 1600 psec until the conformation reaches equilibrium.

Example 5

$AT_{15}$-SWNT allows selective quenching only to NO. Using the same microscopy and data analysis methods described above, a high-throughput screening assay where the $AT_{15}$-SWNT was exposed to 36 biological molecules was designed (Table 1), and found that NO was the only molecule that caused complete fluorescence quenching. Notice that concentrations of the majority of the bio-molecules (~500 µM) were much higher than NO (60 µM) in the screening, and others were constrained by their solubility.

TABLE 1

| analyte | concentration (mM) |
| --- | --- |
| 17-α-estradiol | 0.10 |
| 2,4-dinitrophenol | 0.48 |
| acetylcholine chloride | 0.54 |
| α-tocopherol | 0.51 |
| adenosine | 0.51 |
| ATP | 0.11 |
| cAMP | 0.10 |
| creatinine | 0.10 |
| cytidine | 0.48 |
| D-aspartic acid | 0.02 |
| D-fructose | 10.80 |
| D-galactose | 5.00 |
| D-glucose | 10.90 |
| D-mannose | 10.30 |
| dopamine | 0.49 |
| glycine | 0.50 |
| guanosine | 0.51 |
| histamine | 0.51 |
| L-ascorbic acid | 0.50 |
| L-citrulline | 0.11 |
| L-histidine | 0.10 |
| L-thyroxine | 0.10 |
| melatonin | 0.49 |
| NADH | 0.51 |
| nitric oxide | 0.06 |
| quinine | 0.01 |
| riboflavin | 0.10 |

TABLE 1-continued

| analyte | concentration (mM) |
| --- | --- |
| salicylic acid | 0.49 |
| serotonin | 0.11 |
| sodium azide | 0.51 |
| sodium pyruvate | 0.50 |
| sucrose | 0.10 |
| thymidine | 0.52 |
| tryptophan | 0.25 |
| tyramine | 0.49 |
| urea | 0.49 |

In order to understand this selective response of $AT_{15}$, other DNA oligonucleotides, peptides, and other synthesized polymers-wrapped SWNT were screened against the same panel of analytes and they all showed very distinct response profiles compared to $AT_{15}$-SWNT. For instance, $ss(GT)_{15}$ differed from $ss(AT)_{15}$ by only a small change in the one of the bases, but it responded to many more molecules including dopamine, histamine, L-ascorbic acid, melatonin, NADH, NO and riboflavin. Other $ss(AT)_{15}$ variants including $ss(AAAAT)_6$, $ss(AAATT)_6$, $ss(AAT)_{10}$, $ss(ATT)_{10}$, $ss(AAAT)_7$, $ss(AATTT)_6$, $ss(AATT)_7$ showed similar response profiles compared to $ss(AAT)_{10}$, where many other molecules apart from NO also greatly modulated SWNT fluorescence. Surprisingly, poly-vinyl alcohol wrapped SWNT (PVA-SWNT) appeared to be the only polymer-SWNT complexes among over thirty polymers tested that was not quenched by NO. In addition, dopamine induced similar quenching to PVA-SWNT in the typical DNA response profile; however, other reducing agents including NADH, L-ascorbic acid and melatonin that were previously shown to enhance fluorescence of the DNA-SWNT caused quenching of the PVA-SWNT.

The selectivity of $d(AT)_{15}$-SWNT included three components: redox, non-radiative energy loss, and steric. DNA-SWNTs have previously shown selective electrochemical responses to odor gases[35-38], ad specific recognition for SWNT structures[39], although efforts on understanding the recognition mechanisms is still underway. In fact, most of the responses resulted from interaction between redox-active molecules and polymer-SWNT complexes. For instance, LUMO levels of NO (−0.5 vs NHE)[40] and riboflavin (−0.318 vs NHE)[41] were close to conduction band of SWNT, so it is possible that they cause quenching through excited-state electron quenching[42]. Moreover, fluorescence enhancement response caused by reducing agents including NADH, L-ascorbic acid and melatonin on DNA-SWNT was likely because NADH reduces DNA wrapping, recovering DNA-induced pre-quenched fluorescence. More specifically, the LUMO band DNA was below the Fermi level of semiconducting SWNT[43], quenching excited state electrons[42]. HOMO electrons of NADH can compete with excited state electrons for the LUMO level of DNA, inhibiting SWNT excitons from quenching. The DNA-SWNT fluorescence enhancement caused by NADH was weakened as the energy gap between condition band of SWNT and LUMO of DNA molecule decreases, or the diameter of the SWNT increases, supporting the fluorescence enhancing mechanism proposed. In contrast, the mechanism of PVA-SWNT fluorescence quenching caused by reducing agents have not been extensively studied, although other research groups have reported similar results [49]. NADH and other reducing agents may donate electrons directly to the conduction bands of PVA-SWNT, and extra electrons in the conduction bands can quench excitons through a non-radiative Auger recombination[52-53]. Moreover, dopamine seemed to quench all the polymer-SWNT complexes but $AT_{15}$-SWNT, and its HOMO level was between NADH and L-ascorbic acid, therefore we conclude that non-radiative energy transfer from excitons to those molecules is the mechanism. Because the size of dopamine is small, and the benzene structure can pi-pi stack on the SWNT surface, this hypothesis is highly possible.

All the redox responses discussed above are greatly attenuated in the case of $ss(AT)_{15}$-SWNT, implying that steric component contributed the most to the selectivity. The $ss(AT)_{15}$ is very likely to wrap SWNT with closely spaced DNA bands, preventing other molecules getting close to the SWNT surface. AFM images of $AT_{15}$-SWNT suggested that $AT_{15}$ wraps SNWT rather uniformly, resulting in a wrapping structure in the height of 0.5-1 nm above the surface of SWNT, further confirming the hypothesis. Steric selectivity explains that dopamine and riboflavin fail to cause the same quenching of $ss(AT)_{15}$-SWNT and PVA-SWNT respectively. The mechanism of PVA blocking NO deserves further investigation, and we hypothesize that OH group on PVA provides a NO shield on the SWNT surface, preventing NO getting close to the SWNT surface.

Methods and Materials: Nitric Oxide (NO) Solution:

Phosphate buffer saline (PBS, 1×) was contained in a 5 ml round bottom flask and sealed with a septum with two needles inserted providing an inlet and an outlet respectively. After Argon (Airgas) gas was purged for 2 hours to remove dissolved oxygen in the buffer, nitric oxide gas (99.99%, Electronicfluorocarbons) was induced for 20 min at outlet pressure of 2 psi. The concentration of NO was measured using horseradish peroxidase assay[62-63].

Methods and Materials: Atomic Force Microscopy (AFM) Imaging

In this work, two different types of surface were used for AFM imaging for different purposes. In order to verify that SWNT suspension yields individual SWNT and to estimate the height of the wrapping on the SWNT surface, $AT_{15}$-SWNT was deposited on an oxygen plasma pre-wetted silicon dioxide surface. In this case, free DNA was removed from $AT_{15}$-SWNT suspension using spin column (Microspin™S-400HR columns, GE Healthcare), and the suspension was diluted to 10 mg/l. Oxygen plasma (Harrick Plasma) was applied to enhance the hydrophilicity of the silicon dioxide surface, assisting DNA-SWNT adsorption on the surface. The sample was then spin-coated (LaurelI Technology Corporation, model WS-650MZ-23NPP/LITE) for 1 min with ramp speed of 500 RPM and final speed of 2500 RPM.

In order to verify that SWNT is individually deposited on a solid substrate, AFM images were taken using SWNT samples that were deposited on silicon dioxide surface pre-treated with APTES. For sample preparation, the same procedure was used as in the sample required for fluorescence detection, except that the silicon dioxide surface was used for depositing instead of the glass slide, in order to obtain a smoother surface for AFM imaging.

All the AFM images were taken using Asylum Tapping/AC mode soft tips (AC240TS).

Methods and Materials: Measurement of SWNT Fluorescence; Setup for High Throughput Screening Assay All polymer wrapped SWNT solutions were diluted to a final SWNT concentration of 2 mg/l. The following analytes were initially dissolved in DMSO, including ATP, cAMP, creatinine, d-aspartic acid, glycine, 1-citrulline, 1-histidine, quinine, sodium pyruvate; all other analytes dissolved in 1×Tris (20 mM, pH 7.3). Analyte solutions were added to the SWNT, such that the final DMSO concentration was 1 vol %, the mixture was incubated for 1 hr and the resulting SWNT PL was measured with a home-built near infrared (nIR) fluorescence microscope. Briefly, a Zeiss AxioVision inverted microscope was coupled to a Princeton Instruments InGaAs OMA V array detector through a PI Acton SP2500 spectrometer. Sample excitation was from a 785 nm photodiode laser, 450 mW at the source and 150 mW at the sample.

Deconvolution of SWNT PL Spectra:

The fluorescence spectra were fitted using a sum of N=9 Lorentzian lineshapes (8 nanotube peaks and 1 G-prime peak). The fluorescence intensity at any energy, E, is a sum over the contributions of all the species present in solution:

$$I(E) = \sum_{i=1}^{N} \frac{C_i}{2\pi} \frac{\Gamma_i}{(E-E_{0,i})^2 + \Gamma_i^2/4}$$

The parameters to be estimated for the Lorentzian profile of the $i^{th}$ entity have been outlined below.

$C_i$—area under the peak
$\Gamma_i$—full width at half maximum (FWHM, meV)
$E_{0,i}$—peak center in terms of energy (meV)

Initial guesses for the peak areas were calculated from the control spectrum. The area under the $i^{th}$ peak was expressed as a fraction of the total area under the spectrum. This fraction was determined from the intensity of the peak in question. The initial guesses for the FWHM of different nanotubes were obtained either from 2D excitation-emission profile similar to reported[34] or scaled according to their diameters[64] to ensure a good fit. The FWHM and peak center for the G-prime peak were kept constant (11 meV and 1258.72 meV respectively) and only its peak area was floated. In all, 31 parameters were used to fit a single fluorescence spectrum. Each $\Gamma_i(E_{0,i})$ was constrained within a 10 meV (50 meV) window to maintain the physical validity of the fit. For responses such that the degree of quenching is over 50% the shifting response is set to zero due to the difficulty in distinguishing between actual shifting and relative intensity change of different species.

Example 6

A NO sensing SWNT array was realized by depositing individual $AT_{15}$-SWNT on the 3-aminopropyltriethoxysilane (APTES) treated glass bottomed petri dish through charge-charge interactions. FIG. 6 describes the NO detection scheme. Upon 658 nm laser excitation, the SWNT on the array emits stable near-infrared light, which is collected in real-time by a near-infrared two-dimensional array detector through an inverted microscope with 100× objective at a frame rate of 0.2 s/frame. In the fluorescence image (FIG. 6A), each individual $AT_{15}$-SWNT is shown as a diffraction-limited fluorescent spot of approximately 2×2 pixelated size. Each pixel is 290 nm. Atomic force microscopy (AFM) image confirms that $AT_{15}$-SWNT is individually deposited on the substrate. Once the array is expose to NO, stepwise photoluminescence quenching of fluorescence of each SWNT in the array is observed over time (FIGS. 11A-11E). Each trace is normalized to the difference between the starting intensity of the SWNT and the baseline intensity which is obtained through averaging intensity over a 20×20 spot that does not contain SWNTs at the beginning of each movie. NO adsorbs on the unwrapped areas on the SWNT, excitons that formed near the NO adsorption site and within one exciton diffusion length are non-radiatively quenched when they reach the site. Therefore, sparse adsorption of NO on the SWNT causes stepwise decrease in the SWNT fluorescence signal. Similar results have been reported on detection for $H^+$[20], $H_2O_2$[23-24] and $Fe(CN)_6^{3-}$[23] and diazonium[21-22]. Each quenching step reports a single molecule NO adsorption event, and each fluorescence enhancing step reflects a desorption event. Now consider a single SWNT being divided into N segments, each of which is in the size of the exciton-diffusion length. At any instance, we have,

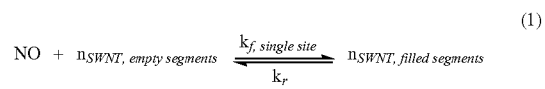

(1)

Rewrite reaction (1) in terms of a differential equation, we have

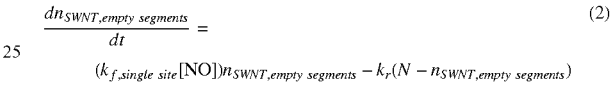

(2)

In equation (2), we lumped concentration of NO into forward (adsorption) rate constant, $$k_f = k_{f,single\ site}[NO] \quad (3)$$

based on the assumption that there are many more NO molecules than SWNT segments in our experiments, and adsorption and desorption of NO on the SWNT will not affect the concentration of NO in bulk. We are more interested in $k_f$ than $k_r$ because the former provides a measure of concentration of NO in this case, although both $k_f$ and $k_r$ will affect the fluorescence response. Note that the concentration of NO determines both the degree of quenching of the fluorescence over the observation time, as well as the rate it quenches. The representative traces in FIGS. 11A-11E indicated that within 600 s, around 40%, 60%, 100% and 100% of quenching were observed when the sensor was exposed to 0.2 μM, 1 μM, 5 μM, and 25 μM of NO respectively. In addition, 100% quenching of the SWNT occurs much faster in the case of 25 μM exposure than that of the 5 μM exposure. Moreover, only at low concentration were desorption steps observed, which indicates that $k_f$ becomes less dominant as concentration of NO decreases, and this observation is consistent with that is predicted by equation (2) and (3). This experimental observation motivates us to look into a generic analysis method that is capable of relating NO concentration to the rate of quenching.

Materials and Methods: Microscopy and Data Collection for Single Molecule NO Detection:

$AT_{15}$-SWNTs were deposited onto a Petri dish pre-treated with 3-aminopropyltriethoxysilane (APTES) substrate, and 3 times of washing removed suspended SWNT as free DNA in the sample. The charge-charge interaction between $AT_{15}$-SWNT and APTES is enough to keep the construct stable at physiological pH. The microscopy technique is similar to that reported in the literature[23]. Briefly, samples were excited by a 658 nm laser (LDM-OPT-A6-13, Newport Corp) at 35 mW. The fluorescence of $AT_{15}$-SWNT was imaged and monitored in real time through a 100×TIRF objective for hours using an inverted microscope (Carl Zeiss, Axiovert 200), with a 2D InGaAs array (Princeton Instruments OMA 2D) attached. Movies were acquired at 0.2 s/frame using the WinSpec data acquisition program (Princeton Instruments). Before the experiment, a control movie (same movie length as the experiment movie) was taken to ensure a stable baseline. In the experiment, nitric oxide (200 nM) in Tris (1×, pH 7.3) buffer was injected through a fine hole, allowing minimal exposure to air.

Adsorption or desorption of nitric oxide onto the $AT_{15}$-SWNT surface causes SWNT PL stepwise increases and quenching. The fluorescence within a 2×2 pixel spatial binning region in the movie images is examined and the analysis algorithm is similar to that reported before[20, 23]. Briefly, the four-pixel area in the image corresponds to a 600×600 $nm^2$ region in the real sample, representing the PL from a single SWNT, which is determined by the diffraction limit in the nIR range[20, 58, 65]. For each SWNT, 100 time traces were extracted from each movie, and each trace records the fluorescence change with time.

Example 7

Previous work developed in our laboratory reported that bulk concentration of a quencher molecule, $H_2O_2$, can be estimated by recording adsorption and desorption events occurred on a film of collagen-wrapped SWNTs over the observation time of 3000 s[23]. Briefly, we used *Hidden Markov Model* (*HMM*) [23, 54] to distinguish actual stepwise transitions from noise in the fluorescence time traces and convert transitions from all the traces (usually 100 traces) into an averaged transition probability matrix which can be used to estimate $k_f$ and $k_r$. One limitation of this method is that it does not take into account the dwell time between transitions, which in fact also contains the rate information[55]. And because HMM neglects the data occurring during the dwell time and only uses data from transitions, this method usually requires a great amount of transitions to provide an accurate parameter estimation. We showed that only one transition occurred between two adjacent levels during our observation time, which is obviously not sufficient to compute transition probability matrix through each trace. For the same reason, we used 100 trace per film in order to narrow the standard deviation in estimating the rate constant, in our previous work[23]. However, by doing this, we also lost our ability to resolve concentration through each sensor, or spatially. In a follow-up, we again used HMM to extract the number of transitions for SWNT over time but did not average all the events into an averaged transition probability matrix, therefore, spatial information was retained[24]. However, there was not a good method proposed to relate the transition frequency into concentration at each sensor level.

Figure 12:
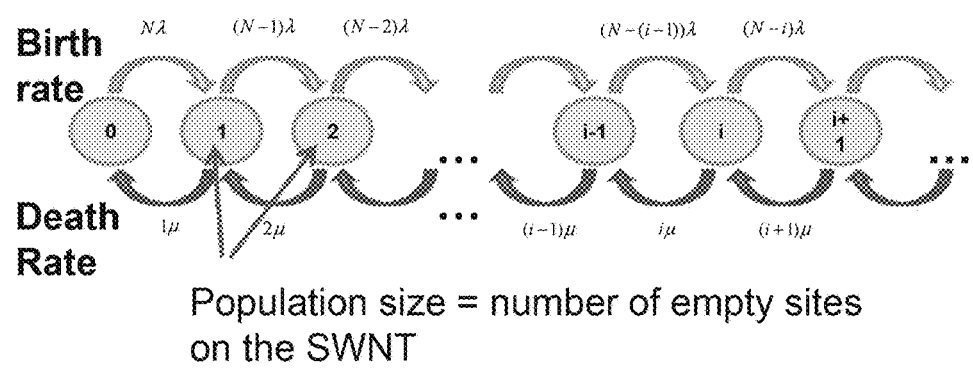
FIG. 12: State transition-rate diagram of the birth-and-death process. The numbers in the circle indicate the states, or the population sizes of the birth-and-death process at any instant; and in the case of single-molecule adsorption, those numbers also indicate the number of empty sites on a single SWNT. Green arrows represent possible birth transitions between states with a birth rate of $(N-i)\lambda$ for a population size of i, and red arrows represent possible death transitions between states with a death rate of $i\mu$ for a population size of i.

In order to determine NO concentration at each SWNT level, we developed a new stochastic analysis method based on a special Markov model, birth-and-death process, which leads to better accuracy and higher spatial resolution. To detail this further, we found that the stochastic quenching on the DNA-SWNT system is physically similar to the birth-and-death Markov model, where a population undergoes deaths and births over a period of observation, t, and the size of the population, $X_t$, changes accordingly. Again suppose a single SWNT can be divided into N segments, each of which is in the size of the exciton-diffusion length. The fast moving excitons in a single segment can be completely quenched once a single NO molecule adsorbs anywhere on that segment. Therefore, a single SWNT can be simply visualized as a 1D array that contain N reactive sites. In the view of the birth-and-death Markov process, a single SWNT is a population with both starting and maximum population size of N. Notice that the exact length of exciton-diffusion does not affect the analysis. Now consider a quenching adsorption event as a "death" event since it results in a fluorescence decrease, and a desorption event therefore as a "birth" event. How the population size changes over time is of our interest, because it directly relates to the fluorescence response in time. It is clear that the population size at the next time interval (t+h) is greatly affected by the current population size, N(t), as well as the probability of a "death" or "birth" occurring on any individual in the population. Similarly, the number of empty sites on a single SWNT in the next moment is dependent upon the current number of empty sites on the SWNT combined with the single-site adsorption and desorption rates. Define the single-site adsorption and desorption rates of NO on SWNT as p and) respectively, and this process can be described using a typical state transition-rate diagram as shown in FIG. 12 or in a probability form, either of which is another representation of the differential equation (2).

$$P(X_{t+h} = j \mid X_t = i) = \begin{cases} (N-i)\lambda h + o(h) & (j = i+1), \\ 1 - (N-i)\lambda h + i\mu h + o(h) & (j = i), \\ i\mu h + o(h) & (j = i-1), \\ o(h) & (\text{otherwise}) \end{cases} \quad (4)$$

More specifically, the probability of a birth event (the number of sites goes from i to i+1) happening in the next small time interval is proportional (N−i)λ, and the probability of a death event (the number of sites goes from i to i−1) is proportional to iμ. Note that μ, or the single-site adsorption rate constant, is linearly dependent of the concentration of quencher; while λ, or the single-site desorption rate constant, is a constant. Therefore, accurate estimation of μ provides a proper calibration of the quencher's concentration. Notice that the process mentioned above is not a typical linear birth-and-death process that is well described in literature where both birth and death rates are proportional to population size, i. However, applying the theory of the maximum likelihood estimation (MLE)[56-57] to this process allows one to estimate the only two process parameters μ and λ from the observation on the change of site population in a single SWNT. Briefly, the parameter space for a birth-and-death process, $\vec{\theta}=(\mu,\lambda)$, can be estimated through deriving the likelihood function, $L_t(\vec{\theta})$, and computing $\vec{\theta}_{max}$ that maximizes $L_t(\vec{\theta})$ taking the first order derivative. The process parameter $\vec{\theta}_{max}$ is also named as maximum likelihood estimator (MLE), and in this case is a two dimensional vector, $$\vec{\theta}_{max} = (\hat{\mu}_{MLE}, \hat{\lambda}_{MLE}) = \left(\frac{D_t}{S_t}, \frac{B_t}{N \cdot t - S_t}\right) \quad (5)$$

where $D_t$ and $B_t$ being the number of birth and death in the time interval [0, t]. We use $\hat{\mu}_{MLE}$ and $\hat{\lambda}_{MLE}$ to denote MLE estimator for μ and λ. And $B_t+D_t$ equals the total number of transition events. $S_t$ is defined as $\int_0^t X_u du$, the total time lived by the population in the time interval [0, t].

Note that the birth-and-death model employed in this work was derived from the differential equation (2), therefore it correctly reflects the very nature of the underlying process; whereas the HMM is just an approximation relying on various ideal assumptions. In addition, the time that the underlying process stays at each particular state before next transition is a random variable whose distribution is obviously state-dependent. While being neglected by HMM, this dependency is explicitly captured by the linear birth-death process.

Materials and Methods: Maximum Likelihood Estimator, µ and λ, Based on Birth-and-Death Markov Process For a Birth-and-death process, the process parameter space $\vec{\theta} = (\mu, \lambda)$ can be estimated through deriving the likelihood function, $L_t(\vec{\theta})$, and computing $\hat{\theta}_{max}$ that maximizes $L_t(\vec{\theta})$ by taking the first order derivative. And the process parameter $\vec{\theta}_{max}$ is also named as maximum likelihood estimator (MLE).

To discuss this in detail, let $X_t$ be the population size at time t of the birth-and-death process and the maximum number of population is N. And the Markov process can be described $$P(X_{t+h} = j \mid X_t = i) = \begin{cases} (N-i)\lambda h + o(h) & (j = i+1), \\ 1 - (N-i)\lambda h + i\mu h + o(h) & (j = i), \\ i\mu h + o(h) & (j = i-1), \\ o(h) & (\text{otherwise}) \end{cases} \quad (6)$$

We are considering the maximum likelihood estimation of the parameters µ and λ assuming that the process has been observed continuously over some time interval. For a Markov jump process, the likelihood is $$L_t(\vec{\theta}) = \prod_{i=1}^{n(t)} [f(X_i \mid X_{i-1})\lambda(X_{i-1})] \exp^{-\int_0^t \lambda(X_u) du} \quad (7)^{[57]}$$

where θ is the parameter space, and n=n(t) the number of jumps till time, t, and we assume that $X_0$, or the initial population size is non-random.

Note that equation (2) is equivalent to $$L_t(\vec{\theta}) = \prod_{i=0}^{n(t)-1} [f(X_{i+1} \mid X_i)\lambda(X_i)] \exp^{-\int_0^t \lambda(X_u) du} \quad (8)$$

If we consider the birth-and-death process described by equation (1), then we have $$\tau(X_i) = (N - X_i)\lambda + X_i\mu \quad (9)$$

$$f(X_i + d \mid X_i) = \begin{cases} (N - X_i)\lambda/\tau(X_i) & (d = 1), \\ i\mu/\tau(X_i) & (d = -1), \\ 0 & (\text{otherwise}). \end{cases}$$

Substituting in equation (3), $$\begin{aligned} L_t(\theta) &= \prod_{i=0}^{n(t)-1} [g(X_{i+1} \mid X_i)] \exp^{-\int_0^t \tau(X_u) du} \\ &= \lambda^{B_t} \mu^{D_t} \prod_{i=0}^{n(t)-1} [h(X_{i+1} \mid X_i)] \exp^{-\int_0^t \tau(X_u) du} \\ &= \lambda^{B_t} \mu^{D_t} \exp^{-\int_0^t ((N-X_t)\lambda + X_t\mu) du} \prod_{i=0}^{n(t)-1} [h(X_{i+1} \mid X_i)] \\ &= \lambda^{B_t} \mu^{D_t} \exp^{-(N\lambda t + (\mu-\lambda)S_t)} \prod_{i=0}^{n(t)-1} [h(X_{i+1} \mid X_i)] \end{aligned} \quad (10)$$

where $$g(X_i + d \mid X_i) = \begin{cases} (N - X_i)\lambda & (d = 1), \\ i\mu & (d = -1), \\ 0 & (\text{otherwise}) \end{cases}$$

$$h(X_i + d \mid X_i) = \begin{cases} (N - X_i) & (d = 1), \\ i & (d = -1), \\ 0 & (\text{otherwise}) \end{cases}$$

and $B_t$ and $D_t$ being the number of birth and death in the time interval [0,t], and $B_t + D_t = n(t)$. $S_t$ is defined as $\int_0^t X_u du$, the total time lived by the population in the time interval [0,t]

The maximum likelihood estimators (MLE) of (µ,λ) are obtained by maximizing $L_t(\theta)$ $$\frac{\partial [\ln(L_t(\vec{\theta}))]}{\partial \lambda} = \frac{B_t}{\lambda} + S_t - Nt = 0 \quad (11)$$

$$\frac{\partial [\ln(L_t(\vec{\theta}))]}{\partial \mu} = \frac{D_t}{\mu} - S_t = 0$$

So the MLE are $$\hat{\lambda}_{MLE} = \frac{B_t}{Nt - S_t}, \hat{\mu}_{MLE} = \frac{D_t}{S_t}.$$

Example 8

Robustness of the stochastic analysis was tested through applying the birth-and-death MLE method to KMC simulated time traces using various sets of input rates, ($k_{d,Input}$, $k_{r,Input}$). In order to avoid confusion, we use $k_{f,MLE}$ instead of $\mu_{MLE}$ as the estimated adsorption rate, in the following paragraphs.

We simulated 100 time traces at 4 levels of $k_{f,Input}$ (0.0001, 0.001, 0.01 and 0.1 sec$^{-1}$) while keeping $k_{r,Input}$ constant, at 0.00001 sec$^{-1}$. The starting number of empty sites in the MC simulation, N, is chosen to be 10; and both simulation time and observation time are set to be 600 s for each trace. These parameters were chosen such that the simulation produces traces that behave similarly as compared to the actual data shown in FIGS. 11A-11E, in order to provide guidance of the accuracy of this stochastic analysis method in our experimental operating condition. For each trace, a $k_{f,MLE}$ can be obtained through the stochastic analysis described above, and histogram shows the frequency of occurrence of each $k_{f,MLE}$ for 100 traces. Fitted with a normal, the mean and standard deviation of the $k_{f,MLE}$ at each $k_{f,Input}$ can be calculated, and plotted against the input rate, $k_{f,Input}$. A slope of 1 indicated that $k_{f,MLE}$ indeed can be used to calibrate $k_{f,Input}$, and the relatively large standard deviation (plot is in $\log_{10}$ scale) can be attributed to many zero-transition traces, and the MLE estimation method breaks down when there is no transition occurs.

Both the stochastic nature of the process and observation time affect the deviation between $k_{f,Input}$ and $k_{f,MLE}$. For the same set of input rates, the time it takes for the simulated traces to quench differs, so does the degree of quenching within the observation time. The yielded statistic mean of $k_{f,MLE}$ determines the intrinsic operating parameter of the process, which is $k_{f,Input}$ and variances among traces signify the stochastic process. Similarly, in an actual experiment where a small amount of quenching molecules is added, each sensor produces slightly different time traces depending on the local analyte concentration it detects, and estimated mean $k_f$ reflects the intrinsic property of the interaction between the sensor and the analyte. The second factor that may contribute to the deviation is observation time. Equation (5) suggests that sufficient transitions are needed for computing $k_{f,MLE}$ for each individual trace, which requires long observation time especially at low $k_{f,Input}$.

Figure 13A:
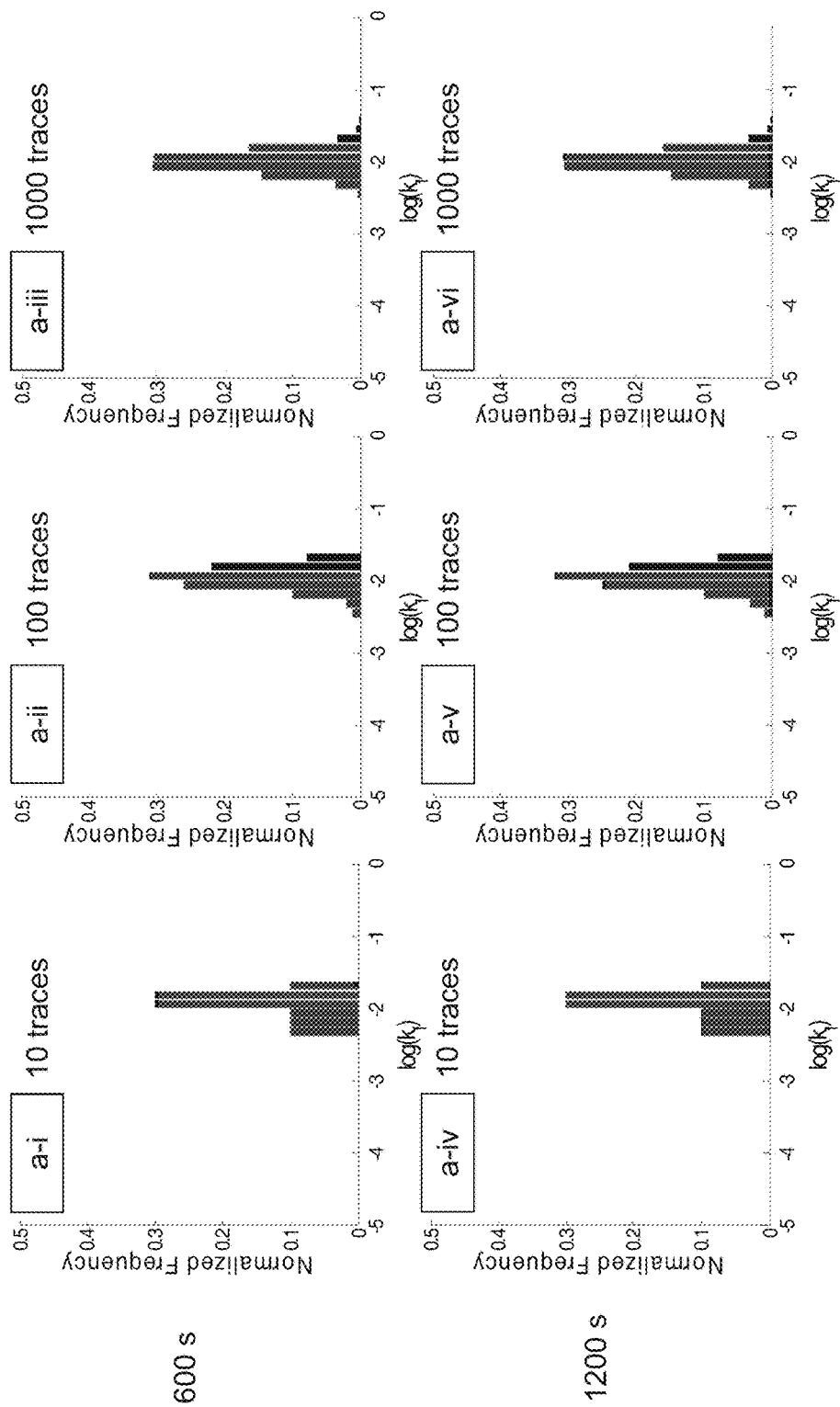
FIG. 13A: Effect of observation time and number of traces on estimation for KMC traces (N=10). a) An example to study the effect of observation time and number of traces on the kf,MLE estimation. Histogram of kf,MLE estimated from 10 (a-i, a-iv, a-vii), 100 (a-ii, a-v, a-viii), 100 (a-iii, a-vi, a-viiii) KMC traces and three different levels of observation time (top panel, 600 s; bottom, 1200 s). Input rates of kf,input=1e-2 s-1, kr,input=1e-5 s-1, and N=10 are chosen as KMC input in this example.
Figure 13B:
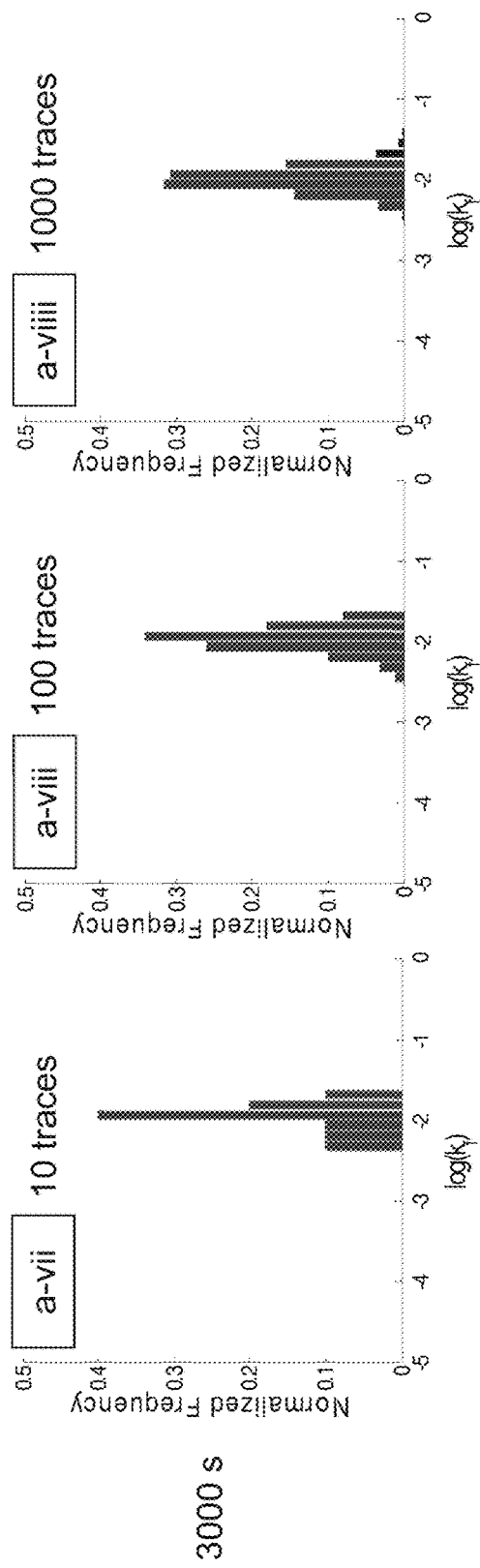
FIG. 13B: Effect of observation time and number of traces on estimation for KMC traces (N=10). a) An example to study the effect of observation time and number of traces on the kf,MLE estimation. Histogram of kf,MLE estimated from 10 (a-i, a-iv, a-vii), 100 (a-ii, a-v, a-viii), 100 (a-iii, a-vi, a-viiii) KMC traces and three different levels of observation time (3000 s). Input rates of kf,input=1e-2 s-1, kr,input=1e-5 s-1, and N=10 are chosen as KMC input in this example.
Figure 13:
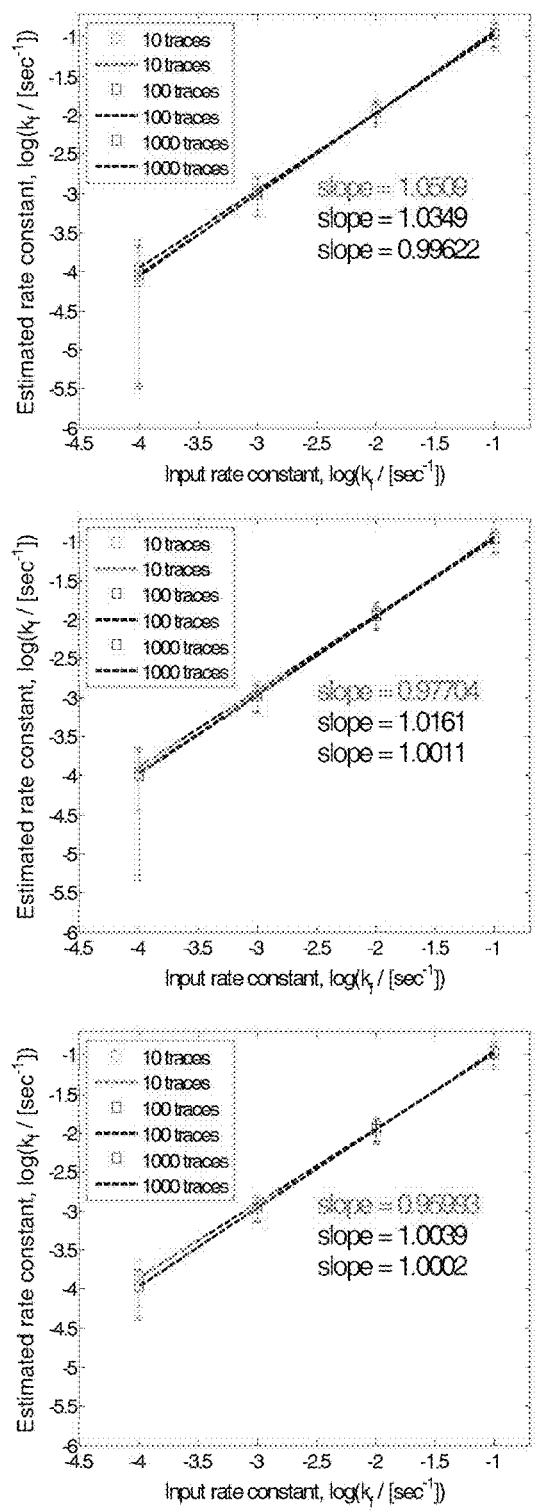
FIG. 13C: The estimated rate constants, kf,MLE and standard deviation of the estimation plotted against the input rate constant of the KMC (N=10) in a log-log scale, and fitted with a linear trend with slope indicated in the figure (square, mean; error bar, standard deviation). Each panel represents kf,MLE value obtained with a different observation time (top, 600 s; middle, 1200 s; bottom, 3000 s).

To understand the both effects and determine a proper observation time, we increased number of traces produced from KMC to 10000, and varied observation time from 600 s to 3000 s for each set of input rates, and calculated $k_{f,MLE}$. To better visualize this approach, histograms of $k_{f,MLE}$ obtained at different observation time or number of traces are plotted. In the example we show in FIGS. 13A-B, a set of medium-range rate constants are used as input, ($k_{f,Input}$, $k_{r,Input}$)=(0.01, 0.0001 s$^{-1}$), and we observed that increasing observation time or increasing number of traces has little effect on $k_{f,MLE}$ distribution. Similarly, we have applied the same analysis to other sets of input rates, and FIG. 13C summarizes the estimated $k_{f,MLE}$ as a function of $k_{f,Input}$ using increasing number of traces, and each panel represents a different option of observation time (a) 600 s, b) 1200 s and c) 3000 s respectively). Linear fitting yields a slope approaching 1 with less than 0.4% error as the number of traces reaches 1000, suggests that $k_{f,MLE}$ can provide a decent calibration for any unknown $k_f$ within the range we tested. It is also interesting to notice that although increasing the number traces produces a more consistent slope (FIG. 13C), the effect on the standard deviation is minimal. This is probably because at high $k_{f,Input}$ including 0.1 and 0.01 s$^{-1}$, majority of the traces have shown completely quenching within 600 s, and prolonging observation time would not affect either $D_t$ or $S_t$ in equation (5), and later observation becomes ineffective. In contract, increasing observation time can significantly decrease the standard deviation for small $k_{f,Input}$ (0.0001 s$^{-1}$), because at low $k_{f,Input}$, only a few transitions occur at the first 600 s. Therefore, prolonging the observation increases the effective transitions, and thus improving the MLE estimation. This conclusion also suggests that experimentally, increasing the observation time is far more effective than increasing the number of SWNTs per experiment for measurements at low concentrations, especially it is impractical to make a SWNT film that contains 10000 single SWNTs per 50×50 µM microscopic view without having the emission from each SWNT interfering with each other. However, because NO is rather diffusive, prolonging the experiments also means losing spatial or temporal resolution, therefore is also not recommended. In fact, at input forward rates as low as 0.0001 s$^{-1}$, notice that even 100 traces consistently yield a slope of 1 with less than 3% error for all the observation time we tested, therefore 600 s will be sufficiently accurate for $k_f$ estimation. This again shows the advantage of the MLE model, because there are only two parameters in the model, $k_f$ and $k_r$, not many transitions are required to provide a decent estimation.

We also noticed that stochastic analysis method appears to over-estimate the $k_{f,Input}$ value. Although the over-estimation is gradually attenuated as the number of traces increases, 10% over-estimation remains even when the number of traces reaches 10000 (Table 2), and the trend appears to be consistent for all the observation time. This is due to the limited maximum number of states associated with a single SWNT. As the starting number of empty sites increases, the quenching profile for each trace approaches its analytical solution, a exponential decay function. In order to validate the consistency of the MLE estimator, we ran KMC simulation at N=1000, and applied the same stochastic analysis to the simulated traces. As expected, the stochastic deviation is significantly attenuated, and the $k_{f,MLE}$ approaches a delta function. $k_{f,MLE}$ estimated from 10, 100 and 1000 traces superimpose on each other, and stochastic mean of $k_{f,MLE}$ exactly matches $k_{f,Input}$, which validates the consistency of this MLE estimation method.

Example 9

Calibration of the AT$_{15}$-SWNT sensor array was carried out by exposing the array to NO solution at different concentrations, ranging from 0.16 µM to 19.4 µM, and the fluorescence quenching response from each individual SWNT was recorded over 600 s at 0.2 s/frame. A custom-written MATLAB program automatically selects 50 brightest diffraction-limited spot with each representing a single SWNT, and extracts the fluorescence intensity in time. We chose the brightest SWNTs to ensure they have less defects chemically and structurally [20, 58], and therefore are sensitive to the changes in the environment and the population of SWNTs we choose is less likely to be heterogeneous. Each trace is subjected to another custom-written MATLAB routine based on the step fitting algorithm described in Ref[59] to distinguish real transition events from noise. Briefly, the algorithm starts by fitting the data with a single large step and locates this first step by computing and minimizing error (Chi-squared) between the fit and the actual data. Subsequent steps are found through fitting new steps to the plateaus generated from previous steps, and the whole process continues. At the same time, a 'counter fit' is generated by placing fits between plateaus in between the current best-fitted steps, and iteration process ends when the ratio between the Chi-squared of the current best fit and the Chi-squared of the 'counter fit' becomes minimal.

Figure 14A:
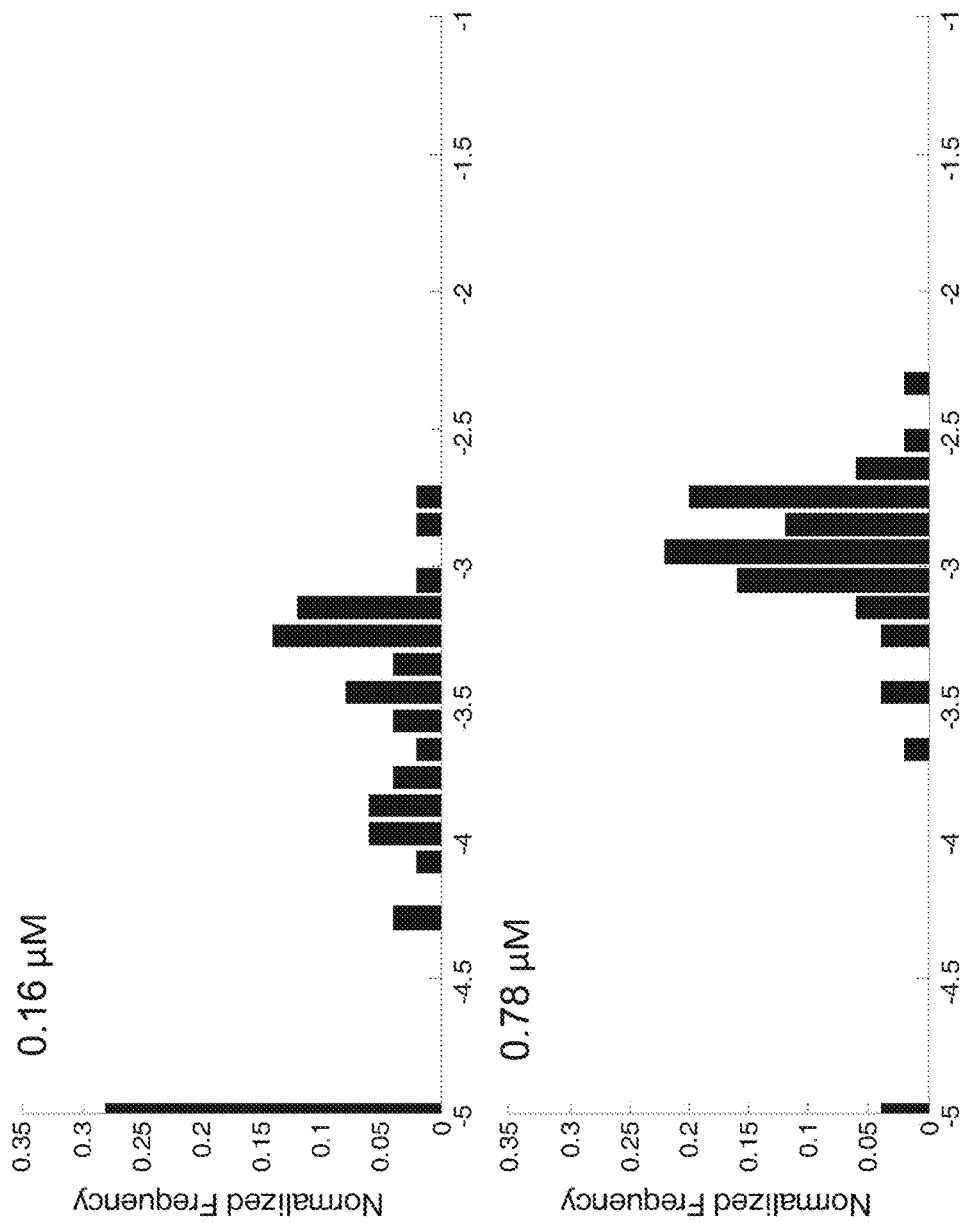
FIG. 14A: Calibration of the AT15-SWNT sensor Array. Histogram of the kf,MLE from the stochastic analysis at different concentrations of NO (top, 0.16 µM; bottom, 0.78 µM). Rates that are lower than 0.00001 s-1.
Figure 14B:
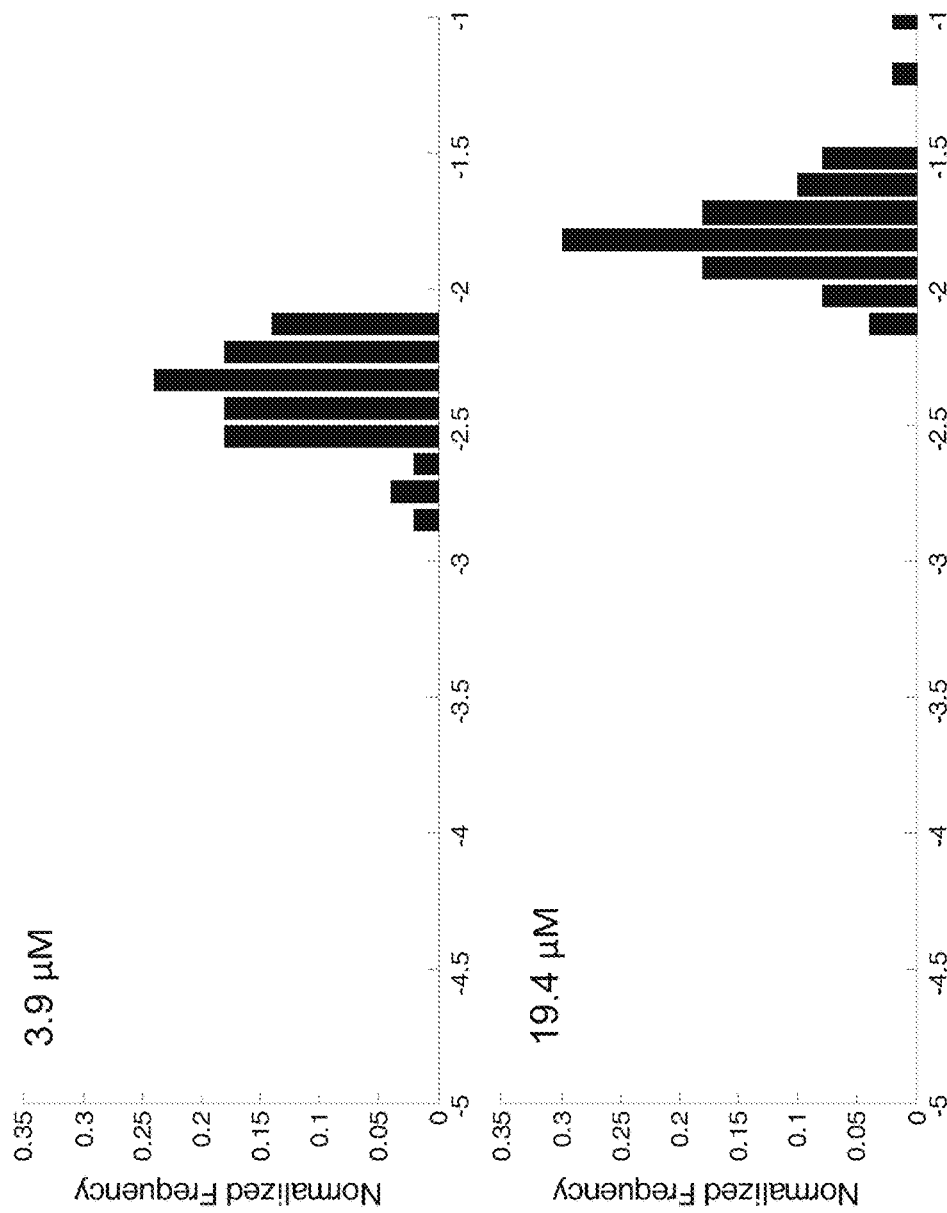
FIG. 14B: Calibration of the AT15-SWNT sensor Array. Histogram of the kf,MLE from the stochastic analysis at different concentrations of NO (top, 3.9 µM; bottom, 19.4 µM). Rates that are lower than 0.00001 s-1.

After all the transitions are identified, we apply the Birth-and-death MLE estimation to each time trace, each SWNT reports NO concentration in the vicinity of the SWNT with great accuracy (FIG. 14). At these low concentration levels (~0.2-20 µM), each sensor detects a slightly different concentration of NO locally. Assuming the rate constants are normally to be normally distributed, the mean values of the $k_{f,MLE}$ shows a linear dependence on the concentration of NO, following the definition of $k_f = k_{f,single\ site} C_{NO}$ with $k_{f,single\ site}$ estimated to be 0.16 sec$^{-1}$ µM$^{-1}$. In fact, the mean value of the rates well describes concentration of the NO with one standard deviation at 1-20 µM, providing a good calibration of the sensor. In addition, the stochastic nature of the process explains the increasing trend of the width of histogram as the concentration decreases. As the concentration of NO decreases, some sensors do not receive any NO molecules, thus reporting a zero forward rate constant, and the width of the histogram is expected to be fairly wide. At this concentration level, reporting the mean value of rate constant is not meaningful. Considering the diffusive and highly reactive property of NO, the linear trend observed experimentally is surprisingly nice, and it reflects the low detection limit of this sensing platform.

REFERENCES

1. Garthwaite, J. and C. L. Boulton, *NITRIC-OXIDE SIGNALING IN THE CENTRAL-NERVOUS-SYSTEM*. Annual Review of Physiology, 1995. 57: p. 683-706.
2. Moncada, S., R. M. Palmer, and E. A. Higgs, *Nitric oxide: physiology, pathophysiology, and pharmacology*. Pharmacological Reviews, 1991. 43(2): p. 109-142.
3. Wink, D. A. and J. B. Mitchell, *Nitric oxide and cancer: An introduction*. Free Radical Biology and Medicine, 2003. 34(8): p. 951-954.
4. Rivot, J. P., et al., *Nitric oxide (NO): in vivo electrochemical monitoring in the dorsal horn of the spinal cord of the rat*. Brain research, 1997. 773(1-2): p. 66-75.
5. Yao, D., A. G. Vlessidis, and N. P. Evmiridis, *Determination of nitric oxide in biological samples*. Microchimica Acta, 2004. 147(1): p. 1-20.
6. Nagano, T. and T. Yoshimura, *Bioimaging of nitric oxide*. Chemical Reviews, 2002. 102(4): p. 1235-1269.
7. Robinson, J. K., M. J. Bollinger, and J. W. Birks, *Luminol/H2O2 chemiluminescence detector for the analysis of nitric oxide in exhaled breath*. Analytical Chemistry, 1999. 71(22): p. 5131-5136.
8. McMurtry, M. S., et al., *Measurement of nitric oxide, nitrite and nitrate using a chemiluminescence assay: an update for the year 2000*. Analusis, 2000. 28(6): p. 455-465.
9. Kojima, H., et al., *Detection and imaging of nitric oxide with novel fluorescent indicators: Diaminofluoresceins*. Analytical Chemistry, 1998. 70(13): p. 2446-2453.
10. Kojima, H., et al., *Fluorescent indicators for imaging nitric oxide production*. Angewandte Chemie International Edition, 1999. 38(21): p. 3209-3212.
11. Sasaki, E., et al., *Highly sensitive near-infrared fluorescent probes for nitric oxide and their application to isolated organs*. Journal of the American Chemical Society, 2005. 127(11): p. 3684-3685.
12. Lim, M. H., D. Xu, and S. J. Lippard, *Visualization of nitric oxide in living cells by a copper-based fluorescent probe*. Nature Chemical Biology, 2006. 2(7): p. 375-380.
13. O'Connell, M. J., et al., *Band gap fluorescence from individual single-walled carbon nanotubes*. Science, 2002. 297(5581): p. 593-596.
14. Saito, R., M. S. Dresselhaus, and G. Dresselhaus, *Physical Properties of Carbon Nanotubes*. 1998, London: Imperial College Press.
15. Heller, D. A., et al., *Single-walled carbon nanotube spectroscopy in live cells: Towards long-term labels and optical sensors*. Advanced Materials, 2005. 17(23): p. 2793-2798.
16. Heller, D. A., et al., *Optical detection of DNA conformational polymorphism on single-walled carbon nanotubes*. Science, 2006. 311(5760): p. 508.
17. Barone, P. W., R. S. Parker, and M. S. Strano, *In vivo fluorescence detection of glucose using a single-walled carbon nanotube optical sensor: Design, fluorophore properties, advantages, and disadvantages*. Anal. Chem., 2005. 77(23): p. 7556-7562.
18. Barone, P. W., et al., *Near-infrared optical sensors based on single-walled carbon nanotubes*. Nature Materials, 2005. 4(1): p. 86-92.
19. Kim, J., et al., *The rational design of nitric oxide selectivity in single-walled carbon nanotube near-infrared fluorescence sensors for biological detection*. Nature Chemistry, 2009. 1(6): p. 473-481.
20. Cognet, L., et al., *Stepwise quenching of exciton fluorescence in carbon nanotubes by single-molecule reactions*. Science, 2007. 316(5830): p. 1465.
21. Siitonen, A., et al., *Dependence of Exciton Mobility on Structure in Single-Walled Carbon Nanotubes*. The Journal of Physical Chemistry Letters, 2010. 1: p. 2189-2192.
22. Siitonen, A. J., et al., *Surfactant-dependent exciton mobility in single-walled carbon nanotubes studied by single-molecule reactions*. Nano Letters, 2010. 10(5): p. 1595-9.
23. Jin, H., et al., *Stochastic analysis of stepwise fluorescence quenching reactions on single-walled carbon nanotubes: single molecule sensors*. Nano letters, 2008. 8(12): p. 4299-4304.
24. Jin, H., et al., *Detection of single-molecule H2O2 signalling from epidermal growth factor receptor using fluorescent single-walled carbon nanotubes*. Nat Nano, 2010. 5(4): p. 302-309.
25. Heller, D. A., et al., *Multimodal optical sensing and analyte specificity using single-walled carbon nanotubes*. Nature Nanotechnology, 2009. 4(2): p. 114-120.
26. Zheng, M., et al., *Structure-based carbon nanotube sorting by sequence-dependent DNA assembly*. Science, 2003. 302(5650): p. 1545-1548.
27. Jin, H., et al., *Divalent Ion and Thermally Induced DNA Conformational Polymorphism on Single-walled Carbon Nanotubes*. Macromolecules, 2007. 40(18): p. 6731-6739.
28. Hughes, M. E., E. Brandin, and J. A. Golovchenko, *Optical Absorption of DNA-Carbon Nanotube Structures*. Nano Letters, 2007. 7(5): p. 1191-1194.
29. Zheng, M., et al., *DNA-assisted dispersion and separation of carbon nanotubes*. Nature Materials, 2003. 2(5): p. 338-342.
30. Meng, S., et al., *DNA Nucleoside Interaction and Identification with Carbon Nanotubes*. Nano Letters, 2006. 7(1): p. 45-50.
31. Manohar, S., T. Tang, and A. Jagota, *Structure of Homopolymer DNA-CNT Hybrids*. The Journal of Physical Chemistry C, 2007. 111(48): p. 17835-17845.
32. Johnson, R. R., A. T. C. Johnson, and M. L. Klein, *Probing the Structure of DNA-Carbon Nanotube Hybrids with Molecular Dynamics*. Nano Letters, 2008. 8(1): p. 69-75.
33. Johnson, R. R., et al., *Free Energy Landscape of a DNA-Carbon Nanotube Hybrid Using Replica Exchange Molecular Dynamics*. Nano Letters, 2009. 9(2): p. 537-541.
34. Bachilo, S. M., et al., *Structure-assigned optical spectra of single-walled carbon nanotubes*. Science, 2002. 298(5602): p. 2361-2366.
35. Johnson, A. T. C., et al., *DNA-decorated carbon nanotubes for chemical sensing*. Semiconductor Science and Technology, 2006. 21(11): p. S17-S21.
36. Johnson, A. J. C., et al., *Employing DNA-Functionalized Carbon Nanotubes to Detect Biologically-Derived Odorants*. Chemical Senses, 2008. 33(8): p. S163-S164.

37. Johnson, A. T. C., et al., *DNA-Coated Nanosensors for Breath Analysis*. Ieee Sensors Journal, 2010. 10(1): p. 159-166.
38. Khamis, S. M., et al., *Homo-DNA functionalized carbon nanotube chemical sensors*. Journal of Physics and Chemistry of Solids, 2010. 71(4): p. 476-479.
39. Tu, X., et al., *DNA sequence motifs for structure-specific recognition and separation of carbon nanotubes*. Nature, 2009. 460(7252): p. 250-253.
40. Bartberger, M. D., et al., *The reduction potential of nitric oxide (NO) and its importance to NO biochemistry*. Proceedings of the National Academy of Sciences of the United States of America, 2002. 99(17): p. 10958-10963.
41. Anderson, R. F., *Energetics of the one-electron reduction steps of riboflavin, FMN and FAD to their fully reduced forms*. Biochimica et Biophysica Acta (BBA)-Bioenergetics, 1983. 722(1): p. 158-162.
42. Satishkumar, B. C., et al., *Reversible fluorescence quenching in carbon nanotubes for biomolecular sensing*. Nat Nano, 2007. 2(9): p. 560-564.
43. Shoda, M., et al., *Probing Interaction between ssDNA and Carbon Nanotubes by Raman Scattering and Electron Microscopy*. The Journal of Physical Chemistry C, 2009. 113(15): p. 6033-6036.
44. Anderson, R. F., *ENERGETICS OF THE ONE-ELECTRON STEPS IN THE NAD+-NADH REDOX COUPLE*. Biochimica Et Biophysica Acta, 1980. 590(2): p. 277-281.
45. Mahal, H. S., H. S. Sharma, and T. Mukherjee, *Antioxidant properties of melatonin: A pulse radiolysis study*. Free Radical Biology and Medicine, 1999. 26(5-6): p. 557-565.
46. Li, Q. W., Y. M. Wang, and G. A. Luo, *Voltammetric separation of dopamine and ascorbic acid with graphite electrodes modified with ultrafine TiO2*. Materials Science & Engineering C-Biomimetic and Supramolecular Systems, 2000. 11(1): p. 71-74.
47. Turyan, Y. I. and R. Kohen, *FORMAL REDOX POTENTIALS OF THE DEHYDRO-L-ASCORBIC ACID L-ASCORBIC-ACID SYSTEM*. Journal of Electroanalytical Chemistry, 1995. 380(1-2): p. 273-277.
48. Tanaka, Y., et al., *Experimentally Determined Redox Potentials of Individual (n,m) Single-Walled Carbon Nanotubes*. Angewandte Chemie-International Edition, 2009. 48(41): p. 7655-7659.
49. Tanaka, Y., et al., *Determination of electronic states of individually dissolved (n,m) single-walled carbon nanotubes in solution*. Chemical Physics Letters, 2009. 482(1-3): p. 114-117.
50. O'Connell, M., E. Eibergen, and S. Doorn, *Chiral selectivity in the charge-transfer bleaching of single-walled carbon-nanotube spectra*. Nature Materials, 2005. 4(5): p. 412-418.
51. Zheng, M. and B. A. Diner, *Solution redox chemistry of carbon nanotubes*. Journal of the American Chemical Society, 2004. 126(47): p. 15490-4.
52. Wang, F., et al., *Observation of rapid Auger recombination in optically excited semiconducting carbon nanotubes*. Physical Review B, 2004. 70(24): p. 241403.
53. Dukovic, G., et al., *Reversible Surface Oxidation and Efficient Luminescence Quenching in Semiconductor Single-Wall Carbon Nanotubes*. Journal of the American Chemical Society, 2004. 126(46): p. 15269-15276.
54. McKinney, S. A., C. Joo, and T. Ha, *Analysis of single-molecule FRET trajectories using hidden Markov modeling*. Biophysical journal, 2006. 91(5): p. 1941-1951.
55. Gillespie, D. T., *Exact stochastic simulation of coupled chemical reactions*. J. Phys. Chem., 1977. 81(25): p. 2340-2361.
56. Keiding, N., *MAXIMUM LIKELIHOOD ESTIMATION IN BIRTH-AND-DEATH PROCESS*. Annals of Statistics, 1975. 3(2): p. 363-372.
57. Feigin, P. D., *MAXIMUM LIKELIHOOD ESTIMATION FOR CONTINUOUS-TIME STOCHASTIC-PROCESSES*. Advances in Applied Probability, 1976. 8(4): p. 712-736.
58. Siitonen, A. J., et al., *Surfactant-Dependent Exciton Mobility in Single-Walled Carbon Nanotubes Studied by Single-Molecule Reactions*. Nano Letters, 2010. 10(5): p. 1595-1599.
59. Kerssemakers, J. W. J., et al., *Assembly dynamics of microtubules at molecular resolution*. Nature, 2006. 442(7103): p. 709-712.
60. O'Connell, M. J., et al., *Band gap fluorescence from individual single-walled carbon nanotubes*. Science, 2002. 297(5581): p. 593.
61. Barone, P. W. and M. S. Strano, *Reversible control of carbon nanotube aggregation for a glucose affinity sensor*. ANGEWANDTE CHEMIE, 2006. 118(48): p. 8318.
62. Kojima, H., et al., *Detection and Imaging of Nitric Oxide with Novel Fluorescent Indicators: Diaminofluoresceins*. Analytical Chemistry, 1998. 70(13): p. 2446-2453.
63. Kikuchi, K., T. Nagano, and M. Hirobe, *Novel detection method of nitric oxide using horseradish peroxidase*. Biological & Pharmaceutical Bulletin, 1996. 19(4): p. 649-651.
64. Inoue, T., et al., *Diameter dependence of exciton-phonon interaction in individual single-walled carbon nanotubes studied by microphotoluminescence spectroscopy*. Physical Review B, 2006. 73(23): p. 233401.
65. Siitonen, A. J., et al., *Dependence of Exciton Mobility on Structure in Single-Walled Carbon Nanotubes*. The Journal of Physical Chemistry Letters, 2010. 1(14): p. 2189-2192.

Each of the above references is incorporated by reference in its entirety.

Other embodiments are within the scope of the claims.

What is claimed is:

1. A system for detecting nitric oxide, comprising:
a substrate;
a linker including a silane, wherein the substrate is modified by the linker; and
a nanosensor interacting with the linker, wherein the nanosensor comprises
a photoluminescent nanostructure; and
a polymer including an oligonucleotide or a polynucleotide modified to enhance detection of the nitric oxide interacting with the photoluminescent nanostructure by adopting a shape in which interactions between the nitric oxide and the photoluminescent nanostructure are relatively energetically favored,
wherein the nanosensor emits a first emission of electromagnetic radiation in the absence of the analyte, and
the nanosensor emits a second emission of electromagnetic radiation upon interacting with the nitric oxide.

2. The system of claim 1, wherein the photoluminescent nanostructure comprises a carbon nanotube.

3. The system of claim 2, wherein the carbon nanotube is a single-walled carbon nanotube.

4. The system of claim 3, wherein the single-walled carbon nanotube is a semiconductive single-walled carbon nanotube.

5. The system of claim 1, wherein the oligonucleotide includes oligo(AT), or the polynucleotide includes poly(AT).

6. The system of claim 1, wherein the photoluminescent nanostructure emits near-infrared radiation in the absence of the nitric oxide.

7. The system of claim 1, wherein the photoluminescent nanostructure emits near-infrared radiation in the presence of the nitric oxide.

8. The system of claim 1, wherein the nanosensor emits electromagnetic radiation of a first intensity in the absence of the nitric oxide, and the nanosensor emits electromagnetic radiation of a second intensity that is less than the first intensity upon interacting with the nitric oxide.

9. The system of claim 1, wherein the nitric oxide is within a cell.

10. The system of claim 1, wherein the nitric oxide is produced by a cell.

11. The system of claim 1, wherein the concentration of the nitric oxide is less than 1 micromolar.

12. The system of claim 1, wherein the interaction between the nitric oxide and the nanosensor includes an interaction between the nitric oxide and the photoluminescent nanostructure.

13. The system of claim 1, wherein the nanosensor interacts with the linker through charge-charge interactions.

14. The system of claim 1, wherein the linker is a silane.

15. The system of claim 1, wherein the concentration of the nitric oxide is less than 100 micromolar.

* * * * *